US009149025B2

(12) United States Patent
Desmecht et al.

(10) Patent No.: US 9,149,025 B2
(45) Date of Patent: Oct. 6, 2015

(54) POLYNUCLEOTIDE FOR USE IN TREATMENT OF INFLUENZA A VIRUS INDUCED DISEASES, ENCODING MODIFIED MX PROTEIN, SAID MODIFIED MX PROTEIN, AND A TRANSGENIC ANIMAL EXPRESSING GENE ENCODING MODIFIED MX PROTEIN

(75) Inventors: Daniel Desmecht, Liege (BE); Anne Marie Louisa Ghislaine Cornet, Harze (BE)

(73) Assignee: UNIVERSITE DE LIEGE, Angleur (BE)

( * ) Notice: Subject to any disclaimer, the term of this patent is extended or adjusted under 35 U.S.C. 154(b) by 46 days.

(21) Appl. No.: 13/579,560

(22) PCT Filed: Feb. 19, 2010

(86) PCT No.: PCT/EP2010/052088
§ 371 (c)(1),
(2), (4) Date: Oct. 11, 2012

(87) PCT Pub. No.: WO2011/101031
PCT Pub. Date: Aug. 25, 2011

(65) Prior Publication Data
US 2013/0245100 A1    Sep. 19, 2013

(51) Int. Cl.
*A01K 67/00* (2006.01)
*A01K 67/027* (2006.01)
*C07K 14/47* (2006.01)
*C07K 7/06* (2006.01)

(52) U.S. Cl.
CPC .............. *A01K 67/0275* (2013.01); *C07K 7/06* (2013.01); *C07K 14/47* (2013.01); *C07K 14/4718* (2013.01); *A01K 2217/05* (2013.01); *A01K 2217/052* (2013.01)

(58) Field of Classification Search
CPC ........... A01K 67/0275; A01K 2217/05; A01K 2217/052
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 5,545,808 A * | 8/1996 | Hew et al. | 800/20 |
| 5,573,933 A * | 11/1996 | Seamark et al. | 800/25 |
| 5,891,698 A * | 4/1999 | Prieto et al. | 800/7 |
| 7,375,258 B2 * | 5/2008 | Harvey et al. | 800/19 |
| 2011/0142850 A1 * | 6/2011 | Subauste | 424/158.1 |
| 2011/0294874 A1 * | 12/2011 | Lee et al. | 514/44 R |

FOREIGN PATENT DOCUMENTS

| | | |
|---|---|---|
| WO | WO 87/00864 A1 | 2/1987 |
| WO | WO 93/14188 A1 | 7/1993 |
| WO | WO 93/15609 A1 | 8/1993 |
| WO | WO 93/19768 A1 | 10/1993 |
| WO | WO 93/20221 A1 | 10/1993 |
| WO | WO 94/06922 A1 | 3/1994 |
| WO | WO 2004/085479 A2 | 10/2004 |
| WO | WO 2006/037052 A2 | 4/2006 |
| WO | WO 2008/039267 A2 | 4/2008 |

OTHER PUBLICATIONS

Arnheiter et al, Current Topics in Microbiology and Immunology, 1996, 206:119-147.*
Baise et al, Journal of Interferon and Cytokine Research, 2004, 24:513-521.*
Influenza—Wikipedia. Printout from en.wikipediao.org/wiki/Influenza, pp. 1-30, printed Feb. 20, 2014.*
Suk et al. Journal of Controlled Release 178:8-17, 2014.*
Arnheiter, H. et al (1996) "Mx Transgenic Mice—Animal Models of Health" *Current Topics in Microbiology and Immunology* 206: 119-147.
Arteaga, C.L. and Holt, J.T. 1996 "Tissue-targeted Antisense c-fos Retroviral Vector Inhibits Established Breast Cancer Xenografts in Nude Mice" *Cancer Res* 56: 1098-1103.
Baise, E. et al (2004) "Conditional Expression of Type I Interferon-Induced Bovine Mx1 GTPase in a Stable Transgenic Vero Cell Line Interferes with Replication of Vesicular Stomatitis Virus" *Journal of Interferon & Cytokine Research* 24: 513-521.
Cannons, J.L. (2002) "Cutting Edge: Profound Defect in T Cell Responses in TNF Receptor-Associated Factor 2 Dominant Negative Mice" *The Journal of Immunology* 169: 2828-2831.
Curiel, D.T. et al. 1991 "Adenovirus enhancement of transferrin-polylysine-mediated gene delivery" *Proc Natl Acad Sci USA* 88: 8850-8854.
Dalesandro, J. et al. 1996 "Cardiac and Pulmonary Replacement, Gene Therapy for Donor Hearts: Ex Vivo Liposome-Mediated Transfection" *J Thorac Cardiovasc Surg* 111: 416-422.
Friedman, J.M. et al. 1986 "Cellular Promoters Incorporated into the Adenovirus Genome: Cell Specificity of Albumin and Immunoglobulin Expression" *Molecular and Cellular Biology* 6: 3791-3797.
Genbank Accession No. U88329, Feb. 22, 1997.
Genbank Accession No. P20591, Dec. 15, 2009.
Haller, O. et al (2007) "Interferon-induced Mx proteins in antiviral host defense" *Biochimie* 89: 812-818.

(Continued)

*Primary Examiner* — Marcia S Noble
(74) *Attorney, Agent, or Firm* — Knobbe, Martens, Olson & Bear, LLP

(57) ABSTRACT

A method can be used for treating or reducing likelihood of an influenza A virus-induced disease in a mammal. The method includes administering a polynucleotide to the mammal. Theis polynucleotide includes a gene encoding Mx protein having a TRAF2 and/or a TRAF6 binding domain. The TRAF2 and/or TRAF6 binding domain can be represented by the sequences P-X-Q/E-E, P-X-Q/E-X-X-D, or P-X-E-E-X-E. The TRAF2 and/or TRAF6 binding domain can also be located in the Mx protein in a position which corresponds to the position of the hexapeptide PEEESE in the bovine Mx1 protein or in a position which is up to 20 amino acid residues upstream or downstream of that position.

5 Claims, 16 Drawing Sheets

(56) References Cited

OTHER PUBLICATIONS

Haller, O. et al (2008) "Protective role of interferon-induced Mx GTPases against influenza viruses" *Revue Sci. tech. Off int. Epiz* 28: 219-231.

Hatzoglou, M. et al. 1990 "Hepatic Gene Transfer in Animals Using Retroviruses Containing the Promoter from the Gene for Phosphoenolpyruvate Carboxykinase" *J Biol Chem* 265: 17285-17293.

Horisberger, M.A. (1988) "The Action of Recombinant Bovine Interferons on Influenza Virus Replication Correlates with the Induction of Two Mx_Related Proteins in Bovine Cells" *Virology* 162: 181-186.

Huber, B.E. et al. 1991 "Retroviral-mediated gene therapy for the treatment of hepatocellular carcinoma: An innovative approach for cancer therapy" *Proc Natl Acad Sci USA* 88: 8039-8043.

Jahroudi, N. and Lynch, D.C. 1994 "Endothelial-Cell-Specific Regulation of von Willebrand Factor Gene Expression" *Molec and Cell Biol* 14: 999-1008.

Jin, W. et al. 1998 "Exon Sequence is Required for Regulated RNA Splicing of the Human Fibroblast Growth Factor Receptor-1 α-Exon" *J Biol Chem* 273: 16170-16176.

Lee, S.-H. et al (2002) "Functional Diversity of Mx ProteinsL Variations on a Theme of Host Resistance to Infection" *Genome Research* 12: 527-230.

Makarov, S.S. et al. 1996 "Suppression of experimental arthritis by gene transfer to interleukin 1 receptor antagonist cDNA" *Proc Natl Acad Sci USA* 93: 402-406.

Maxwell, I.H. et al. 1991 "Expression of the Diphtheria Toxin A-Chain Coding Sequence under the Control of Promoters and Enhancers from Immunoglobulin Genes as a Means of Directing Toxicity to B-Lymphoid Cells" *Cancer Res* 51: 4299-4304.

Miller, N. and Vile, R. 1995 "Targeted vectors for gene therapy" *FASEB J* 9: 190-199.

Morozumi, T. et al. (2009) "Molecular cloning and characterization of porcine Mx2 gene" *Molecular Immunology* 46: 858-865.

Nagy, Z.B. et al. 2006 "Assembling and cloning genes for fusion proteins using reverse transcription one-step overlap extension PCR method" *Analytical Biochemistry* 351: 311-313.

Nolta, J.A. 1996 "Transduction of pluripotent human hematopoietic stem cells demonstrated by clonal analysis after engraftment in immune-deficient mice" *Proc Natl Acad Sci USA* 93: 2414-2419.

Oliveira, H.C.F. et al. 1996 "Human Cholesteryl Ester Transfer Protein Gene Proximal Promoter Contains Dietary Cholesterol Positive Responsive Elements and Mediates Expression in Small Intestine and Periphery While Predominant Liver and Spleen Expression is Controlled by 5'-distal Sequences" *J Biol Chem* 271: 31831-31838.

Palm, M. et al (2010) "Interferon-induced *Sus scrofa* Mx1 blocks endocytic traffic of incoming influenza A virus particles" *Vet Res* 41 (16 pages).

Pavlovic. J. et al. (1995) "Enhanced virus resistance of transgenic mice expressing the human MxA protein" *J. Virol* 69: 4506-4510.

Pearson, W.R. et al. 1988 "Improved tools for biological sequence comparison" *Proc Natl Acad Sci USA* 85: 2444-2448.

Plank, C. et al. 1994 "The Influence of Endosome-disruptive Peptides on Gene Transfer Using Synthetic Virus-like Gene Transfer Systems" *J Biol Chem* 269: 12918-12924.

Raper, S.E. et al. 1996 "Safety and Feasibility of Liver-Directed Ex Vivo Gene Therapy for Homozygous Familial Hypercholesterolemia" *Annals of Surgery* 223: 116-126.

Szoka, F. 1980 "Comparative Properties and Methods of Preparation of Lipid Vesicles (Liposomes)" *Ann Rev Biophys Bioeng* 9: 467-508.

Wurch, T. et al. 1998 "A modified overlap extension PCR method to create chimeric genes in the absence of restriction enzymes" *Biotechnology Techniques* 12: 653-657.

Zhou, J. et al. (2006) "Functional Tumor Necrosis Factor-Related Apoptosis-Inducing Ligand Production by Avian Influenza Virus-Infected Macrophages" *The Journal of Infectious Diseases* 193: 945-953.

Zou, L. et al. 1997 "Isolation of a liver-specific promoter for human growth hormone receptor gene" *Endocrinology* 138: 1771-1774.

* cited by examiner

| | position | P-4 | P-3 | P-2 | P-1 | P0 | P1 | P2 | P3 | |
|---|---|---|---|---|---|---|---|---|---|---|
| huTNFR2 | 422- | P | F | S | K | E | E | C | A | SEQ ID NO: 26 |
| huCD27 | 244- | T | I | P | I | Q | E | D | Y | SEQ ID NO: 27 |
| huCD30 | 559- | H | Y | P | E | Q | E | T | E | SEQ ID NO: 28 |
| huCD30 | 576- | M | L | S | V | E | E | E | G | SEQ ID NO: 29 |
| huCD40 | 248- | A | A | P | V | Q | E | T | L | SEQ ID NO: 30 |
| huOx40 | 260- | R | T | P | I | Q | E | E | Q | SEQ ID NO: 31 |
| huLTβR | 386- | Y | P | I | P | E | E | G | D | SEQ ID NO: 32 |
| huLTβR | 400- | S | T | P | H | Q | E | D | G | SEQ ID NO: 33 |
| huATAR | 266- | T | V | A | V | E | E | T | I | SEQ ID NO: 34 |
| moATAR | 266- | A | E | T | E | E | E | T | A | SEQ ID NO: 35 |
| hu4-1BB | 232- | V | Q | T | T | Q | E | E | D | SEQ ID NO: 36 |
| hu4-1BB | 244- | R | F | P | E | E | E | E | G | SEQ ID NO: 37 |
| mo4-1BB | 230- | T | G | A | A | Q | E | E | D | SEQ ID NO: 38 |
| mo4-1BB | 242- | R | C | P | Q | E | E | E | G | SEQ ID NO: 39 |
| huNIK | 71- | S | S | S | S | E | E | S | G | SEQ ID NO: 40 |
| huNIK | 78- | G | T | T | D | E | E | D | D | SEQ ID NO: 41 |
| boLMP1 | 204- | R | T | P | V | Q | E | S | G | SEQ ID NO: 42 |
| boLMP1 | 219- | R | P | P | V | Q | E | T | G | SEQ ID NO: 43 |
| boLMP1 | 243- | H | P | P | V | Q | E | T | G | SEQ ID NO: 44 |
| boLMP1 | 315- | H | P | P | V | Q | E | T | G | |
| boLMP1 | 359- | H | P | P | I | Q | E | T | G | SEQ ID NO: 45 |
| huTANK | 178- | S | V | P | I | Q | C | T | D | SEQ ID NO: 46 |
| huLMP1 | 202- | P | H | P | Q | Q | A | T | D | SEQ ID NO: 47 |
| raLMP1 | 315- | P | Y | P | I | Q | A | T | D | SEQ ID NO: 48 |
| raLMP1 | 377- | P | H | P | I | Q | A | T | D | SEQ ID NO: 49 |
| raLMP1 | 425- | P | H | P | V | Q | A | S | D | SEQ ID NO: 50 |
| Major motif | (*) | | | p | x | Q/E | E | | | SEQ ID NO: 2 |
| Minor motif | (**) | | | p | x | Q/E | x | x | D | SEQ ID NO: 4 |

Fig. 9B

|  |  | P-5 | P-4 | P-3 | P-2 | P-1 | P0 | P1 | P2 | P3 |  |
|---|---|---|---|---|---|---|---|---|---|---|---|
| huCD40 | 230- | K | Q | E | P | Q | E | I | D | F | SEQ ID NO: 51 |
| moCD40 | 234- | R | Q | D | P | Q | E | M | E | D | SEQ ID NO: 52 |
| huRANK | 341- | R | Q | M | P | T | E | D | E | Y | SEQ ID NO: 53 |
| huRANK | 374- | F | S | E | P | L | E | V | G | E | SEQ ID NO: 54 |
| huRANK | 450- | R | N | P | P | G | E | D | C | E | SEQ ID NO: 55 |
| moRANK | 337- | R | K | I | P | T | E | D | E | Y | SEQ ID NO: 56 |
| moRANK | 370- | F | Q | E | P | L | E | V | G | E | SEQ ID NO: 57 |
| moRANK | 444- | G | N | T | P | G | E | D | H | E | SEQ ID NO: 58 |
| huIRAK1 | 539- | P | P | S | P | Q | E | N | S | Y | SEQ ID NO: 59 |
| huIRAK1 | 582- | P | N | Q | P | V | E | S | D | E | SEQ ID NO: 60 |
| huIRAK1 | 701- | R | Q | G | P | E | E | S | D | E | SEQ ID NO: 61 |
| huIRAK2 | 523- | S | N | T | P | E | E | T | D | D | SEQ ID NO: 62 |
| huIRAK2 | 554- | P | L | L | P | T | E | N | G | E | SEQ ID NO: 63 |
| huIRAKM | 475- | P | S | I | P | V | E | D | D | E | SEQ ID NO: 64 |
| moIRAK | 503- | S | P | S | P | Q | E | N | S | Y | SEQ ID NO: 65 |
| moIRAK | 546- | P | N | Q | P | V | E | S | D | E | SEQ ID NO: 66 |
| moIRAK | 666- | S | Q | G | P | E | E | S | D | E | SEQ ID NO: 67 |
| huRIP2 | 191- | I | Y | M | P | P | E | N | Y | E | SEQ ID NO: 68 |
| Bos, Ovis |  | V |  |  |  |  |  |  |  |  |  |
| Bubalus | 351- | / | D | I | P | E | E | E | S | E | SEQ ID NO: 69 |
| Mx1 |  | K |  |  |  |  |  |  |  |  |  |
|  |  |  |  |  |  |  |  |  |  |  |  |
| Consensus | (*) |  |  |  | p | x | E | x | x | Ar/Ac | SEQ ID NO: 12 |

Fig. 13

```
77.3% identity in 626 residues overlap; Score: 2492.0; Gap frequency: 0.5% bovineMx1,    1 mvhsdlgiee ldspessing sedme
HomoMxA,      1 mvvsevdiak adpaaashpl llngdatvaq knpgsv bovineMx1,   26 SKSNLYSQYEEKVRPCIDLIDSLRSLGVEQDLALPAIAVIGDQSSGKSSVLEALSGVALP
HomoMxA,     37 AENNLCSQYEEKVRPCIDLIDSLRALGVEQDLALPAIAVIGDQSSGKSSVLEALSGVALP
                   *************** ********************************** bovineMx1,   86 RGSGIVTRCPLVLRLKKLGNEDEWKGKVSFLDKEIEIPDASQVEKEISEAQIAIAGEGTG
HomoMxA,     97 RGSGIVTRCPLVLKLKKLVNEDKWRGKVSYQDYEIEISDASEVEKEINKAQNAIAGEGMG
                ***********  * * **** * ** * ***     ****** * bovineMx1,  146 ISHELISLEVSSPHVPDLTLIDLPGITRVAVGNQPPDIEYQIKSLIRKYILRQETINLVV
HomoMxA,    157 ISHELITLEISSRDVPDLTLIDLPGITRVAVGNQPADIGYKIKTLIKKYIQRQETISLVV
                ****     *****************  *  * *** * bovineMx1,  206 VPANVDIATTEALRMAQEVDPQGDRTIGILTKPDLVDKGTEDKVVDVVRNLVFHLKKGYM
HomoMxA,    217 VPSNVDIATTEALSMAQEVDPEGDRTIGILTKPDLVDKGTEDKVVDVVRNLVFHLKKGYM
                 ****** *** ************************************ bovineMx1,  266 IVKCRGQQDIKHRMSLDKALQRERIFFEDHAHFRDLLEEGKATIPCLAERLTSELIMHIC
HomoMxA,    277 IVKCRGQQEIQDQLSLSEALQREKIFFENHPYFRDLLEEGKATVPCLAEKLTSELITHIC
                ******** *     * **** * *********  * ** * bovineMx1,  326 KTLPLLENQIKETHQRITEELQKYGKDIPEEESEKMFCLIEKIDTFNKEIISTIEGEEFV
HomoMxA,    337 KSLPLLENQIKETHQRITEELQKYGVDIPEDENEKMFFLIDKVNAFNQDITALMQGEETV
                * ********************* *  * ** *  ** *     ***  * bovineMx1,  386 EQYDSRLFTKVRAEFSKWSAVVEKNFEKGYEAIRKEIKQFENRYRGRELPGFVNYKTFET
HomoMxA,    397 GEEDIRLFTRLHEFHKWSTIIENNFQEGHKILSRKIQKFENQYRGRELPGFVNYRTFET
                   *  **** *   * * **  *   *   *** * *********** ** bovineMx1,  446 IIKKQVRVLEEPAVDMLHTVTDIIRNTFTDVSGKHFNEFFNLHRTAKSKIEDIRLEQENE
HomoMxA,    457 IVKQQIKALEEPAVDMLHTVTDMVRLAFTDVSIKNFEEFFNLHRTAKSKIEDIRAEQERE
                * *   *  ************* *  * **** * *** ***************** *** *

+
bovineMx1,  506 AEKSIRLHFQMEQLVYCQDQVYRRALQQVREKEAEEEKNKKS---NHYFQSQVSEPSTDE
HomoMxA,    517 GEKLIRLHFQMEQIVYCQDQVYRGALQKVREKELEEEKKKKSWDFGAFQSSSATDSSMEE
                   ***** **** * *** *  *           *    * * bovineMx1,  563 IFQHLTAYQQEVSTRISGHIPLIIQFFVLRTYGEQLKKSMLQLLQDKDQYDWLLKERTDT
HomoMxA,    577 IFQHLMAYHQEASKRISSHIPLIIQFFMLQTYGQQLQKAMLQLLQDKDTYSWLLKERSDT
                ***     * ********* * * * * ********  * **** bovineMx1,  623 RDKRKFLKERLERLTRARQRLAKFPG
HomoMxA,    637 SDKRKFLKERLARLTQARRRLAQFPG
                 ********** *** *** *** ***
```

Fig. 14

81.4% identity in 635 residues overlap; Score: 2611.0; Gap frequency: 0.6%

```
bovineMx1,    1   mvhsdlgiee
SusMx1,       1   mvysnceske pdsvsasnhl l bovineMx1,   11   LDSPESSLNGSEDMESKSNLYSQYEEKVRPCIDLIDSLRSLGVEQDLALPAIAVIGDQSS
SusMx1,      22   LNGNDELVEKSHKTGPENNLYSQYEEKVRPCIDLIDSLRALGVEQDLALPAIAVIGDQSS
                  *          *         ****************** ****************** bovineMx1,   71   GKSSVLEALSGVALPRGSGIVTRCPLVLRLKKLGNE-DEWKGKVSFLDKEIEIPDASQVE
SusMx1,      82   GKSSVLEALSGVALPRGSGIVTRCPLVLKLKKLVNEEDEWKGKVSYRDSEIELSDASQVE
                  *************************     ********  *  *   **** bovineMx1,  130   KEISEAQIAIAGEGTGISHELISLEVSSPHVPDLTLIDLPGITRVAVGNQPPDIEYQIKS
SusMx1,     142   KEVSAAQIAIAGEGVGISHELISLEVSSPHVPDLTLIDLPGITRVAVGNQPYDIEYQIKS
                  ** * ******* ******************************** ****** bovineMx1,  190   LIRKYILRQETINLVVVPANVDIATTEALRMAQEVDPQGDRTIGILTKPDLVDKGTEDKV
SusMx1,     202   LIKKYICKQETINLVVVPCNVDIATTEALRMAQEVDPEGDRTIGILTKPDLVDKGTEDKI
                   *  ******** ************* ******************* bovineMx1,  250   VDVVRNLVFHLKKGYMIVKCRGQQDIKHRMSLDKALQRERIFFEDHAHFRDLLEEGKATI
SusMx1,     262   VDVARNLVFHLKKGYMIVKCRGQQDIQDQLSLAKALQKEQAFFENHEHFRDLLEEGRATI
                  * ******************* *      **  * *** * ******* * bovineMx1,  310   PCLAERLTSELIMHICKTLPLLENQIKETHQRITEELQKYGKDIPEEESEKMFCLIEKID
SusMx1,     322   PCLAERLTSELIMHICKTLPLLENQIKESHQKITEELQKYGSDIPEDESGKMFFLIDKID
                  **************************   ********   *  *** bovineMx1,  370   TFNKEIISTIEGEEFVEQYDSRLFTKVRAEFSKWSAVVEKNFEKGYEAIRKEIKQFENRY
SusMx1,     382   AFNSDITALIQGEELVVEYECRLFTKMRNEFCKWSAVVEKNFKNGYDAICKQIQLFENQY
                  **  *   * *** *  *  * ***** * * *******      *  *** * bovineMx1,  430   RGRELPGFVNYKTFETIIKKQVRVLEEPAVDMLHTVTDIIRNTFTDVSGKHFNEFFNLHR
SusMx1,     442   RGRELPGFVNYKTFETIIKKQVSVLEEPAVDMLHTVTDLVRLAFTDVSETNFNEFFNLHR
                  ******************** ************* *  * **** * ********* bovineMx1,  490   TAKSKIEDIRLEQENEAEKSIRLHFQMEQLVYCQDQVYRRALQQVREKEAEEEKNKKSNH
SusMx1,     502   TAKSKIEDIKLEQEKEAETSIRLHFQMEQIVYCQDQVYRGALQKVREKEVEEEKNRKSNQ
                  *******  * ******** ****  * ***  * * bovineMx1,  550   YFQSQV---SEPSTDEIFQHLTAYQQEVSTRISGHIPLIIQFFVLRTYGEQLKKSMLQLL
SusMx1,     562   YFLSSPAPSSDPSIAEIFQHLIAYHQEVGKRISSHIPLIIQFFILRTFGQQLQKSMLQLL
                  ** *       *  * **** * *   ******* *  *  ****** bovineMx1,  607   QDKDQYDWLLKERTDTRDKRKFLKERLERLTRARQrlakfpg
SusMx1,     622   QNKDQYDWLLRERSDTSDKRKFLKERLMRLTQARQvprlnra
                  * ********  ** **  ******** *** *** ***

SusMx1,           lqaargl qgtspgnedq ppsltd
```

Fig. 15

```
  1 mvvsevdiak adpaaashpl llngdatvaq knpgsvaenn lcsqyeekvr pcidlidslr
 61 algveqdlal paiavigdqs sgkssvleal sgvalprgsg ivtrcplvlk lkklvnedkw
121 rgkvsyqdye ieisdaseve keinkaqnai agegmgishe litleissrd vpdltlidlp
181 gitrvavgnq padigykikt likkyiqrqe tislvvvpsn vdiatteals maqevdpegd
241 rtigiltkpd lvdkgtedkv vdvvrnlvfh lkkgymivkc rgqqeiqdql slsealqrek
301 iffenhpyfr dlleegkatv pclaekltse lithickslp llenqiketh qriteelqky
361 gvdipeeese kmfflidkvn afnqditalm qgeetvgeed irlftrlrhe fhkwstiien
421 nfqeghkils rkiqkfenqy rgrelpgfvn yrtfetivkq qikaleepav dmlhtvtdmv
481 rlaftdvsik nfeeffnlhr takskiedir aeqeregekl irlhfqmeqi vycqdqvyrg
541 alqkvrekel eeekkkkswd fgafqsssat dssmeeifqh lmayhqeask risshiplii
601 qffmlqtygq qlqkamlqll qdkdtyswll kersdtsdkr kflkerlarl tqarrrlaqf
661 pg
``` ically distant from human Mx proteins, immunopathologic (allergic) problems may arouse from mouse Mx1-based gene

POLYNUCLEOTIDE FOR USE IN TREATMENT OF INFLUENZA A VIRUS INDUCED DISEASES, ENCODING MODIFIED MX PROTEIN, SAID MODIFIED MX PROTEIN, AND A TRANSGENIC ANIMAL EXPRESSING GENE ENCODING MODIFIED MX PROTEIN

TECHNICAL FIELD

The invention relates generally to mutant Mx dynamins and, more specifically, to compositions and methods which utilize these Mx dynamin mutants for prevention or therapy of diseases associated with viral infections. In particular, the invention refers to a polynucleotide for use in treatment of influenza A virus induced diseases, encoding modified Mx protein, said modified Mx protein, and a transgenic animal expressing gene encoding modified Mx protein.

BACKGROUND

Many vaccines were generated and validated for preventing symptoms and mortality associated with viral infections of humans and animals. Some of these vaccines must be frequently updated because of the continuous genetic evolution of the viruses targeted, notably those vaccines aimed at preventing symptoms and mortality attributable to influenza A viruses. Such recurrent updating of the viral strains used to manufacture updated vaccines hamper production of large quantities of vaccines in due time. Moreover, the production costs of these recurrent updatings and the logistic chain that is necessary to ensure quick and wide distribution and administration of these vaccines frequently prevent the pig, chicken, turkey or equine industry from adequately vaccinating all the targeted animals in due time.

In humans, only adamantanes (amantadine, rimantadine) and inhibitors of neuraminidase (oseltamivir, zanamivir) are available for therapy of influenza A viruses-associated diseases. Large scale use of these molecules leads rapidly to emergence of resistant viral strains. As an example, most circulating influenza A virus strains are currently resistant to adamantanes and the prevalence of H5N1 strains resistant to inhibitors of neuraminidase increases constantly. As a consequence, chemotherapeutic molecules capable of mitigating influenza A virus-associated diseases in humans are very scarce.

In humans, the use of monoclonal antibodies to fight viral diseases was proposed. However, as these molecules comprise nonhuman segments, they often cause allergic reactions. Moreover, as many viruses are endowed with a very efficient genetic evolution capacity for evading new therapeutic molecules, the cost/benefit ratio expected from the process of developing a new antiviral monoclonal antibody dramatically hampers the discovery of new molecules.

In humans, gene therapy is an alternative approach to fight diseases as shown in the past for genetic diseases, cancer, or viral diseases (see PCT Publication Nos. WO91/02805, EP 0 415 731 and WO 90/07936). As vectors used in gene therapy transform only a fraction of host cells available for virus amplification, a credible antiviral transgene must encode for a very strong antiviral protein to give the gene therapy process any chance to attenuate the severity of the disease targeted. Such credible transgenes do not exist yet.

In animals, prevention of the spread of economically devastating or anthropozoonotic viral contagious diseases includes mass slaughtering. Today, this sanitary policy faces major economic and ethical concerns. Still in animals, it is theoretically possible to use genetically resistant genitors to disseminate resistance traits among progenies and, hence, progressively enhance the epidemiologic resistance of farm animal populations. However, this approach is based on prior identification of allelic variation at loci encoding for innate resistance against the disease targeted. Such projects are not realistic in terms of cost/success ratio, notably because many disease resistance traits are polygenic.

In 1962, the group of Lindenmann fortuitously discovered that the inbred mouse strain A2G spontaneously resisted experimental infections with influenza A viruses that were systematically fatal for other strains. The new resistance trait was noted Mx, standing for myxovirus resistance. Years after, it appeared that the Mx$^+$ trait cosegregated with the expression, upon interferon alpha/beta (IFNα/β) treatment, of a ~78 kDa protein that was henceforth named Mx protein. Since then, molecular genetic studies led to the identification of the genes underlying Mx proteins expression, first in mice, then in humans and subsequently in all vertebrate species studied. According to sequence homologies, vertebrate Mx proteins were shown to be large dynamin-like GTPases. Dynamins constitute a subfamily of high molecular weight GTPases that play critical functions in a large array of cell processes among which mobility, membrane remodeling, endocytosis, vesicular traffic and division of cell and organelles. Among dynamin molecules, some lack the typical pleckstrin and prolin/arginine-rich domains and their expression is subordinated to type I interferons; these are called "Mx" dynamins. Each vertebrate species possesses two or three Mx genes of which a few allelic versions were shown, in vitro, to encode for Mx dynamins endowed with antiviral activity, most often against influenza A viruses. Further researches revealed that some versions of Mx dynamins were endowed with antiviral properties and that various viruses were targeted, depending on the Mx isoform studied. Targeted mutagenesis studies later showed that the C-terminal GTPase Effector Domain (GED) of Mx dynamins supports antiviral activity and antiviral spectrum.

In the efforts to investigate antiviral activity the *Bos taurus* Mx1 dynamin sequence was made available. In vitro tests with cultured cells expressing bovine Mx1 gene revealed that human and bovine parainfluenza-3, human and bovine respiratory syncytial, bovine viral diarrhea/mucosal disease, Sendai, measles, and encephalomyocarditis viruses were not inhibited by the bovine Mx1, whereas vesicular stomatitis and rabies viruses were. Compared to other Mx dynamins, a specific antiviral spectrum was thus associated to the bovine Mx1 dynamin but as prior art had shown that other Mx dynamins display specific antiviral profiles, this was not unexpected.

With the notable exception of that encoded by the mouse Mx1$^+$ allele, the prior art is deficient in Mx dynamins capable of suppressing influenza A viruses infection-associated diseases in vivo. As influenza A viruses constantly circulate in human, pig and poultry populations, it is trivial that human, porcine or chicken Mx proteins do not protect humans, pigs and chicken against severe, even fatal influenzal disease respectively. Using human, pig or chicken antiviral Mx1 dynamins for gene therapy is therefore not pertinent. Similarly, selection of genitors endowed with the best alleles, as determined in vitro, for raising progressively more resistant chicken or pig populations is not pertinent. Conversely, using the mouse Mx1 dynamin for gene therapy or for generating transgenic influenza-resistant food animals is theoretically pertinent. However, as mouse Mx1 dynamin is phylogenically distant from human Mx proteins, immunopathologic (allergic) problems may arouse from mouse Mx1-based gene therapies or from ingestion of mouse Mx1-containing food. Moreover, bringing murinized chicken, murinized turkey or murinized pig meat on the market would undoubtedly give rise to hostility of consumers. It is therefore highly desirable to use mutant human Mx dynamin with enhanced antiviral activity for gene therapy compositions. Similarly, it is highly desirable to create mutant food animal Mx dynamins with antiviral activity equal or superior to that exercised by mouse Mx1 in vivo in order to generate transgenic influenza-resistant food animals. The antiviral function of all anti-influenza Mx dynamins known so far is exercised through their C-terminal GTPase effector domain (GED).

TNF-receptor associated factors (TRAFs) form an array of adapter molecules that upon engagement of TNF-, IL-1β, TLRs and RANK receptors by their respective cognate ligands come first in contact with the activated receptor, acting as docking molecules for kinases and other effector proteins that are recruited to the activated receptor. TRAFs later regulate the subcellular relocalization of the receptor-ligand complex and modulate the nature and extent of the response by controlling the degradation of key proteins in the pathway. By doing so, TRAFs control activation of protein kinase cascades and transcription factors in the NF-kB and AP-1 families, thus tuning transcription of numerous genes that are involved in proliferation, differentiation and apoptosis.

The prior art is deficient in a method of inhibiting multiplication of viruses and/or to abolish or attenuate viral disease-associated cytokine responses and organ dysfunctions.

Therefore the object of the present invention was to provide animals, preferably transgenic animals which have a decreased susceptibility to influenza A virus. The object was further to provide medicaments for the preventive and or therapeutic treatment of influenza A virus-induced diseases.

Further, the object of the present invention therefore also was to provide a medicament for use in preventive and/or therapeutic treatment of influenza A virus, particularly for human use.

SUMMARY OF THE INVENTION

In the studies according to the present invention surprisingly it has been found that in vitro, compared to other Mx dynamins, the *Bos taurus* Mx1 dynamin displays the most powerful anti-influenza A virus activity ever identified. Moreover, the exceptionally strong anti-influenza A virus activity exercised by this specific Mx dynamin was confirmed in vivo, thus providing the most credible molecule to use in the prevention or treatment of influenza A virus-associated diseases. As anticipated from prior art, this unprecedented antiviral activity was hypothesized to be supported by the C-terminal segment of the protein, the so-called GED. However, the present inventors surprisingly found that substituting the GED by that of any Mx dynamin endowed with weak anti-influenza A virus activity in the *Bos taurus* Mx1 results in a chimeric Mx dynamin still endowed with the aforedescribed exceptional antiviral activity. Conversely, grafting the *Bos taurus* GED on the backbone of a weakly anti-influenza Mx dynamin results in a still weakly anti-influenza chimeric Mx dynamin. The present inventors found a Mx antiviral activity enhancer that is not inserted in the C-terminal GED segment, and therefore represent a GED-independent antiviral motif.

This GED independent antiviral motif is represented by a TRAF2 and TRAF6 binding motif which was identified to be present in *Bos taurus, Ovis aries,* and *Bubalus bubalis* Mx1 backbones that is absent from all vertebrate Mx dynamins tested so far. The present inventors also found that Mx dynamins with this novel TRAF2/TRAF6 binding motif effectively binds TRAF2 and TRAF6 whereas Mx dynamins devoid of this novel TRAF2/TRAF6 binding motif do not. Moreover, during the studies for the present invention it was also found that the presence of this novel TRAF2/TRAF6 binding motif in a Mx backbone is sufficient for driving the unprecedented anti-influenza A activity aforedescribed. In support of these findings, TRAF2/TRAF6 binding motif-deficient mutant *Bos taurus* Mx1 displays a very weak anti-influenza A virus activity. Therefore, the present invention reveals that insertion of a TRAF2 binding domain and/or insertion of a TRAF6 binding domain in a Mx dynamin is sufficient to enhance its anti-influenza A activity.

The present inventors carried out a comparison of the sequence of bovine Mx 1 protein with its counterparts e.g. in chicken, turkey, duck, pig, horse and human which revealed that these Mx1 proteins do not have the above mentioned motif. The present invention therefore provides a new medicament for use in preventive and/or therapeutic treatment of influenza A virus on the basis of these findings.

The present invention therefore provides a polynucleotide for use in preventive and/or therapeutic treatment of influenza A virus induced diseases in mammals, wherein the polynucleotide comprises a gene encoding for Mx protein having a TRAF2 and/or a TRAF6 binding domain.

In a preferred embodiment said TRAF2 and/or said TRAF6 binding domain is located in the middle domain between the N-terminal GTPase domain and the N-terminal GTPase effector domain (GED).

Further preferred, said TRAF2 and/or said TRAF6 binding domain is located between amino acid positions 300 and 450 of the amino acid sequence of said Mx protein.

Still further preferred said TRAF2 and/or said TRAF6 binding domain is located in the Mx protein in a position which corresponds to the position of the hexapeptide PEEESE (SEQ ID NO: 9) in the bovine Mx1 protein or in a position which is up to 20 amino acid residues upstream or downstream of said corresponding position.

In preferred embodiments the TRAF2 and/or a TRAF6 binding domain is located in the Mx protein up to 15, 10, 5, 4, 3, 2, 1 amino acid residues upstream or downstream of the position which corresponds to the position of the hexapeptide PEEESE in the bovine Mx1 protein. However, it is most preferred that the TRAF2 and/or a TRAF6 binding domain is located in the Mx protein in a position which corresponds to the position of the hexapeptide PEEESE in the bovine Mx1 protein.

In a preferred embodiment the Mx protein sequence other than the TRAF2 and/or a TRAF6 binding domain is represented by Mx1 protein or a derivative thereof having at least 95% identity.

In another preferred embodiment of the present invention the Mx protein sequence other than the TRAF2 and/or a TRAF6 binding domain is represented by human Mx1 (MxA) protein or a derivative thereof having at least 95% identity.

In a further preferred embodiment the TRAF2 and/or TRAF6 binding domain is represented by the sequences P/S/T/C/I/A-X-Q/E-X-X-E/D/Y/F/W (SEQ ID NO: 1) or P-X-Q/E-E (SEQ ID NO: 2), preferably P-X-Q/E-X-X-E/D (SEQ ID NO: 3).

In a still further preferred embodiment the TRAF2 binding domain is represented by the amino acid sequence P-X-Q/E-E or P-X-Q/E-X-X-D (SEQ ID NO: 4) and the TRAF6 binding domain is represented by the amino acid sequence P-X-E-X-X-D/E/Y/F/W (SEQ ID NO: 5).

In further preferred embodiments the TRAF2 and/or TRAF6 binding domain is/are represented by P-X-E-X-X-E (SEQ ID NO: 6), preferably by P-X-E-E-X-E (SEQ ID NO:

7), further preferred by P-E-E-E-X-E (SEQ ID NO: 8) and most preferred by P-E-E-E-S-E (SEQ ID NO: 9).

In an alternative embodiment the TRAF2 and/or TRAF6 binding domain is represented by any one of sequences SEQ ID NOs: 26-77.

In another preferred embodiment the polynucleotide of the present invention is for use in preventive and/or therapeutic treatment of influenza A virus induced diseases in human; for which purpose preferably a polynucleotide is used which comprises a gene encoding for Mx protein having a TRAF2 and/or a TRAF6 binding domain, wherein the Mx protein sequence other than the TRAF2 and/or a TRAF6 binding domain is represented by human Mx1 (MxA) protein or a derivative thereof having at least 95% identity. In a particularly preferred embodiment the TRAF2 and/or TRAF6 binding domain is located in the human Mx1 protein in a position which corresponds to the position of the hexapeptide PEEESE in the bovine Mx1 protein. For example, the amino acid sequence PEDENE (SEQ ID NO: 10) of human MxA protein (which is in a position in the human MxA protein which corresponds to the position of the hexapeptide PEEESE (SEQ ID NO: 9) in the bovine Mx1 protein) may be modified to represent a TRAF2 and/or TRAF6 binding domain, e.g. P-E-E-E-N-E (SEQ ID NO: 11) or P-E-E-E-S-E (SEQ ID NO: 9).

Further preferred, the polynucleotide encodes the protein having the amino acid sequence shown FIG. 15 (SEQ ID NO: 17), which represents human MxA, wherein the sequence PEDENE is replaced by PEEESE.

The position in a given Mx protein which corresponds to the position of the hexapeptide PEEESE in the bovine Mx1 protein can be determined by sequence alignment as described further below.

In an alternative preferred embodiment the medicament is adapted for animal use and the Mx protein sequence other than the TRAF2 and/or the TRAF6 binding domain is represented by an Mx protein, preferably other than bovine Mx1, further preferred a naturally existing Mx1 or Mx2 protein of the same animal to be treated. Preferably, for use in preventive and/or therapeutic treatment of influenza A virus induced diseases in *Gallus* sp. (chicken), *Maleagris* sp. (turkey), Anatidae (duck, goose), *Sus* sp. (pig) and *Equus* sp. (horse) the present invention further provides polynucleotides, wherein the polynucleotide comprises a gene encoding for Mx protein, wherein said Mx protein is having a TRAF2 and/or a TRAF6 binding domain which is located in the Mx protein in a position which corresponds to the position of the hexapeptide PEEESE in the bovine Mx1 protein or in a position which is up to 20 amino acid residues upstream or downstream of said corresponding position, and wherein the Mx protein sequence other than the TRAF2 and/or a TRAF6 binding domain is represented by the corresponding *Gallus* sp. (chicken), *Maleagris* sp. (turkey), Anatidae (duck, goose), *Sus* sp. (pig) and *Equus* sp. (horse) Mx protein or a derivative thereof having at least 95% identity, depending on the animal to be treated.

The present invention also provides a polynucleotide for use in preventive and/or therapeutic treatment of infectious salmon anemia virus (an orthomyxovirus) induced diseases in *Salmo* sp. (salmon), wherein the polynucleotide comprises a gene encoding for Mx protein, wherein said Mx protein is having a TRAF2 and/or a TRAF6 binding domain which is located in the Mx protein in a position which corresponds to the position of the hexapeptide PEEESE in the bovine Mx1 protein or in a position which is up to 20 amino acid residues upstream or downstream of said corresponding position, and wherein the Mx protein sequence other than the TRAF2 and/or a TRAF6 binding domain is represented by *Salmo* sp. Mx protein, preferably *Salmo* sp. Mx1, or a derivative thereof having at least 95% identity.

The present invention also provides an alternative embodiment of the medicament for animal use: a polynucleotide for use in preventive and/or therapeutic treatment of influenza A virus induced diseases in *Gallus* sp. (chicken), *Maleagris* sp. (turkey), Anatidae (duck, goose), *Sus* sp. (pig) and *Equus* sp. (horse) comprising a gene encoding bovine, ovine or bubaline Mx1 protein or a derivative thereof having at least 95% identity.

The present invention also provides a polynucleotide for use in preventive and/or therapeutic treatment of influenza A virus induced diseases, wherein the polynucleotide encodes for a peptide having a length of 6 to 50 amino acid residues and is having the sequence P/S/T/C/I/A-X-Q/E-X-X-E/D/Y/F/W or P-X-Q/E-E, preferably P-X-Q/E-X-X-E/D. In a preferred embodiment the sequence P/S/T/C/I/A-X-Q/E-X-X-E/D/Y/F/W is defined as P-X-Q/E-X-X-D or P-X-E-X-X-D/E/Y/F/W.

In a still further preferred embodiment the sequence P/S/T/C/I/A-X-Q/E-X-X-E/D/Y/F/W is defined as P-X-E-X-X-E, more preferred as P-X-E-E-X-E, still further preferred as P-E-E-E-X-E and most preferred as P-E-E-E-S-E.

The polynucleotide of the present invention for use in preventive and/or therapeutic treatment of influenza A virus induced diseases is delivered into the individual in need of such treatment by way of gene therapy. Therefore, the present invention also provides a vector as means for gene therapy for use in preventive and/or therapeutic treatment of influenza A virus induced diseases comprising the polynucleotide of the present invention.

The present invention also provides a polypeptide or peptide encoded by the above mentioned polynucleotide of the present invention for use in preventive and/or therapeutic treatment of influenza A virus induced diseases. Preferably, the present invention provides a polypeptide for use in preventive and/or therapeutic treatment of influenza A virus induced diseases in human, wherein the polypeptide is a Mx protein, wherein said Mx protein is having a TRAF2 and/or a TRAF6 binding domain which is located in the Mx protein in a position which corresponds to the position of the hexapeptide PEEESE in the bovine Mx1 protein or in a position which is up to 20 amino acid residues upstream or downstream of said corresponding position, and wherein the Mx protein sequence other than the TRAF2 and/or a TRAF6 binding domain is represented by human Mx1 (MxA) protein or a derivative thereof having at least 95% identity. Further preferred embodiments of the polypeptide are those as outlined above.

The present invention also provides a peptide for use in preventive and/or therapeutic treatment of influenza A virus induced diseases, wherein the peptide is having a length of 6 to 50 amino acid residues and is having the sequence P/S/T/C/I/A-X-Q/E-X-X-E/D/Y/F/W, preferably P-X-Q/E-X-X-E/D, or P-X-Q/E-E. In a preferred embodiment the sequence P/S/T/C/I/A-X-Q/E-X-X-E/D/Y/F/W is defined as P-X-Q/E-X-X-D or P-X-E-X-X-D/E/Y/F/W. In a further preferred embodiment the sequence P/S/T/C/I/A-X-Q/E-X-X-E/D/Y/F/W is defined as P-X-E-X-X-E, more preferred as P-X-E-E-X-E, still further preferred as P-E-E-E-X-E and most preferred as P-E-E-E-S-E. In another preferred embodiment the peptide has a length of 10 to 40 amino acid residues.

The present invention also provides a non-human transgenic animal having decreased susceptibility for influenza A viruses, comprising as expressed transgene a polynucleotide encoding for a peptide having a length of 6 to 50 amino acid residues and is having the sequence P/S/T/C/I/A-X-Q/E-X-X-E/D/Y/F/W, preferably P-X-Q/E-X-X-E/D, or P-X-Q/E-E.

In a preferred embodiment the sequence P/S/T/C/I/A-X-Q/E-X-X-E/D/Y/F/W is defined as P-X-Q/E-X-X-D or P-X-E-X-X-D/E/Y/F/W.

In a further preferred embodiment the sequence P/S/T/C/I/A-X-Q/E-X-X-E/D/Y/F/W is defined as P-X-E-X-X-E, more preferred as P-X-E-E-X-E, still further preferred as P-E-E-E-X-E and most preferred as P-E-E-E-S-E.

The present invention further provides a non-human transgenic animal having decreased susceptibility for influenza A viruses, expressing a gene encoding a Mx protein, which Mx protein is having a TRAF2 and/or a TRAF6 binding domain; wherein it is optionally provided that the animal does not belong to the taxononic groups of Primates, Bovidae (*Bos, Bubalus, Ovis*), Pinnipedia or Rodentia.

In a preferred embodiment of the transgenic animal the Mx protein sequence other than the TRAF2 and/or a TRAF6 binding domain is not bovine Mx1 protein and preferably is having less than 95% identity, further preferred less than 90% identity to bovine Mx1 protein.

In a preferred embodiment said TRAF2 and/or said TRAF6 binding domain is located in the middle domain between the N-terminal GTPase domain and the N-terminal GTPase effector domain (GED).

Further preferred, said TRAF2 and/or said TRAF6 binding domain is located between amino acid positions 300 and 450 of the amino acid sequence of said Mx protein.

Still further preferred said TRAF2 and/or said TRAF6 binding domain is located in the Mx protein in a position which corresponds to the position of the hexapeptide PEEESE in the bovine Mx1 protein or in a position which is up to 20 amino acid residues upstream or downstream of said corresponding position.

In preferred embodiments said TRAF2 and/or said TRAF6 binding domain is located in the Mx protein up to 15, 10, 5, 4, 3, 2, 1 amino acid residues upstream or downstream of the position which corresponds to the position of the hexapeptide PEEESE in the bovine Mx1 protein. However, it is most preferred that the TRAF2 and/or a TRAF6 binding domain is located in the Mx protein in a position which corresponds to the position of the hexapeptide PEEESE in the bovine Mx1 protein.

The present invention also provides a method for producing a non-human transgenic animal having decreased susceptibility for influenza A viruses, comprising the step of
introduction of a gene encoding a Mx protein, which Mx protein is having a TRAF2 and/or a TRAF6 binding domain; or
introduction of a TRAF2 and/or a TRAF6 binding domain into the endogenous gene encoding Mx protein;
wherein the resulting animal is expressing a gene encoding a Mx protein, which Mx protein is having a TRAF2 and/or a TRAF6 binding domain;
wherein it is optionally provided that the animal does not belong to the taxononic groups of Primates, Bovidae (*Bos, Bubalus, Ovis*), Pinnipedia or Rodentia.

In a preferred method the resulting animal is expressing a gene encoding a Mx protein, wherein said TRAF2 and/or said TRAF6 binding domain is located in the middle domain between the N-terminal GTPase domain and the N-terminal GTPase effector domain (GED).

In a further preferred method the resulting animal is expressing a gene encoding a Mx protein, wherein said TRAF2 and/or said TRAF6 binding domain is located between amino acid positions 300 and 450 of the amino acid sequence of said Mx protein.

In a still further preferred method the resulting animal is expressing a gene encoding a Mx protein, wherein said TRAF2 and/or said TRAF6 binding domain is located in the Mx protein in a position which corresponds to the position of the hexapeptide PEEESE in the bovine Mx1 protein or in a position which is up to 20 amino acid residues upstream or downstream of said corresponding position.

In preferred embodiments the TRAF2 and/or a TRAF6 binding domain is located up to 15, 10, 5, 4, 3, 2, 1 amino acid residues upstream or downstream of the position of the hexapeptide PEEESE in the bovine Mx1 protein. However, it is most preferred, that the TRAF2 and/or a TRAF6 binding domain is located in the Mx protein in a position which corresponds to the position of the hexapeptide PEEESE in the bovine Mx1 protein.

In a preferred embodiment of the animal or the method for its production the gene encoding said Mx protein is an endogenous Mx gene or an introduced transgene. In case the endogenous Mx gene of the animal is modified this gene remains at its original location on the chromosome. Preferably the endogenous Mx gene is modified only in a position which corresponds to the P-E-E-E-S-E motif of bovine Mx1 gene, which position is modified in that way to present a TRAF2 and/or a TRAF6 binding domain. Further preferred the endogenous gene to be modified is Mx1 gene of the respective animal. The position in a different Mx protein which corresponds to the hexapeptide PEEESE of the bovine Mx1 protein can be determined by sequence alignment as described further below.

Alternatively, in order to produce the transgenic animal having decreased susceptibility for influenza A viruses one may introduce a transgene encoding a Mx protein, which Mx protein is having a TRAF2 and/or a TRAF6 binding domain. Suitable genes are the naturally occurring Mx1 gene of *Bos taurus* or *Ovis aries* (sheep), which carry the TRAF2/TRAF6 binding domain P-E-E-E-S-E. However, other Mx genes may be used as Mx backbone (Mx1, Mx2 or Mx3) from the species to be modified or from other species, to construct an artificial Mx transgene to be expressed in the animal as long as the Mx transgene has a TRAF2 and/or a TRAF6 binding domain, preferably in the position which corresponds to the P-E-E-E-S-E motif of bovine Mx1 gene. The position in a different Mx protein which corresponds to the hexapeptide PEEESE of the bovine Mx1 protein can be determined by sequence alignment as described further below.

In an alternative embodiment the Mx protein sequence other than the TRAF2 and/or a TRAF6 binding domain is not bovine Mx1 protein and preferably is having less than 95% identity, further preferred less than 90% identity to bovine Mx1 protein.

Further preferred the animal is selected from *Gallus* sp. (chicken), *Maleagris* sp. (turkey), Anatidae (duck, goose), *Sus* sp. (pig), *Equus* sp. (horse) and *Salmo* sp. (salmon).

In another preferred embodiment of the animal or the method for its production the TRAF2 and/or TRAF6 binding domain is represented by the sequences P/S/T/C/I/A-X-Q/E-X-X-E/D/Y/F/W or P-X-Q/E-E, preferably P-X-Q/E-X-X-E/D.

Further, preferred the TRAF2 binding domain is represented by the amino acid sequence P-X-Q/E-E or P-X-Q/E-X-X-D and the TRAF6 binding domain is represented by the amino acid sequence P-X-E-X-X-D/E/Y/F/W. Still further preferred the TRAF2 and/or TRAF6 binding domain is/are represented by P-X-E-X-X-E, preferably by P-X-E-E-X-E, further preferred by P-E-E-E-X-E and most preferred by P-E-E-E-S-E.

In an alternative embodiment of the animal or the method for its production the TRAF2 and/or TRAF6 binding domain is represented by any one of sequences SEQ ID NOs: 26-77.

Further preferred, the sequences of the Mx protein other than the TRAF2 and/or TRAF6 binding domain are represented by a Mx1 protein. These sequences of the Mx1 protein other than the TRAF2 and/or TRAF6 binding domain may be represented by respective sequences of an existing Mx1 either from the animal species of the transgenic animal or of the animal species to be modified or may be represented by a Mx1 protein from another species, e.g. bovine or ovine, or may be a chimeric Mx1 protein of different species.

The present invention also provides a method of identifying a non-peptide test compound as candidate compound for use in preventive and/or therapeutic treatment of influenza A virus induced diseases, comprising the step of examining binding of TRAF2 and/or TRAF6 to a polypeptide or peptide as defined in claim 11 in the present or absence of said test compound, wherein reduced binding in the presence of said test compound indicates that said test compound is capable of inhibiting the lifecycle of influenza A virus and thereby suitability as candidate compound for use in preventive and/or therapeutic treatment of influenza A virus induced diseases.

In a preferred method a polypeptide is used for examining its binding to TRAF2 and/or TRAF6, which polypeptide is represented by an Mx protein, wherein said Mx protein is having a TRAF2 and/or a TRAF6 binding domain. In further preferred embodiments the TRAF2 and/or a TRAF6 binding domain is represented by P/S/T/C/I/A-X-Q/E-X-X-E/D/Y/F/W, preferably P-X-Q/E-X-X-E/D, or P-X-Q/E-E. In a preferred embodiment the sequence P/S/T/C/I/A-X-Q/E-X-X-E/D/Y/F/W is defined as P-X-Q/E-X-X-D or P-X-E-X-X-D/E/Y/F/W. In a further preferred embodiment the sequence P/S/T/C/I/A-X-Q/E-X-X-E/D/Y/F/W is defined as P-X-E-X-X-E, more preferred as P-X-E-E-X-E, still further preferred as P-E-E-E-X-E and most preferred as P-E-E-E-S-E.

In another preferred embodiment of the method a peptide is used for examining its binding to TRAF2 and/or TRAF6, which peptide is having a length of 6 to 50 amino acid residues and is having the sequence P/S/T/C/I/A-X-Q/E-X-X-E/D/Y/F/W, preferably P-X-Q/E-X-X-E/D, or P-X-Q/E-E. In a preferred embodiment the sequence P/S/T/C/I/A-X-Q/E-X-X-E/D/Y/F/W is defined as P-X-Q/E-X-X-D or P-X-E-X-X-D/E/Y/F/W. In a further preferred embodiment the sequence P/S/T/C/I/A-X-Q/E-X-X-E/D/Y/F/W is defined as P-X-E-X-X-E, more preferred as P-X-E-E-X-E, still further preferred as P-E-E-E-X-E and most preferred as P-E-E-E-S-E. In another preferred embodiment the peptide has a length of 10 to 40 amino acid residues.

DEFINITIONS

The term "Mx dynamins" is used equivalent to the term "Mx protein". The term "MxA" is equivalent with human Mx1.

The term "X" in the amino acid sequences, e.g. in P/S/T/C/I/A-X-Q/E-X-X-E/D/Y/F/W, defines any naturally occurring amino acid residue as glycine, alanine, valine, leucine, isoleucine, phenylalanine, proline, serine, threonine, cysteine, methionine, tryptophan, tyrosine, asparagine, glutamine, aspartic acid, glutamic acid, lysine, arginine, histidine. The symbol "/" indicates alternative amino acid residues in the same position. For example, "Q/E" means that the amino acid position in $P_0$ of the TRAF2/6 binding motif may be either "Q" (Gln, glutamine) or "E" (Glu, glutamic acid). These binding motifs and the definition of their positions are shown in FIG. 9.

The prior art is deficient in an antiviral Mx dynamin endowed with a GED-independent antiviral motif. The provision of such GED-independent antiviral motif is considered to be very useful, because mutant Mx dynamins could be produced combining both domains, thus showing enhanced antiviral activities. The present invention fulfils this long-standing need and desire in the art. The activity enhancers disclosed here can be inserted in any Mx dynamin backbone to enhance its antiviral activity.

The peptidic Mx antiviral activity enhancers disclosed here alter TRAFs biology in a way that is harmful for influenza A viruses and, as such, the present invention will be useful as a novel prophylactic or therapeutic in viral diseases in humans or animals.

Mx dynamins are critical effector proteins for innate inhibition of many viruses in vertebrate species. The present invention develops a novel peptide which, once inserted in a Mx dynamin backbone, dramatically increases its antiviral function. Results shown below indicate that only mutant Mx dynamin with inserted new peptide binds to TNF receptor-associated factors 2 and 6 (TRAF2 and TRAF6). These data indicate that binding of TRAF2 and/or TRAF6 by a mutant Mx dynamin may prove useful as a prophylactic or therapeutic for viral diseases in humans or animals.

The present invention provides peptides that enhances antiviral activity mediated by Mx dynamins, wherein said peptides comprise a functional TRAF2 and/or a TRAF6 binding domain and are inserted in a Mx dynamin backbone. The present invention is further drawn to methods of inhibiting viruses using the peptides disclosed herein. Moreover, the present invention is further drawn to methods of altering TRAF2 and/or TRAF6 functions using a peptide disclosed herein or using a non-peptide analog that mimics the antiviral activity conferred by the mutant Mx dynamins disclosed herein.

In another aspect of the present invention, there is provided a method of identifying a peptide or a non-peptide antiviral molecule capable of inhibiting TRAF2- and/or TRAF6-dependent mechanisms, comprising the step of: preparing a peptide comprising a TRAF2 and/or a TRAF6 binding domain, or preparing a mutant Mx dynamin comprising a TRAF2 and/or a TRAF6 binding domain, and examining binding of TRAF2 and/or TRAF6 to said peptide or mutant Mx dynamin in the presence or absence of a peptide or a non-peptide molecule, wherein reduced binding in the presence of said non-peptide molecule would indicate that said non-peptide molecule is capable of inhibiting viruses.

Most aspects, features, and advantages of the present invention will be apparent from the following description of the presently preferred embodiments of the invention.

DETAILED DESCRIPTION OF THE INVENTION

Description of the Figures

FIG. 3 shows the inhibition of influenza H5N1 multiplication by mouse Mx1 (moMx1) and bovine Mx1 (boMx1) in embryonic fibroblast cultures derived from homozygous congenic moMx1-expressing BALB/c-A2G and transgenic boMx1-expressing ML555 and ML549 mouse lines, respectively. FVB/J has genotype $Mx1^{-/-}$ and BALB/c-A2G has $Mx1^{+/+}$. FVB/J-ML555 is a mouse cell line expressing low level of boMx1 and FVB/J-ML549 is a mouse cell line expressing high level of boMx1. Pools of induced (black boxes) and noninduced (white) cells were infected with influenza A/H5N1 for 48 h. The viral titers in the culture supernatants are plotted. $TCID_{50}$, 50% tissue culture infective dose. Values are means+/−SD from 3 independent experiments.

FIG. 9 summarizes the results of sequence comparison of diverse proteins having TRAF2 and/or TRAF6 binding domains. The unique hexapeptide, "PEEESE" (Pro-Glu-Glu-Glu-Ser-Glu; SEQ ID NO: 9), present in the N-terminal segment of Bos taurus, Ovis aries and Bubalus bubalis Mx1 dynamins is absent from all other Mx dynamins sequenced to date. As this ruminant-specific hexapeptide simultaneously fits with the consensus TRAF2-binding motif pX(Q/E)E (SEQ ID NO: 2) and with the consensus TRAF6-binding motif pXEXX(Ar/Ac) (SEQ ID NO: 12), it is assumed that this hexapeptide functions as a TRAF2-and-TRAF6-binding-domain.

FIG. 9A: The sequence and structural conservations at the $P_{-2}$, $P_0$ and $P_1$ positions define the major TRAF2 binding motif. These positions are occupied by the consensus sequence px(Q/E)E (SEQ ID NO: 2), where p (Pro, proline) is in lower case because it can be substituted by other medium size non polar residues (Ser, Thr, Cys, Ile) and x represents any residues. The sequence and structural conservations at the $P_{-2}$, $P_0$ and $P_3$ positions define the minor TRAF2 binding motif. These positions are occupied by the consensus sequence px(Q/E)xxD (SEQ ID NO: 4), where Pro is in lower case because it can be substituted by other medium size non polar residues (Ser, Thr, Cys, Ile) and x represents any residues.

FIG. 9B: shows consensus sequence of TRAF6 binding motif. The consensus sequence for TRAF6 binding motif extends from position −2 ($P_{-2}$) to $P_3$ and consists of pxExx(Ar/Ac) (SEQ ID NO: 12), where p (Pro, proline) is written in lower case to represent tolerance for other small to medium sized residues (for example, Ala, Ser, Thr, Ile), x can be any residues, Ar represents any aromatic residues, and Ac represents any acidic residues.

FIG. 13 shows a sequence alignment of bovine Mx1 protein (SEQ ID NO: 14) and human MxA protein (SEQ ID NO: 15). The alignment shows that there is a 77% identity in a 626 amino acid residues overlap. The alignment clearly shows that the motif PEEESE in bovine Mx1 protein corresponds to PEDENE in human MxA protein. The symbol "+" indicates the first amino acid residue of the C-terminal GED moiety of the chimeric Mx constructs: i) human N-terminal/bovine GED (huN/GEDbo) and ii) bovine N-terminal/human GED (boN/GEDhu).

FIG. 14 shows a sequence alignment of bovine Mx1 protein (SEQ ID NO: 14) and *Sus scrofa* Mx1 protein (SEQ ID NO: 16). The alignment shows that there is a 81.4% identity in a 635 amino acid residues overlap. The alignment clearly shows that the motif PEEESE in bovine Mx1 protein corresponds to PEDESG in pig Mx1 protein.

FIG. 15 shows a modified sequence of human MxA protein, in which the motif PEDENE was replaced by the bovine TRAF2/TRAF6 binding domain PEEESE; the new sequence is designated as SEQ ID NO: 17.

THE FUNCTION AND ACTIVITY OF THE PROTEINS OF THE PRESENT INVENTION

Figure 1:
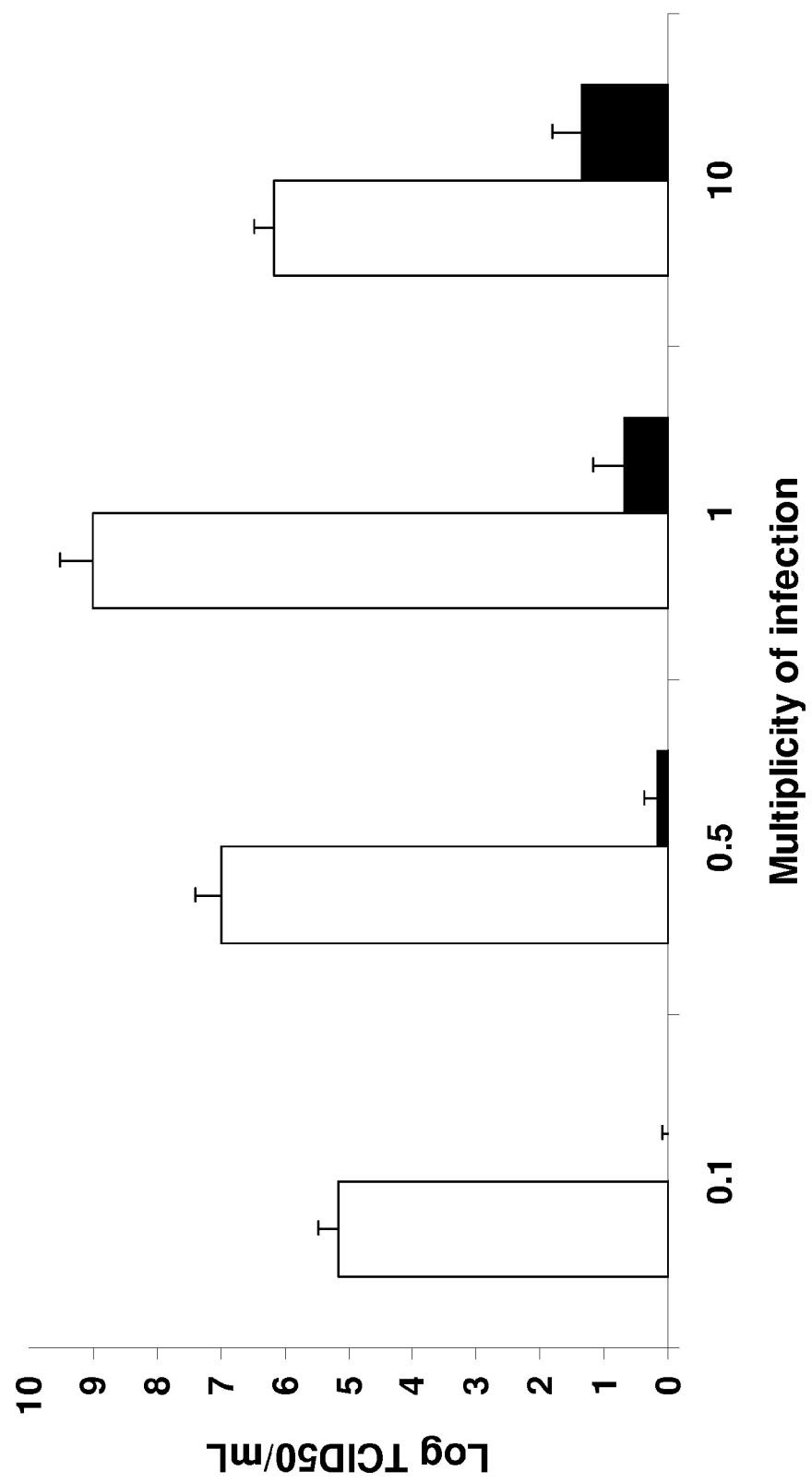
FIG. 1 shows the inhibition of influenza A/H7/N7/chicken multiplication by bovine Mx1 protein (boMx1). Pools of induced (black boxes) and non-induced (white) double transgenic Vero cells (V103) were infected with influenza A/H7N7 for 48 h. The viral titers in the culture supernatants are plotted. $TCID_{50}$, 50% tissue culture infective dose. Values are means+/−SD from 3 independent experiments.

Surprisingly, it has been found in vitro that, compared to other Mx dynamins, the *Bos taurus* Mx1 dynamin displays the most powerful anti-influenza A virus activity ever identified. Moreover, the exceptionally strong anti-influenza A virus activity exercised by this specific Mx dynamin was confirmed in vivo, thus providing the most credible molecule to use in the prevention or treatment of influenza A virus-associated diseases. As anticipated from prior art, this unprecedented antiviral activity was hypothesized to be supported by the C-terminal segment of the protein, the so-called GED.

Surprisingly, it was found that substituting the GED by that of any Mx dynamin endowed with weak anti-influenza A virus activity in the *Bos taurus* Mx1 results in a chimeric Mx dynamin still endowed with the aforedescribed exceptional antiviral activity. Conversely, grafting the *Bos taurus* GED on the backbone of a weakly anti-influenza Mx dynamin results in a still weakly anti-influenza chimeric Mx dynamin. The present invention thus provides a Mx antiviral activity enhancer that is not inserted in the C-terminal GED segment, which a person skilled in the art would not be able to predict.

The present inventors identified a novel TRAF2 and TRAF6 binding motif in *Bos taurus, Ovis aries,* and *Bubalus bubalis* Mx1 backbones that is absent from all vertebrate Mx dynamins tested so far. It was also found that Mx dynamins with this novel TRAF2/TRAF6 binding motif effectively binds TRAF2 and TRAF6 whereas Mx dynamins devoid of this novel TRAF2/TRAF6 binding motif do not. Moreover, it was also found that the presence of this novel TRAF2/TRAF6 binding motif in a Mx backbone is sufficient for driving the unprecedented anti-influenza A activity aforedescribed. In support of these findings, TRAF2/TRAF6 binding motif-deficient mutant *Bos taurus* Mx1 displays a very weak anti-influenza A virus activity. Therefore, the present invention reveals that insertion of a TRAF2 binding domain and/or insertion of a TRAF6 binding motif in a Mx dynamin is sufficient to increase its anti-influenza A activity.

The present invention makes use of wild-type and mutant Mx dynamins comprising a functional TRAF2 and/or a TRAF6 binding motif that display anti-influenza A activity superior to that displayed by the corresponding Mx dynamin backbones devoid of the activity enhancers disclosed here. A number of approaches may be utilized by a person having ordinary skill in this art to search for Mx dynamin enhancers disclosed here. For example, two representative approaches are screening of peptide libraries or synthesizing overlapping peptides from any known or yet non-identified protein endowed with TRAF2 and/or TRAF6 binding ability. In one embodiment of the present invention, the Mx dynamin activity enhancer comprises the complete or partial sequence consisting of SEQ ID NO: 69.

The present invention also makes use of wild-type and mutant Mx dynamins comprising a TRAF2 and/or a TRAF6 binding motif that display any antiviral activity superior to that displayed by the corresponding Mx dynamin backbones devoid of the activity enhancers disclosed here.

Mx antiviral activity enhancers disclosed herein may contain a TRAF2 binding motif derived from tumour necrosis factor receptor types 1 and 2 (TNFR1 and TNFR2), CD27, CD30, CD40, Ox40, LTβR, another TRAF-associated receptor (ATAR), 4-1BB, NF-kappaB-inducing kinase (NIK), latent membrane protein-1 (LMP1), and Mx1 derived from *Bos taurus, Ovis aries* or *Bubalus bubalis*. Mx antiviral activity enhancers disclosed herein may also contain a TRAF6 binding domain derived from *Bos taurus* Mx1, *Ovis aries* Mx1, *Bubalus bubalis* Mx1, CD40, Receptor Activator of NF-kappa-B (RANK), IL-1 receptor-associated kinase (IRAK1), IL-1 receptor-associated kinase 2 (IRAK2), IRAKM, receptor interacting protein-2 (RIP2), MALT1, MyD88 adapter-like protein (MAL), Toll/IL-1R domain-containing adaptor inducing IFN-beta (TRIF), human HSV1 and HSV2 herpesviruses, cercopithecine HSV1 herpesvirus, human cytomegalovirus, or human Kaposi herpesvirus. Preferably, the TRAF2 and/or TRAF6 binding domains comprises complete or partial sequence selected from the group consisting of SEQ ID No. 26-77.

Mx dynamins in which the antiviral activity enhancers disclosed herein may be naturally or artificially inserted may be derived from a number of different species. Representative dynamins include human MxA, human MxB, mouse Mx1, mouse Mx2, rat Mx1, Mx2, and Mx3, guinea pig Mx, pig Mx1 and Mx2, equine Mx1 and Mx2, chicken Mx, turkey Mx, duck Mx, rainbow trout Mx, salmon Mx, etc.

The present invention also provides methods of using the Mx antiviral activity enhancers disclosed herein to inhibit replication of influenza A viruses. Using a Mx dynamin comprising an activity enhancer disclosed herein would therefore result in reduced fatality rate, reduced disease severity, reduced cytokine production, reduced secondary infections rate and reduced viral excretion in case of a human or animal infection with an influenza A virus. Using a Mx dynamin comprising an activity enhancer disclosed herein would therefore also result in reduced genetic drift of influenza A viruses or reduced genetic reassortment between influenza A virus strains. Using a Mx dynamin comprising an activity enhancer disclosed herein would therefore also result in reduced transmissibility of influenza A virus infections, and in reduced risk of cross-species contamination.

The present invention also provides methods of using the antiviral activity enhancers disclosed herein to generate immunologically-acceptable (nonallergenic) and market-acceptable (consumer-friendly) transgenic food animals rendered resistant to influenza A virus-associated disease. The present invention also provides methods of using the antiviral activity enhancers disclosed herein to generate immunologically-acceptable (nonallergenic) and market-acceptable transgenic food animals in which transmissibility of the influenza A viruses to other animals or to humans is dramatically reduced. The phrase "immunologically-acceptable" refers to antigenic molecular entities present in meat and other animal products that were eaten by human beings since thousands of years and therefore are well known to be devoid of allergenic or similar undesired potential for humans. The phrase "market-acceptable" and "consumer-friendly" refer to exogeneous molecular entities present in meat and other animal products that would give rise to less hostility among consumers because these molecular entities are eaten by humans since ever.

The present invention also provides a method of inhibiting influenza A viruses-associated symptoms, lesions and dysfunctions, comprising the step of administering the composition of the present invention or any polynucleotide encoding for the composition of this invention to an individual. Representative means by which the composition is delivered to said individual include liposomes, a virus, or any gene delivery vector.

The present invention also provides a method of identifying new anti-influenza A virus molecules, comprising the step of generating a transgenic cell line or a transgenic animal rendered resistant to influenza A viruses by genetic insertion of the composition of the present invention or any polynucleotide coding for the composition of this invention.

The present invention also provides a method of identifying a peptide or a non-peptide molecule capable of inhibiting influenza A viruses, comprising the step of: preparing an Mx dynamin or a polypeptide comprising a TRAF2 and/or a TRAF6 binding motif and examining binding of TRAF2 or TRAF6 to said Mx dynamin or polypeptide in the presence and absence of a peptide or non-peptide molecule, wherein reduced binding in the presence of said peptide or non-peptide molecule would indicate that said peptide or non-peptide molecule is capable of inhibiting influenza A viruses. Preferably, the TRAF6 binding motif is derived from a protein selected from the group consisting of *Bos taurus* Mx1, *Ovis aries* Mx1, *Bubalus bubalus* Mx1, CD40, RANK, IRAK1, IRAK2, IRAKM, RIP2, hMALT1, MAL, TRIF, hHSV1 UL-37, hHSV2 UL-37, cercopithecine HSV1 UL-37, hCMV UL-37, and human Kaposi herpesvirus ORF-63. Preferably, the TRAF2 binding domain is derived from a protein selected from the group consisting of TNFR1, TNFR2, CD27, CD30, CD40, Ox40, LTbR, ATAR, 4-1BB, NIK, LMP1, and Mx1 derived from *Bos taurus*, *Ovis aries* or *Bubalus bubalis*. In one embodiment, the TRAF2 and/or TRAF6 binding domains comprise a sequence selected from the group consisting of SEQ ID No. 26-77.

The present invention also provides an acceptable pharmaceutical composition comprising a pharmaceutical carrier and a Mx dynamin comprising the activity enhancers disclosed herein. In one embodiment, this pharmaceutical composition comprises a Mx dynamin or a fragment thereof in which the activity enhancer has a sequence selected from the group consisting of SEQ ID No. 26-77. The phrase "acceptable pharmaceutical composition" refers to molecular entities and compositions that do not produce an allergic or similar untoward reaction when administered to a subject.

The present invention also provides an acceptable pharmaceutical composition comprising a gene therapy vector and a polynucleotide encoding for a Mx dynamin comprising the activity enhancers disclosed herein. In one embodiment, this pharmaceutical composition code for a Mx dynamin or a fragment thereof in which the activity enhancer has a sequence selected from the group consisting of SEQ ID No. 26-77. The phrase "acceptable pharmaceutical composition" refers to molecular entities and compositions that do not produce an allergic or similar untoward reaction when administered to a subject.

The present invention is further drawn to peptidic, polypeptidic, proteic or non-peptidic and non-proteic analogs of peptidic activity enhancers disclosed herein or of Mx dynamins comprising the activity enhancers disclosed herein that mimic the increased anti-influenza function of said peptidic enhancers and Mx dynamins. These analogs can serve as robust tools to establish the role of TRAF2 and/or TRAF6-mediated antiviral effects in vitro and in vivo models of viral diseases as well as serving as prophylactic and/or therapeutic agents in their own right.

The present invention is also drawn to methods of inhibiting influenza A viruses using peptidic, polypeptidic, proteic or non-proteic molecules, wherein inhibition of influenza A viruses by said molecules is subordinated to a molecular interaction between TRAF2 and/or TRAF6 and said molecules.

Production of the Proteins of the Present Invention

The peptides of the current invention can, for example, be synthesized, prepared from purified full-length proteins, or produced using recombinant methods and techniques known in the art. Although specific techniques for their preparation are described herein, it is to be understood that all appropriate techniques suitable for production of these peptides are intended to be within the scope of this invention.

Generally, these techniques include DNA and protein sequencing, cloning, expression and other recombinant engineering techniques permitting the construction of prokaryotic and eukaryotic vectors encoding and expressing each of the peptides of the invention.

The proteins may be prepared by peptide synthesis according to method described in *Biotechnology and Applied Biochem.*, 12:436 (1990) or by methods described in *Current Protocols in Molecular Biology*, Eds. Ausubel, F. M., et al, John Wiley & Sons, N.Y. (1987).

The proteins of the invention may be produced by expression of a nucleic acid encoding the protein of interest, or by cleavage from a longer length polypeptide encoded by the nucleic acid. Expression of the encoded polypeptides may be done in bacterial, yeast, plant, insect, or mammalian hosts by techniques well known in the art.

In an embodiment, the protein of the invention is obtained by cloning the DNA sequence into a Vector starting with a DNA codon for methionine inserted upstream 5' to the first DNA codon of the desired protein sequence and modifying the DNA codon corresponding to the last amino acid of a desired protein to a stop codon by mutagenesis techniques known in the art. A host cell is transformed with the modified nucleic acid to allow expression of the encoded protein.

Examples of mutagenesis techniques include, for example, methods described in *Promega Protocols and Applications*

GWde, Promega Corp, Madison, Wis., p. 98 (1891) or according to *Current Protocols in Molecular Biology*, supra.

If the protein is to be synthesized via a prokaryotic vector, the DNA sequence encoding a protein preferably does not contain a signal peptide sequence. In addition, a DNA codon for methionine (Met) is typically inserted upstream of 5' to the first DNA codon of the coding sequence.

Methods for cloning DNA into a vector and for inserting, deleting and modifying polynucleotides and for site directed mutagenesis are described, for example, in *Promega Protocols and Applications Guide*, supra. Cells or bacteria may be transfected with a vector, preferably with an expression vector, having the desired DNA sequence attached thereto, by known techniques including heat shock, electroporation, calcium phosphate precipitation and lipofection, among others. The proteins may then be extracted and purified by, for example, high pressure liquid chromatography (HPLC), ion exchange chromatography or gel permeation chromatography. However, other methods and techniques known in the art of conducting the different steps or combinations of these steps necessary to derive the peptide of this invention or equivalent steps are contemplated to be within the scope of this invention.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. U.S.A.* 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two polypeptide sequences, when optimally aligned, such as by the programs GAP or BESTFIT using default gap weights, share at least 80 percent sequence identity, preferably at least 90 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

Nucleic Acids of the Invention

Also provided herein are isolated nucleic acids that comprise DNA or RNA sequences (polynucleotides) encoding the peptides of the invention. The nucleic acids of the invention may further comprise vectors for expression of the peptides of the invention. In some embodiments the DNA may comprise cDNA sequences encoding Mx protein. It is understood by one of ordinary skill in the art that because of degeneracy in the genetic code, substitutions in the nucleotide sequence may be made which do not result in changes in the encoded amino acid sequence. Thus, "substantially identical" sequences as defined herein are included in the scope of the invention. It is further understood by one of ordinary skill in the art that both complementary strands of any DNA molecule described herein are included within the scope of the invention.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

Treatment Protocols

The method for treatment of influenza A virus-induced diseases comprises administering to a patient an influenza A virus inhibitory amount of the Mx protein of the invention. As used herein, the term "treatment" is intended to refer to the prevention, amelioration, or reduction in severity of a symptom of influenza A virus caused disease. Similarly, an influenza A virus inhibitory effective dose of a Mx protein of the invention is a dose sufficient to prevent, ameliorate, or reduce the severity of a symptom of influenza.

The proteins of the invention may be administered singly or in combination with each other or other virus, particularly influenza A virus, inhibitory agents. Typically, the proteins of the invention are administered in an amount of about 8 micrograms to 3,000 µg/kg per day, and more preferably about 20 to 1,500 µg/kg per day preferably once or twice daily. However, other amounts, including substantially lower or higher amounts, may also be administered. The proteins of the invention are administered to a human subject in need of the treatment intramuscularly, subcutaneously, intravenously, intratumorally, by any other acceptable route of administration.

Gene Therapy

Gene therapy utilizing recombinant DNA technology to deliver nucleic acids (polynucleotides) encoding Mx proteins or peptides comprising the TRAF2/6 binding domain according to the invention into patient cells or vectors which will supply the patient with gene product in vivo is also contemplated within the scope of the present invention.

Gene therapy techniques have the potential for limiting the exposure of a subject to a gene product, such as polypeptide, by targeting the expression of the therapeutic gene to a tissue of interest, such as skeletal muscle, myocardium, vascular endothelium or smooth muscle, or solid or circulating tumor cells. For example, PCT patent application publication No. WO 93/15609 discloses the delivery of interferon genes to vascular tissue by administration of such genes to areas of vessel wall injury using a catheter system. In another example, an adenoviral vector encoding a protein capable of enzymatically converting a prodrug, a "suicide gene", and a gene encoding a cytokine are administered directly into a solid tumor.

Other methods of targeting therapeutic genes to tissues of interest include the three general categories of transductional targeting, positional targeting, and transcriptional targeting (for a review, see, e.g., Miller et al. FASEB J. 9:190-199 (1995)). Transductional targeting refers to the selective entry into specific cells, achieved primarily by selection of a receptor ligand. Positional targeting within the genome refers to integration into desirable loci, such as active regions of chromatin, or through homologous recombination with an endogenous nucleotide sequence such as a target gene. Transcriptional targeting refers to selective expression attained by the incorporation of transcriptional promoters with highly specific regulation of gene expression tailored to the cells of interest.

Examples of tissue-specific promoters include a liver-specific promoter (Zou et al., Endocrinology 138:1771-1774 (1997)); a small intestine-specific promoter (Oliveira et al., J. Biol. Chem. 271:31831-31838 (1996)); the promoter for creatine kinase, which has been used to direct of dystrophin cDNA expression in muscle and cardiac tissue (Cox et al., Nature 364:725-729 (1993)); and immunoglobulin heavy or light chain promoters for the expression of suicide genes in B cells (Maxwell et al., Cancer Res. 51:4299-4304 (1991)). An endothelial cell-specific regulatory region has also been characterized (Jahroudi et al., Mol. Cell, Biol. 14:999-1008 (1994)). Amphotrophic retroviral vectors have been constructed carrying a herpes simplex virus thymidine kinase gene under the control of either the albumin or alpha-fetoprotein promoters (Huber et al., Proc. Natl. Acad. Sci. U.S.A. 88:8039-8043 (1991)) to target cells of liver lineage and hepatoma cells, respectively. Such tissue specific promoters can be used in retroviral vectors (Hartzoglou et al., J. Biol. Chem. 265:17285-17293 (1990)) and adenovirus vectors (Friedman et al., Mol. Cell. Biol. 6:3791-3797 (1986)) and still retain their tissue specificity.

Other elements aiding specificity of expression in a tissue of interest can include secretion leader sequences, enhancers, nuclear localization signals, endsmolytic peptides, etc. Preferably, these elements are derived from the tissue of interest to aid specificity.

Viral vector systems useful in the practice of the instant invention include but are not limited to adenovirus, herpesvirus, adeno-associated virus, minute virus of mice (MVM), HIV, sindbis virus, and retroviruses such as Rous sarcoma virus, and MoMLV. Typically, the nucleic acid encoding the therapeutic polypeptide or peptide of interest is inserted into such vectors to allow packaging of the nucleic acid, typically with accompanying viral DNA, infection of a sensitive host cell, and expression of the polypeptide of interest.

Similarly, viral envelopes used for packaging the recombinant constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel et al., Proc. *Natl. Acad. Sci. U.S.A.* 88:8850-8854 (1991)). In other embodiments, molecular conjugates of the instant invention can include microtubule inhibitors (WO 94/06922); synthetic peptides mimicking influenza virus hemagglutinin (Plank et al., J. Biol. *Chem.* 269:12918-12924 (1994)); and nuclear localization signals such as SV40 T antigen (WO 93/19768).

The nucleic acid can be introduced into the tissue of interest in vivo or ex vivo by a variety of methods. In some embodiments of the invention, the nucleic acid is introduced into cells by such methods as microinjection, calcium phosphate precipitation, liposome fusion, or biolistics. In further embodiments, the nucleic acid is taken up directly by the tissue of interest. In other embodiments, nucleic acid is packaged into a viral vector system to facilitate introduction into cells.

In some embodiments of the invention, the compositions of the invention are administered ex vivo to cells or tissues explanted from a patient, then returned to the patient. Examples of ex vivo administration of gene therapy constructs include Axteaga et al., *Cancer Research* 56(5):1098-1103 (1996); Nolta et al., *Proc Nad. Acad. Sci. USA* 93(6): 2414-9 (1996); Koc et al., *Seminars in Oncology* 23 (1):46-65 (1996); Raper et al., *Annals of Surgery* 223(2):116-26 (1996); Dalesandro et al., *J Thorac. Cardi. Surg.* 11(2):416-22 (1996); and Makarov et al., *Proc. Nad. Acad. Sci. USA* 93(1): 402-6 (1996).

Means of Administration

The form of the vector introduced into a host or host cell can vary, depending in part on whether the vector is being introduced in vitro or in vivo. For instance, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus, or stably introduced into the host genome through double or single crossover recombination events. Prior to introduction into a host, a vector containing the polynucleotide of the present invention can be formulated into various compositions for use in therapeutic and prophylactic treatment methods. In particular, the vector can be made into a pharmaceutical composition by combination with appropriate pharmaceutically acceptable carriers or diluents, and can be formulated to be appropriate for either human or veterinary applications.

Thus, a pharmaceutical composition can comprise one or more of the aforementioned vectors, preferably in combination with a pharmaceutically acceptable carrier. Pharmaceutically acceptable carriers are well-known to those skilled in the art, as are suitable methods of administration. The choice of carrier will be determined, in part, by the particular vector, as well as by the particular method used to administer the composition. One skilled in the art will also appreciate that various routes of administering a composition are available, and, although more than one route can be used for administration, a particular route can provide a more immediate and more effective reaction than another route. Accordingly, there are a wide variety of suitable formulations of the composition of the present invention.

A composition comprised of a vector containing the polynucleotide of the present invention, alone or in combination with other antiviral compounds, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multidose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

An aerosol formulation suitable for administration via inhalation also can be made. The aerosol formulation can be placed into a pressurized acceptable propellant, such as dichlorodifluoromethane, propane, nitrogen, and the like.

The dose administered to an animal, particularly a human, in the context of the present invention should be sufficient to induce a therapeutic response in the infected individual over a reasonable time frame. The dose will be determined by the potency of the particular vector employed for treatment, the severity of the disease state, as well as the body weight and age of the infected individual. The size of the dose also will be determined by the existence of any adverse side effects that can accompany the use of the particular vector employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a vector, alone or in combination with other antiviral agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "antiviral effective amount" or an amount necessary to achieve an "effective level" in the individual patient.

Since the "effective level" is used as the preferred endpoint for dosing, the actual dose and schedule can vary, depending on interindividual differences in pharmacokinetics, drug distribution, and metabolism. The "effective level" can be defined, for example, as the blood or tissue level desired in the patient that corresponds to a concentration of one or more vector(s) containing the polynucleotide according to the invention, which inhibits a virus, such as influenza A virus, in an assay predictive for clinical antiviral activity of chemical compounds. The "effective level" for compounds of the present invention also can vary when the compositions of the present invention are used in combination with known antiviral compounds.

One skilled in the art can easily determine the appropriate dose, schedule, and method of administration for the exact formulation of the composition being used, in order to achieve the desired "effective level" in the individual patient. One skilled in the art also can readily determine and use an appropriate indicator of the "effective level" of the compounds of the present invention by a direct (e.g., analytical chemical analysis) or indirect (e.g., with surrogate indicators of viral infection) analysis of appropriate patient samples (e.g., blood and/or tissues) or the use of reporter proteins.

The pharmaceutical composition can contain other pharmaceuticals, in conjunction with a vector according to the invention, when used to therapeutically treat influenza A virus induced disease. These other pharmaceuticals can be used in their traditional fashion. In particular, it is contemplated that an antiretroviral agent be employed. Further representative examples of these additional pharmaceuticals that can be used in addition to those previously described, include antiviral compounds, immunomodulators, immunostimulants, antibiotics, and other agents and treatment regimes (including those recognized as alternative medicine) that can be employed to treat influenza. Immunomodulators and immunostimulants include, but are not limited to, various interleukins, CD4, cytokines, antibody preparations, blood transfusions, and cell transfusions. Antibiotics include, but are not limited to, antifungal agents, antibacterial agents.

Formulations and Pharmaceutical Compositions

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human. dosage. Various considerations are described, for example, in *Goodman and Gilman's the Pharmacological Basis of Therapeutics,* 7th Edition (1985), MacMillan Publishing Company, New York, and *Remington's Pharmaceutical Sciences* 18*th Edition*, (1990) Mack Publishing Co, Easton Pa. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety in, e.g., Szoka et al. Ann. Rev. Biophys. Bioeng. 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well-known in the art. Similarly, the compositions can be delivered via a pump to a tissue of interest.

The compositions of the invention are typically administered to patients after the onset of symptoms, although treatment can also be prophylactic in some embodiments. Typically, treatment with direct administration of polypeptides is done daily, weekly, or monthly, for a period of time sufficient to reduce, prevent, or ameliorate symptoms. Treatment with the nucleic acids of the invention is typically done at intervals of several months. In some embodiments, administration of the compositions of the invention is done in utero.

The composition of the invention may also be provided in the kit as a slow-release composition such as a daily, weekly, monthly unit provided as a sponge, dermal patch, subcutaneous implant and the like in a wrapping or container as described above. In this case, the patient may release a unit of the composition from the container and applies it as indicated in the kit instructions. The composition may then be replaced at the end of the specified period by a fresh unit, and so on.

The present composition may also be administered by means of injection, as indicated above. Typically, the peptide may be administered by itself, or, for instance, in the case of a diabetic, in a composition also comprising insulin. The same is true for the slow-release forms of the composition. Similarly, the peptide of the invention may be administered in a composition that also comprises another drug.

The following examples are given for the purpose of illustrating various embodiments of the present invention and are not meant to limit the present invention in any fashion. A person skilled in the art will appreciate readily that the present invention is able to generate the objects and obtain the advantages mentioned, as well as those objects and advantages inherent herein.

EXAMPLE 1

(with FIG. 1)

Bovine Mx1 Dynamin Displays a Stronger Anti-Influenza A Activity Compared to that Previously Claimed for Other Mx Dynamins, in Vero Cells Infected with High Pathogenic H7N7 Influenza A Virus Strain In this example, the degree of resistance to influenza A virus replication conferred by conditional expression of the *Bos taurus* Mx1 isoform was sought by measuring the 48-hours influenza A virus yield produced by Vero cell monolayers either nonexpressing or expressing the said Mx1.

Generation of full-length cDNAs encoding for said Mx1—Total RNA was extracted from IFNα-stimulated (1.000 U/ml recombinant IFNα A/D, for 24 h) Madin-Darby Bovine Kidney cells with TRIzol reagent according to the manufacturer's instructions and was reverse transcribed using the ImPromII technology. Pairs of specific oligonucleotide primers were designed according to the cDNA sequences available in databases. The PCR was performed at 94° C. for 5 min, then 10 cycles of 94° C./30 s, 62° C./30 s with a +0.1° C. increment per cycle, 68° C./120 s, then 25 cycles of 94° C./30 s, 64° C./30 s, 68° C./140 s with 3 s increment per cycle, and finally 68° C. for 10 min.

Construction of expression vectors encoding for said Mx1—The PCR products were TA-ligated with pCRII-TOPO vector and transformed in *E. coli* Top10. Several cloned cDNAs were sequenced on both strands by dideoxy chain-termination method marked with BigDye, starting with M13 forward and reverse primers. The termination products were resolved and detected using an automated DNA sequencer. The HindIII/EcoRV fragments from pCRII-TOPO, containing the total span of the chosen Mx1 isoform and the correctly deduced amino acids sequence, were subcloned directionally into the mammalian expression vector pcDNA4/TO at the EcoRV site of the vector multiple cloning site (MCS) to generate the final construct. Ligation of the EcoRV site of the pcDNA4 MCS and the HindIII site of the fragment was made possible after Klenow filling of the fragment's overhang to make it blunt-ended. The recombinant plasmid was transformed into *E. coli* Top10, selected through ampicillin resistance, identified by restriction mapping, and confirmed by sequence analysis. These pcDNA4-Mx1 vectors place the Mx cDNA under the direct transcriptional control of the complete human cytomegalovirus enhancer-promoter sequence containing elements from the bacterial tetracycline resistance operon to effectively repress/derepress transcription. A similar approach was implemented to construct an expression vector for eGFP.

Generation of transgenic Vero cell clones—All Vero cell clones produced were derived from primordial cells purchased from ATCC (Vero/CCL-81) and were grown in Dulbecco's modified Eagle's medium supplemented with 10% fetal bovine serum (DMEM-10) at 37° C. in a 5% $CO_2$-95% air humidified incubator. The T-Rex technology was implemented with the aim to generate double transgenic Vero clonal lines allowing tightly regulated conditional expression of said Mx1 protein upon doxycycline treatment. Vero cells were first transfected with the expression plasmid pcDNA6-TetR (Invitrogen) by the Lipofectamine 2000 procedure according to the manufacturer's instructions. Blasticidin-resistant (10 µg/ml) transfectants were recovered after 2 weeks of selection and were cloned once by limiting dilution. Resultant clones were obtained after an additional 4-weeks duration round of blasticidin selection and their ability to control tight conditional expression was screened by examining eGFP expression after transient transfection with pcDNA4-eGFP by flow cytometry. A few clones combined intense fluorescence with (1 µg/ml), and total extinction of fluorescence without doxycycline. Cells of one of these clones (Vero/TetR1) were subsequently electroporated with pcDNA4-Mx1. Briefly, aliquots containing ~$2·10^6$ Vero/TetR1 cells in logarithmic phase of growth with 1.5 µg of pcDNA4-Mx1 linearised by ScaI were prepared in 300 µl of MEM-0. After electroporation (0.25 kV, 950 µF, 33 ms), cells were seeded in doxycycline-free DMEM-10 medium, first for 24 h without selection, then with blasticidin (10 µg/ml) and zeocin (400 µg/ml). Blasticidin/zeocin-resistant transfectants were recovered after 4 weeks of selection and cloned twice by limiting dilution.

Phenotyping of Vero cell clones—The presence and characteristics of exogenous Mx1 expression were established by immuno-blotting and -fluorescence. For Western blot analysis noninduced and induced MDBK (IFNα) and blasticidin/zeocin-resistant transfectants (doxycycline) monolayers were washed with phosphate-buffered saline (PBS) at 4° C., scraped in PBS, and pelleted by a low-speed centrifugation. Cells pellets were lysed by boiling in Laemmli's SDS-sample buffer, and aliquots representing 10 µg of total cellular protein were electrophoresed on a 10% SDS-polyacrylamide gel. Proteins were then transferred onto polyvinylidene difluoride membrane and nonspecific binding domains blocked as described previously. Blocked membranes were probed with a rabbit anti-human MXA antiserum diluted 1:2000 in PBS/0.05% Tween-20 at 37° C. for 1 hour. The blots were then washed in PBS/0.05% Tween-20 and incubated with a biotinylated goat anti-rabbit IgGs link antibody at 37° C. for 10 min. Blots were then washed sequentially in PBS and distilled water, and developed by incubation with horseradish peroxidase-streptavidin and the substrate 3-amino-9 ethylcarbazole. For immunofluorescence (on coverslips) and flow cytometry cells were fixed with 4% formaldehyde in PBS for 20 min and permeabilized in absolute methanol for 6 min at −20° C. After being blocked for 1 hr in washing buffer (1% BSA in PBS) the cells were probed for 1 hr with a cocktail of specific polyclonal guinea pig and rabbit anti-human MxA antisera and, after three washing steps, incubated for a further 1 hour with a mix of relevant secondary antibodies diluted 1:1000 and conjugated to Alexa 488. All steps were carried out at room temperature. Clones were analysed either qualitatively by epifluorescence or quantitatively in a fluorescence-activated cell scanner.

Selection of a Vero cell clone expressing said Mx1—The Mx1 expression pattern in each of a series of ~400 blasticidin/zeocin-resistant double transgenic clones was screened by immunofluorescence using the following criteria: (i) proportion of cells expressing Mx1 when grown in doxycycline-free medium, (ii) proportion of cells expressing Mx1 upon induction, and (iii) subcellular intensity of Mx1 staining. A few clones combined zero expression without doxycycline, >99% expression with, and intense cytoplasmic granular staining. These clones were characterized further using Western blotting and flow cytometry. The V103 clone synthesized a ~75-kDa protein upon induction that is recognized by the anti-human MxA antiserum and comigrates with the authentic *Bos taurus* Mx1 as judged from the bands generated by IFNα-stimulated MDBK cells, i.e. those cells from which the relevant cDNA had been extracted to construct the transgene. Upon removal of doxycycline, ectopic Mx1 remained detectable for the following 48 h, the peak mean fluorescence level being reached 24 h after removal (i.e., 48 h after incorporation). At 72 h after removal however, a significant decay had occurred, noninduced and induced cells becoming undistinguishable by flow cytometry. The pattern of ectopic Mx1 expression was shown to remain stable during 30 days of culturing, with passaging of V103 cells every 3 to 5 days as needed. Resequencing of the product of a transgene-specific RT-PCR from V103 cells extracts yielded the authentic bovine Mx1 CDS.

A highly pathogenic avian H7N7 influenza A virus (A/species/Netherlands/x/2003) was used in this study. The virus was propagated and stocks were grown into embryonating chicken eggs and their titer was determined by standard median tissue culture infectious dose assays. For infections, stock aliquots were first diluted in DMEM supplemented with 0.2% BSA. Serial dilutions were prepared extemporaneously in order to generate volume-matched inoculums with appropriate multiplicities of infection and were incorporated onto induced (doxycycline) or noninduced (vehicle) V103 cell monolayers, the target multiplicities of infection being 0.05, 0.01, 0.5 and 1. Upon infection, the inoculum was left to adsorb for 60 min at 37° C., before being removed by thoroughly washing with PBS. The cultures were then incubated at 37° C. in doxycycline-free DMEM/2. After 48 hours incubation at 37° C., culture supernatants were sampled, and the viral titers were determined in triplicate on chicken fibroblasts by standard median tissue culture infectious dose assays. All titers were calculated by the Reed-Muench method.

According to prior art, influenza A viruses assume the role of being the canonical tool to detect a putative antiviral activity of new Mx dynamin isoforms. We were able to demonstrate for the first time that the bovine Mx1 is endowed with anti-influenza activity, as judged from results gathered in FIG. 1, showing the slowing down of viral yields and the quasi-extinction of viral replication at multiplicities of infection lower than 1. The bovine Mx1 can thus henceforward be included in the group of Mx proteins with authenticated anti-influenza activity, along with human MxA, feral mouse Mx1 and Mx2, rat Mx1 and chicken Mx.

According to prior art, the anti-influenza protection factor conferred in vitro by transgenic expression of the human MxA isoform amounted to $10^1$, $5·10^2$, or $5·10^3$. Whenever the mouse Mx1 anti-influenza activity was measured in vitro in the prior art the protection factor reported always amounted to roughly $10^3$. Although the in vitro cell preparations used to examine anti-influenza activity of chicken Mx were slightly different, the protection factor reported was roughly $10^2$. In contrast, from FIG. 1, it can be seen that the protection factor given by the bovine Mx1 isoform according to the present invention varies between $10^5$ to $10^8$ depending on the multiplicity of infection. The bovine Mx1 is therefore endowed with an anti-influenza activity dramatically stronger than that of any Mx protein tested so far.

EXAMPLE 2

Figure 2:
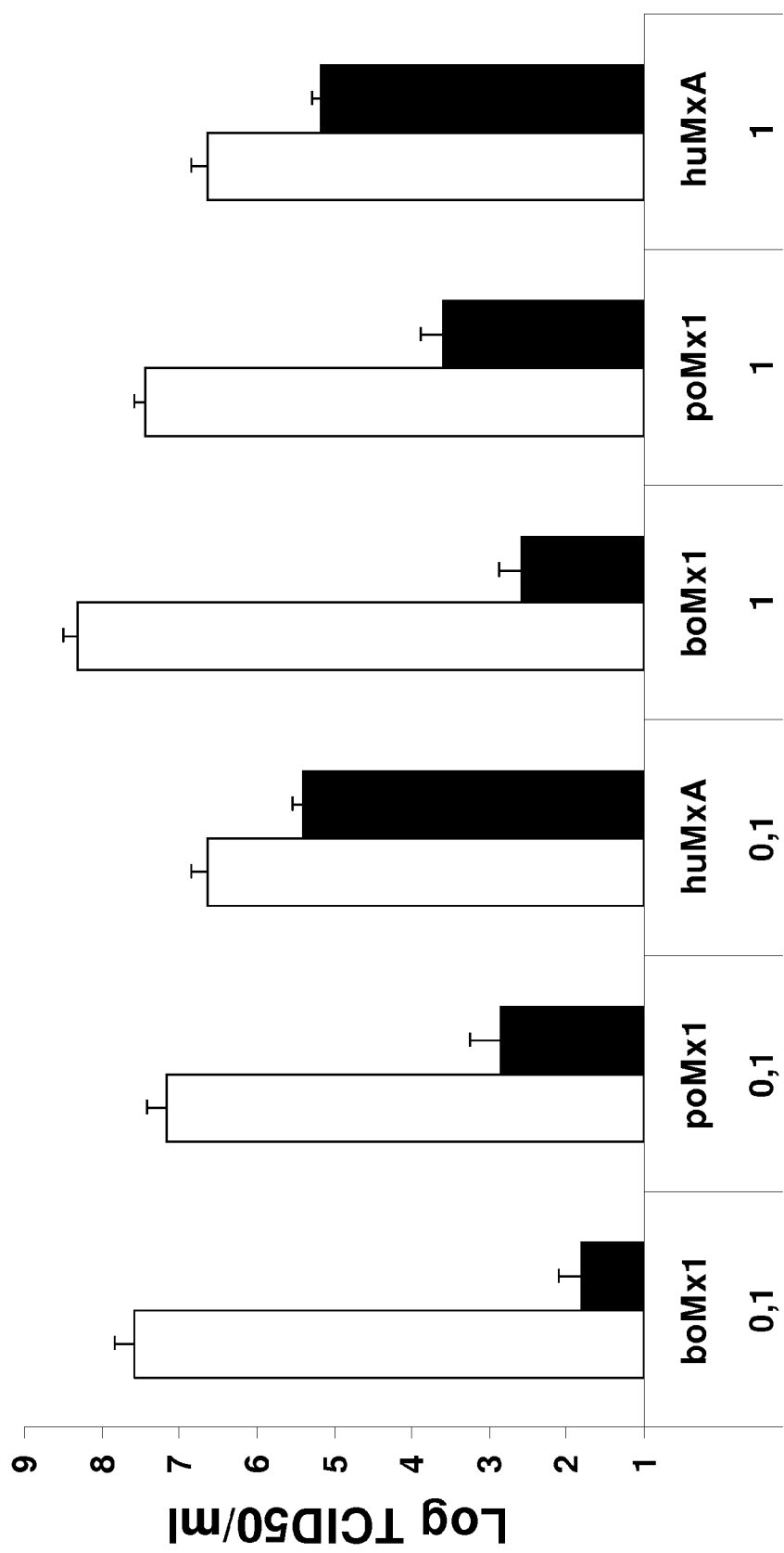
FIG. 2 shows the inhibition of influenza H5N1 multiplication by bovine Mx1 (boMx1), porcine Mx1 (poMx1) and human MxA (huMxA) proteins. Pools of induced (black boxes) and non-induced (white) double transgenic Vero cells (V103) were infected with influenza A/H5N1 for 48 h. The viral titers in the culture supernatants are plotted. $TCID_{50}$, 50% tissue culture infective dose. Values are means+/−SD from 3 independent experiments.

(with FIG. 2)

Bovine Mx1 Dynamin Displays Stronger Anti-Influenza A Virus Activity Compared to that Displayed by Porcine and Human Mx1 Dynamins, in Vero Cells Infected with High Pathogenic H5N1 Influenza A Virus Strain In this example, the degree of resistance to influenza A virus replication conferred by conditional expression of *Homo sapiens*, *Sus scofa* and *Bos taurus* Mx1 isoforms was sought by measuring the 48-hours influenza A virus yield produced by Vero cell monolayers either nonexpressing or expressing the said Mx1 isoforms. Construction of expression vectors for human MxA (huMxA) and porcine Mx1 (poMx1), generation of Vero cell clones permitting doxycycline-subordinated expression of said Mx isoforms and characterization of these clones were essentially similar to the procedures aforedescribed for bovine Mx1. One clone was obtained for each Mx isoform, namely the clones VA8 (huMxA) and VSK6 (poMx1).

A highly pathogenic avian H5N1 influenza A virus (A/crested_eagle/Belgium/1/2004) was used in this study. The virus was propagated and stocks were grown into embryonating chicken eggs and their titer was determined by standard median tissue culture infectious dose assays. For infections, stock aliquots were first diluted in DMEM supplemented with 0.2% BSA. Serial dilutions were prepared extemporaneously in order to generate volume-matched inoculums with appropriate multiplicities of infection and were incorporated onto induced (doxycycline) or noninduced (vehicle) V103, VA8 and VSK6 cell monolayers, the target multiplicities of infection being 0.1, 1, and 10. Upon infection, the inoculum was left to adsorb for 60 min at 37° C., before being removed by thoroughly washing with PBS. The cultures were then incubated at 37° C. in doxycycline-free DMEM/2. After 48 hours incubation at 37° C., culture supernatants were sampled, and the viral titers were determined in triplicate on chicken fibroblasts by standard median tissue culture infectious dose assays. All titers were calculated by the Reed-Muench method.

In the present experimental setting, in which the experimental conditions are strictly standardized, the anti-influenza activities brought by the three Mx isoforms were dramatically different (FIG. 2). In fact, influenza A virus replication was 100 to 20 000 times more repressed by expression of the bovine Mx1 than by the two others. The bovine Mx1 is therefore endowed with an anti-influenza activity dramatically stronger than that of other cytoplasmic Mx isoforms, which a person skilled in the art would not be able to predict.

EXAMPLE 3

In Vivo Mouse Models of Influenza A Virus H1N1 and H5N1 Pneumonia

Viruses—Two influenza A viruses of low pathogenicity for the laboratory mouse, a clade 1 avian H5N1 virus (A/crested_eagle/Belgium/1/2004) and a porcine H1N1 virus (A/swine/Iowa/4/1976) were used. Both viruses were first propagated in the allantoic cavity of 10-day-old embryonating hen's eggs and then adapted to the mouse by lung-to-lung passaging. At each passage, a set of mice were inoculated intranasally with 50 μl of either allantoic fluid or lung homogenate containing influenza A virus. On day 5 post-inoculation (pi), the mice were euthanized by pentobarbital overdosing followed by exsanguination, the lungs were combined and homogenized in PBS-penicillin-streptomycin, the homogenates were centrifuged at 3,000 g for 10 min, and the supernatant was used for the next passage. The process was stopped when the mice became obviously sick on and after day 3-4 pi. This occurred after 5 (H5N1) or 31 (H1N1) passages. Lung homogenates from the last passage were homogenized and aliquoted for use in pathotyping studies, and their titers determined by standard plaque (H1N1) or median tissue culture infectious dose assays (H5N1). Inoculations of serial dilutions of each adapted virus stock were then performed in FVB/J mice and the fifty-percent mouse lethal dose (MLD50) was calculated according to the method of Reed and Muench.

Pathotyping procedures—For assessment of virus-induced pathogenicity, two series of FVB/J mice were inoculated intranasally with 10 MLD50 of virus by instillation of 50 μL diluted stock. Mice were monitored daily for changes in body weight in order to assess virus-induced morbidity. At selected time intervals, a set of mice was overdosed with sodium pentobarbital and exsanguinated by cutting the brachial artery. Lungs and pieces of heart, liver, spleen, pancreas, kidney, brain, and adipose tissue from 5 mice were fixed in 4% neutral-buffered ice-cold paraformaldehyde, routinely processed, and embedded in paraffin for evaluation of histopathology. Five-micrometer sections were stained with hematoxylin and eosin or with periodic acid-Schiff for lesion detection. For virus detection, sections were stained by a streptavidin-biotin complex immunoperoxidase method. An in-house IgG-purified polyclonal rabbit antiserum raised against recombinant influenzavirus nucleoprotein was used as the source of primary antibodies and HRP-conjugated anti-rabbit IgGs were used as secondary antibodies. Peroxidase was revealed with 3-amino-9-ethyl-carbazole, resulting in a bright red precipitate, and sections were counterstained with Mayer's hematoxylin. For virus titrations, lungs from 5 mice were weighed, homogenized in 1 ml PBS, and clarified. The supernatants were used for virus titration by plaque or median tissue culture infectious dose assays. As adoption of a biphasic expiratory pattern had been shown to announce death within ~24 h, this qualitative sign was chosen, for humane reasons, to be the end-point of the experimental disease. On this end-point day, lungs from 5 mice were sampled, weighed, and their homogenates were desiccated for dry weight determination.

Characteristics of experimental influenzal diseases—The H1N1 and H5N1 influenza A virus strains used in this study were isolated respectively from a diseased pig in the US in 1976 and from a crested eagle smuggled from Thailand in 2003. Both were non-pathogenic for FVB/J mice (MLD50>$10^6$ PFU/TCID50). After adaptation, they showed a similar pathogenic outcome in FVB/J mice, i.e. very close MLD50 values: 3.2 PFUs for the H1N1 and 6.4 TCID50 for the H5N1 strain. This allowed a relevant comparison of their respective pathological signatures. Overall, virus-associated morbidity, body weight loss, and gross lesions caused by inoculation of 10 MLD50 were similar for both viruses, except that body condition and respiratory function deteriorated far more rapidly after H5N1 inoculation, end-point days being day 4 and day 8 pi for H5N1- and H1N1-induced diseases respectively. The pathological processes remained totally asymptomatic for the first 2 (H5N1) or 4 (H1N1) days and then gave rise to general signs such as gradually slower, less frequent, and more erratic spontaneous displacements and a ruffled coat. By day 3 (H5N1) or 5 (H1N1) pi, all mice became lethargic and abruptly exhibited clinical signs of respiratory disease, including respiratory distress, labored breathing, and forced expiration. After inoculation of H5N1, mice lost 10% of their body weight in 48 hours, from day 3 pi to the end-point day. After H1N1, weight loss was acute and also showed a biphasic profile: a 10% loss between virus inoculation and the appearance of respiratory symptoms and an additional 20% during ARDS. Autopsies performed on the end-point day of the H1N1 disease consistently showed the dark purplish bulky noncrepitant liver-like lungs compatible with a diagnosis of massive pulmonary congestion and consolidation. In H5N1-inoculated mice, end-point lungs were bulky, noncrepitant and diffusely pink-grayish suggesting a diagnosis of congestion with massive pulmonary edema. End-point lung wet weights were roughly doubled compared to control values, but this weight gain was achieved in only 24 hours after H5N1 inoculation (last day), whereas lung weight increased progressively over 96 hours from day 4 pi to end-point day after H1N1 inoculation (FIG. 2). The end-point dry-to-wet weight ratio of the lungs from H5N1-infected mice (17.6%±1.1%) was ~22% lower than that from the H1N1-infected mice (21.4%±1.4%). No obvious gross lesions were observed in the hearts, livers, spleens, kidneys, brains, or perivisceral fat. The time required to reach the peak virus titer was not different between virus strains. Whereas death occurred at the peak lung virus concentration for H5N1, H1N1-associated disease became fatal only 4 days after, a time at which clearance of the virus was already significant.

Some histological changes in lung morphology were identical for both viruses. Firstly, a clear topographical extension of the lesions was perceptible between the first and the last day of infection, with centrifugal spreading from the terminal bronchioles or the alveoli adjacent to the airways. Qualitatively, all of the alterations characterizing the exsudative phase of the histopathological condition termed diffuse alveolar damage were identifiable, with intense congestion of the alveolar capillaries, marginated intra-capillary neutrophils, necrosis of the alveolar epithelium, interstitial and alveolar edema, hyaline membranes, and invasion of the alveoli by (mostly) mononucleate cells. On the other hand, we observed neither cuboidalization of the alveoli (hyperplasia of type II pneumocytes), nor hyperplasia or squamous metaplasia of the airway epithelia. This is indicative of extremely rapid disease progression and/or of nearly complete elimination of type II pneumocytes. Despite these similarities, when sections of lung-tissue samples taken on the last day from the H1N1- and H5N1-infected mice were pooled, it was easy for an examiner unaware of which infection he was looking at to distinguish one from the other. The criteria for attributing the lung lesions to the H1N1 strain were: (1) earlier and much more extensive degeneration, necrosis, and desquamation of the airway epithelium, (2) a much higher cell density of the peribronchial, peribronchiolar, interstitial, and intra-alveolar infiltrates, (3) the presence of dense cuffs of mononucleate cells around the arterioles, (4) far less extensive alveolar edemas, and (5) the rarity of alveolar hemorrhages. Conversely, the lesions caused by the H5N1 strain were distinguishable by the late and only mild regressive alterations of airway epithelium, the extent of the alveolar edemas, the very low cell density of inflammatory infiltrates, the high number of alveolar hemorrhage foci, and the unusual appearance of the pulmonary arterioles, which seemed to have been dissected from the surrounding tissues because of the magnitude of the perivascular edema. On the other hand, no arteriole showed any cuff of infiltrated mononucleate cells. Some blood-vessel walls also showed hemorrhage inside the muscle layer. No other organ examined was found to carry any histopathological lesions except, remarkably, the liver in H5N1-infected mice. These livers displayed multifocal necrosis, with necrotic foci consisting of aggregates of hypereosinophilic pyknotic and caryorhectic hepatocytes admixed with a few neutrophils and lymphocytes. Such foci were also seen in the spleen of some animals. Strikingly, numerous PAS-positive islets were detected throughout the livers of H5N1-infected animals, each overlapping with a necrotic focus. Patterns of centrolobular hydropic and granular (day 2 pi), centrolobular (day 3 pi), and panlobular (day 4 pi) microvesicular fatty degeneration were also observed in the livers of all H5N1-infected animals. In their renal medulla, interstitial hemorrhages were seen.

The results of immunohistochemistry were homogeneous among mice infected with the same strain. Overall, they showed that the H1N1 strain swarmed centrifugally throughout the lungs over 4-5 days, starting from the bronchioles, but remained strictly confined to the lungs. Conversely, the H5N1 virus conquered the whole lung over 24-48 hours, infected some bronchioles only after, and spread to the liver, pancreas, kidneys, spleen, brain, and perivisceral fat.

The H1N1 virus was first detectable in the epithelium of bronchi and bronchioles on day 3 pi. By day 5, the stain was more conspicuous and appeared also in the alveolar epithelium of the areas adjacent to the airways. By day 7 pi, the virus was detectable in the epithelia of almost all bronchi and bronchioles and in the alveolar epithelium in extensive areas of the lungs. In the alveolar structures, staining revealed the virus in type I and type II pneumocytes and in alveolar macrophages.

The H5N1 virus was detectable from day 2 in some type 2 pneumocytes in peribronchiolar alveoli, some interstitial/alveolar macrophages, and some endothelial cells in the vicinity of the positive alveoli. In contrast, no non-respiratory organ examined showed any positive cells. By day 3, staining of the airway epithelium was still very discrete and limited, whereas the alveolar epithelium showed more pronounced staining diffusely distributed throughout the lung. In the liver, multiple nests of positive hepatocytes were detectable, corresponding exactly with the above-mentioned necrotic PAS-positive foci. A few renal tubular epithelial cells were also positive. On day 4 pi, the alveolar epithelium was still diffusely stained but much more pronounced than on day 3 pi. For the first time, staining of the bronchiolar epithelium was also visible, but not all bronchioles—far from all, in fact—showed this staining. Type II pneumocytes and alveolar macrophages were more often positive than type I pneumocytes. The appearance of the kidneys and liver was the same as on day 3, with more conspicuous staining. Additionally, virus-positive glial cells, splenic macrophages, cardiomyocytes, islets of Langerhans cells, and peritoneal adipocytes were also detected.

EXAMPLE 4

Modulating Mouse Innate Immunity by Expressing *Bos taurus* Mx1 Dynamin

Generation of transgenic mice carrying bovine Mx1-containing BAC305L8—The $Mx1^{-/-}$ allelic status of FVB/J mice at the Mx1 locus was first demonstrated by combining in silico comparisons of available SNP data from a series of strains (refer to the world-wide-web at informatics.jax.org), PCR amplification of the intron 10 to exon 11 junction and PCR-RFLV analysis of exon 14 using Hha1 as described (Jin et al., 1998; Vanlaere et al., 2008). The purified BAC DNA was dissolved in microinjection buffer (10 mM Tris-HCl [pH 7.5], 0.1 mM EDTA, 30 μM spermine, 70 μM spermidine, 100 mM NaCl) at a concentration of about 2-4 ng/μl and microinjected into the pronuclei of FVB/J blastocysts. These were subsequently implanted in pseudo-pregnant recipients. Screening for integration of the BAC305L8 transgene in the resulting offspring and testing for further germ line transmission (after crossing of selected animals with wild-type FVB/J) were done by DNA genotyping following PCR with *Bos taurus*-specific Mx1 primers. Eleven of 350 offspring contained at least one copy of the transgene, of which 9 proved to transmit it to the next generation. Hemi- and homozygous transgenic mice were obtained through further breeding. F6 animals were analyzed for expression and functional studies of the inserted bovine Mx genes.

Analysis of boMx1 mRNA levels—Mx1 transcript levels were compared in wild-type and transgenic mice, after a standardized stimulation (poly-I/C, 15 μg/kg ip for 24 h). Amounts of boMx1-protein-encoding mRNAs were normalized with respect to the amount of endogenous reference mRNA (encoding glyceraldehyde-3-phosphate dehydrogenase, GAPDH).

Production of cDNA samples—Brain, lung, and spleen tissues (50-100 mg) were taken from wild-type and transgenic 7- to 8-wk-old female poly-I/C-stimulated mice. Each tissue sample was individually homogenized in TRIzol for preparation of total mRNA. Each homogenate was treated with TURBO DNase (Ambion) for 30 min at 37° C. Next, line- and organ-specific total RNA extracts were produced by pooling individual extracts. After purification the purity and concentration of each extract were determined spectrophotometrically (the OD260/280 and OD260/230, respectively, were in the range 1.9→2.0 and 1.8→2.2, NanoDrop-1000/Isogen), and mRNA integrity was checked by agarose gel electrophoresis. An aliquot of each line- and organ-specific total RNA extract (2 μg RNA) was then reverse-transcribed at 50° C. for 60 min in the presence of 50 μg specific 18-mer oligonucleotide primers and Superscript III reverse transcriptase.

Production of DNA calibrators—To estimate the number of copies of each target cDNA in each sample, it was necessary to generate calibrators containing known target copy numbers. To this end, each target sequence was amplified by RT-PCR, purified, and cloned into the pCRII vector. Then stock solutions of known concentration were generated for each target, the number of copies (per ml) being calculated by dividing the plasmid concentration (μg/μl) by the mass of the plasmid (μg). For this calculation the plasmid concentration was determined by spectrometry (OD at 260 nm) and the plasmid mass was calculated by multiplying the length of the plasmid (vector length [bp]+insert length [bp]) by the mass of a nucleotide ($1.096\ 10^{-15}$ [μg]). For each target, a standard curve for quantitative PCR was constructed on the basis of 6 dilutions of the appropriate stock solution, corresponding to $5\times10^1$, $5\times10^2$, $5\times10^3$, $5\times10^4$, $5\times10^5$, and $7.5\times10^5$ copies. For comparisons between lines and organs, the number of Mx transcripts was normalized with respect to the corresponding number of GAPDH transcripts.

Real-time PCR—The PCR mixture consisted of 100 ng/μl template DNA (1 μA, 70 nM primers (0.7 μl of each), and 12.5 μl ABsolute™ Blue QPCR SYBR Green ROX Mix (ABgene) in a final volume of 25 μl. The mixture was placed in an ABI PRISM® 7900HT thermocycler and amplification was carried out under the following conditions: initial denaturation at 95° C. for 15 min, followed by 40 cycles of denaturation at 95° C. for 15 s and annealing-extension at 58° C. for 30 s, and then a final extension at 72° C. for 30 s. Amplification of all transcripts was performed in triplicate, and three independent sessions were carried out with each RNA extract. The melting curve of each amplicon was monitored by means of a swing back to 50° C., followed by a stepwise rise in temperature up to 95° C. Melting curve analysis always revealed the presence of a single product. To check for false positives, RT-free and no-template controls were run for each template and primer pair.

Analysis of boMx1 protein levels/Extraction—For each mouse line and each tissue sampled (brain, heart, kidney, liver, lung, and spleen) the frozen (−80° C.) organs from 5 poly-I/C-exposed (15 μg/g body weight 24 h before sacrifice) 8-wk-old animals were pooled and pulverized with pestle and mortar in a liquid nitrogen bath. About 500 mg crude frozen homogenate of each organ was resuspended in 600 µl extraction buffer (LLB, Eurogentec), vortexed for 2 min, and kept on ice. Samples were then sonicated (3 pulses of 30 s each with 30-s intervals on ice) and centrifuged at 11,000×g for 10 min at 4° C. The supernatants were stored at −80° C. in protein-repellant-coated tubes (Protein LoBind Eppendorf Tubes®) and total protein content was measured with the BCA Protein Assay kit.

Analysis of boMx1 protein levels/Immunoblot—Aliquots of resulting supernatants corresponding to 50 (spleen), 70 (lung), or 250 µg (brain) total protein were loaded onto 10% SDS-PAGE gels and electrophoresed. After electrotransfer onto nitrocellulose membranes, the blots were blocked for 30 min with Tris-buffered saline containing 0.1% Tween and 10% bovine serum albumin and incubated for 1 h at room temperature with the mouse antiserum (dilution 1:1,000). Immune complexes were revealed with HRP-conjugated pig anti-rabbit IgG F(ab')2 fragments (dilution 1:1,000, Dakocytomation), and peroxidase detection with the CN/DAB Substrate Kit (Pierce Biotechnology). Densitometry was performed with the Fluor S Multiimager CCD camera system and Quantity One software (Bio-Rad).

Analysis of boMx1 protein levels/ELISA—A non-competitive indirect sandwich enzyme-linked immunosorbent assay (ELISA) was developed, using in-house anti-bovine Mx1 rabbit antiserum for capture, mouse antiserum followed by HRP-conjugated polyclonal rabbit-anti-mouse-Ig for detection, and finally TMB conversion as the read-out parameter for enzyme activity. First, 96-well Microlon 600 plates were coated overnight at 4° C. with 100 µl rabbit antiserum diluted 1:1000 in carbonate buffer (100 mM, pH 9.5). They were then blocked for 1 h at 37° C. with 250 µl casein solution (1% in PBS). For boMx1 content determinations, the wells were first incubated for 1 h at 37° C. with 100 µl calibrator (see below) or with organ extract diluted in PBS, then incubated for 1 h at 37° C. with 100 µl mouse antiserum diluted 1:1000 in PBS-0.5% casein. For detection of immune complexes, the wells were incubated for 1 h at 37° C. with 100 µl rabbit anti-mouse-Ig diluted 1:1000 in PBS-0.5% casein, then incubated at room temperature for 20 min with 100 µl TMB in substrate buffer with $H_2O_2$, according to the manufacturer's recommendations. Development was stopped by adding 100 µl of 1 M HCl and the plates were read at 450 nm. The OD was determined with respect to a subtractive reference (an extract of the corresponding organ from stimulated wild-type FVB/J mice). Calibrators were derived from a stock of recombinant boMx1 titrating 100 µg/ml. The highest calibrating concentration used was 375 ng/ml, and this solution was subjected to a 9-step serial dilution in PBS. The concentrations of the resulting calibrating samples were as follows: 375, 250, 200, 150, 100, 80, 60, 40, 20, and 10 ng/ml. New calibrators were generated from the stock for each session of tissue boMx1 content measurements. They provided an absolute correlation of signal vs. concentration (ng boMx1 per µg soluble protein). Successive dilutions of primordial protein extracts from each organ were first assayed in order to determine the range of concentrations yielding the highest signal. Spleen, lung, and brain protein extracts were diluted so as to incorporate respectively ~5, ~50, and ~300 µg total protein per well.

Analysis of boMx1 protein levels/Immunohistochemistry—Tissue sampling was performed according to a standard protocol. After fixation in 4% neutral-buffered ice-cold paraformaldehyde and embedding in paraffin, tissue sections were stained for boMx1 detection by an indirect immunohistological method using the rabbit antiserum followed by an HRP-conjugated goat-anti-rabbit immunoglobulins secondary antibody. Peroxidase was revealed with 3-amino-9-ethyl-carbazole, resulting in a bright red precipitate. Tissues were counterstained with Mayer's hematoxylin and embedded in glycerol-gelatin. Rabbit pre-immunization serum, omission sections, and mock-exposed MDBK cell cytospins were used as negative controls and IFNα-exposed MDBK cell cytospins were used as positive controls. The following tissues were examined: lung, heart, intestine, liver, spleen, kidney, cerebrum, cerebellum, and brain stem.

Functional analysis of boMx proteins—Modulation of mouse innate immunity against RNA viruses by the transgene products was probed by examining whether the biological cycle of the vesicular stomatitis virus (VSV), a rhabdovirus, is altered in transgenic mouse embryonic fibroblasts (MEF). A stock and appropriate dilutions of VSV serotype Indiana were prepared from the supernatant of virus-infected BHK-21 cells. Two independent in vitro experiments were first conducted, in which viral suspensions were incorporated (300 µg/well, 24-well plates) for 1 h at a multiplicity of infection of 0.1, 1, or 10 into near-confluent (80%) cultures of noninduced or induced (50 µg/ml poly-I/C for 24 h) MEF lines derived from wild-type (WT), transgenic low-expression, and transgenic high-expression FVB/J mice. After a 1-hour adsorption period, excess inoculum was removed by washing with PBS, and the cultures were re-incubated for 24 h at 37° C. in fresh DMEM. The culture supernatants were then sampled for virus titration. For in vivo studies, sets of 15 WT, 10 ML-555, and 15 ML-549 FVB/J mice were inoculated with the virus by slowly instilling 50 µl of the viral suspension (i.e. ~$10^7$ cell culture infective dose 50% [$CCID_{50}$]) into the nostrils under anesthesia (30/5 mg·kg$^{-1}$ xylazine/ketamine ip). In all sets, body weight and survival were monitored for 14 days. Subsets of 5 WT and 5 ML-549 mice were euthanized on day 4 after inoculation. Their lungs and brains were removed and homogenized with a TissueLyser for subsequent virus titration. Viral titers from supernatants and organ suspensions were first determined in duplicate on Vero cells. They were expressed in $CCID_{50}$ units at 48 h after inoculation as previously described (Baise et al., 2004: Conditional expression of type I interferon-induced bovine Mx1 GTPase in a stable transgenic vero cell line interferes with replication of vesicular stomatitis virus. J Interferon Cytokine Res. 2004 Sep. 24 (9), pp. 513-521). Relative quantification of the viral load was also done by real-time PCR. Total RNA was extracted with the help of commercially available NucleoSpin silica-based spin-columns according to the manufacturer's instructions (Macherey-Nagel). In a separate reverse transcription (RT) step, 2 µg extracted RNA was added to 1× Multiscribe RT Buffer (TaqMan® Reverse Transcription Reagents, Applied Biosystems) supplemented with 25 pmol random hexamer primers (Applied Biosystems), 5 nmol dNTP's, 55 nmol $MgCl_2$, 4 IU RNase inhibitor; and 12.5 IU Multiscribe reverse transcriptase (Applied Biosystems) in a total volume of 10 µl. RT conditions were as follows: 10 min at 25° C., followed by 30 min at 48° C. and 5 min at 95° C. For the subsequent real-time PCR, 5 µl template cDNA was added to 12.5 µl of 2×SYBR Green PCR Master Mix (Applied Biosystems) supplemented with 5 pmol forward and reverse primers in a total volume of 25 µl. The mixture was placed in an ABI 7900HT thermocycler for 10 min at 95° C., then the targeted VSV-specific cDNA segment was amplified by means of a program consisting of 40 cycles of 15 s at 95° C. and 60 s at 60° C. The melting curve of the resulting amplicon was monitored by means of a swing back to 50° C. for 15 s, followed by a stepwise rise in temperature up to 95° C. A VSV-positive sample and a negative water sample were included as internal controls in both the RT and the PCR step. All samples were analyzed in duplicate reactions.

Characterization of transgenic mouse lines with a functional *Bos taurus* Mx1-expressing insert—SNP data available between positions 976 686 42 and 976 845 14 on chromosome 16 (Mx1 gene) do not reveal variation between the FVB/J line on the one hand, BALB/c, C57BL/6, DBA/2, and C3H/HeN lines on the other. Moreover, the genomic stretch overlapping intron 10 and exon 11 was retrieved by PCR from BALB/c-A2G mice but never from BALB/c, FVB/J and ML-549 lines. PCR-RFLV analysis of exon 14 revealed the presence of an HhaI restriction site in all strains tested, which refuted the hypothesis of a CBA/J-like Mx1$^{-/-}$ allele in FVB/J. Collectively, these results show that the FVB/J line carries the Mx1-negative allele common to the vast majority of inbred lines. Eleven mice born through oviduct transfer of microinjected oocytes were transgenic. Nine of these transmitted the transgene to their offspring, as revealed by PCR analysis, but two of the nine lines became rapidly extinct because of very low reproduction rates. Next, a more detailed analysis by standard PCR enabled us to amplify from the DNA of the seven remaining lines specific segments corresponding to the 5' and 3' ends of the boMx1 gene. This suggests that at least one intact copy of the bovine Mx1 gene was inserted in each line. Maximum levels of boMx1 mRNAs were measured in lung tissues from poly-I/C-injected mice by reverse transcription followed by real-time PCR. They were normalized against GAPDH mRNA. This analysis demonstrated efficient transcription of the inserted boMx1 gene in the lungs in all lines. The transgenic lines were readily classified as high-expression (ML-549, ML-556), medium-expression (ML-310, ML-375), or low-expression lines (ML-312, ML-545 & ML-555), according to the amount of transcripts produced. In silico translation of the boMx1 polynucleotide sequences retrieved by RT-PCR from poly-I/C-induced transgenic mice yielded the expected amino acid sequences. Western blot (immunoblot) analysis of lung, spleen, and brain (data not shown) extracts showed that boMx1 mRNA was duly translated in all three tissues. A semi-quantitative densitometric analysis of three blots, obtained from the lungs of three mice, yielded the same classification by expression level as determined by real-time RT-PCR: ML-549≈ML-556>ML-310≈ML-375>ML-312≈ML-545≈ML-555 (FIG. 2B). Immunohistochemical analysis of brain, heart, lung, intestine, kidney, liver, and spleen tissues confirmed these results and further revealed inter- and intra-organ differences in expression. In all mice of all transgenic lines but one (ML-545, whose tissues displayed no staining), boMx1-specific staining was more intense in the kidneys and intestines than in the other organs. In the brain and liver, it was more intense in some cell types (Kupffer cells) or structures (the choroid plexus); in the lungs, staining was more intense in the epithelium of the alveoli than in the epithelium of the bronchioles. We used an ELISA to measure the concentration of boMx1 protein in various organs of 5 poly-I/C pretreated mice of each line. For line ML-545, whatever the animal or the organ, the results were the same as for the organs of wild-type mice. Among the six boMx1-producing lines, no clear expression pattern emerged, although the dominant trend was for the concentration to be about 15 times as high in the spleen as in the lungs and about 5 times as high in the lungs as in the brain. In the lungs, four lines displayed concentrations of 200-300 and the other two about 100 ng per mg soluble protein. On the basis of concentrations in the brain, three pairs were identifiable: ML-549 and ML-556 with about 50, ML-310 and ML-375 with 15-25, and ML-312 and ML-375 with about 5 ng per mg soluble protein. With regard to spleen concentrations, there emerged 2 high-expression (~5 μg/mg soluble protein), 2 low-expression, and 2 no-expression lines. Among the latter is line ML-310, with high boMx1 levels in the lungs and none in the spleen. Upon maximum stimulation by poly-I/C, fifth-passage embryonic fibroblasts from ML-549 and ML-555 mice expressed about 1.4 and 0.2 μg boMx1 per mg of soluble protein. Our stably transfected Vero cell line, which shows a high degree of VSV resistance (Baise et al., 2004), contains about 1 μg/mg, and the bovine BT and MDBK cell lines produce ~1 and ~0.6 μg/mg respectively. For comparison we also conducted a large-scale screening of the boMx1 content of bovine spleens collected at a local slaughterhouse and at the Faculty necropsy clinic. This revealed spontaneous (thus submaximal) concentrations of ~0.15 μg/mg soluble protein among slaughtered animals and among necropsied animals in which no viruses were detected, whereas boMx1 concentrations amounted between 0.5 and 3 μg/mg among the 10 virus-positive cases. In summary, transgenic mice were produced that lack endogenous antiviral Mx proteins (their genetic background is that of the FVB/J strain) but that conditionally express the bovine Mx1 gene, in various organs and under the control of their natural promoter, up to protein concentrations comparable to those measured in bovine cells and tissues.

Transgenic mice expressing the intact *Bos taurus* Mx1 gene are protected against lethal VSV infection—Using weight loss as a measure of morbidity, we then examined whether the bovine Mx1 gene could protect transgenic mice against lethal VSV infection. We observed that at ~10$^7$ CCID$_{50}$ of the virus, transgenic boMx$^{+/-}$ ML-549 mice did not experience any significant weight loss, whereas transgenic boMx$^{+/-}$ ML-555 and wild-type mice lost significant body weight after inoculation. Follow-up of survival among these mice revealed highly significant differences between ML-549 mice, on the one hand, and ML-555 and wild-type mice on the other (Kaplan-Meier analysis, p<0.01); all ML-549 mice survived whereas the mortality rate was 100 and 70% among the two other lines respectively. In summary, mice expressing both bovine Mx1 were protected against the high mortality and morbidity caused by the VSV virus. To test hypothesis that this boMx1-induced reduction in clinical severity was associated with repression of the virus itself, we quantified VSV viral loads by qPCR and conventional titration. Four days post-VSV infection, VSV genomic loads were significantly higher in the lungs of wild-type mice than in ML-549 mice, as judged from the increased cycle threshold in samples from the latter. The brain is another target organ for VSV following intranasal infection. On day 4 post infection, the VSV genome was retrieved from 100% of the wild-type but only 50% of the ML-549 mice, and a comparison of the qPCR-positive samples revealed a lower level in ML-549 mice. We also measured replication of VSV in the lung and brain tissues of the mice 4 days after inoculation. The virus titers found in the brains of all mice were below the limit of detection of our assay at this time point. The virus was detected in the lungs of all wild-type mice (4.17±0.65[−1] log TCID$_{50}$), but never in the lungs of the transgenic mice. Overall, expression of the bovine Mx1 gene in mice was thus crucial to reducing the viral load in lungs after VSV infection. Twenty-four hours after infection of embryonic fibroblast monolayers with VSV, both the genome copy number and the infectious particle load were again dramatically lower in ML-549 than in wild-type-derived cells.

EXAMPLE 5

Generation of *Mus musculus* and *Bos taurus* Mx1-Expressing Embryonic Mouse Fibroblasts Primary mouse embryonic fibroblasts (MEF) from congenic BALB/c-A2G and ML549, ML-555 and ML556 transgenic mice were harvested from 14-day-post-coitum embryos. First the head, liver, and intestine were dissected and the remaining fetal tissues were minced and rinsed in PBS. Fetal homogenates were then treated with trypsin (0.25% in Dulbecco's PBS), incubated for 30 min at 37° C., and subsequently dissociated in medium. After removal of perceptible tissue clumps, the remaining cells were plated out in a 25-cm² flask containing DMEM supplemented with 10% heat-inactivated FCS, 1% (v/v) penicillin-streptomycin, and 0.5% amphotericin B. After a 4-h incubation, nonadherent cells were eliminated by gentle mixing, directly followed by medium replacement. Primary cultures reached confluence after ~60 h and were split 1:2 for freezing in liquid nitrogen (passage 1 MEFs) or for plating out in 175-cm² flasks. For semi-continuous culturing, MEF cultures were split 1:4 approximately every 4 days.

EXAMPLE 6

Figure 3:
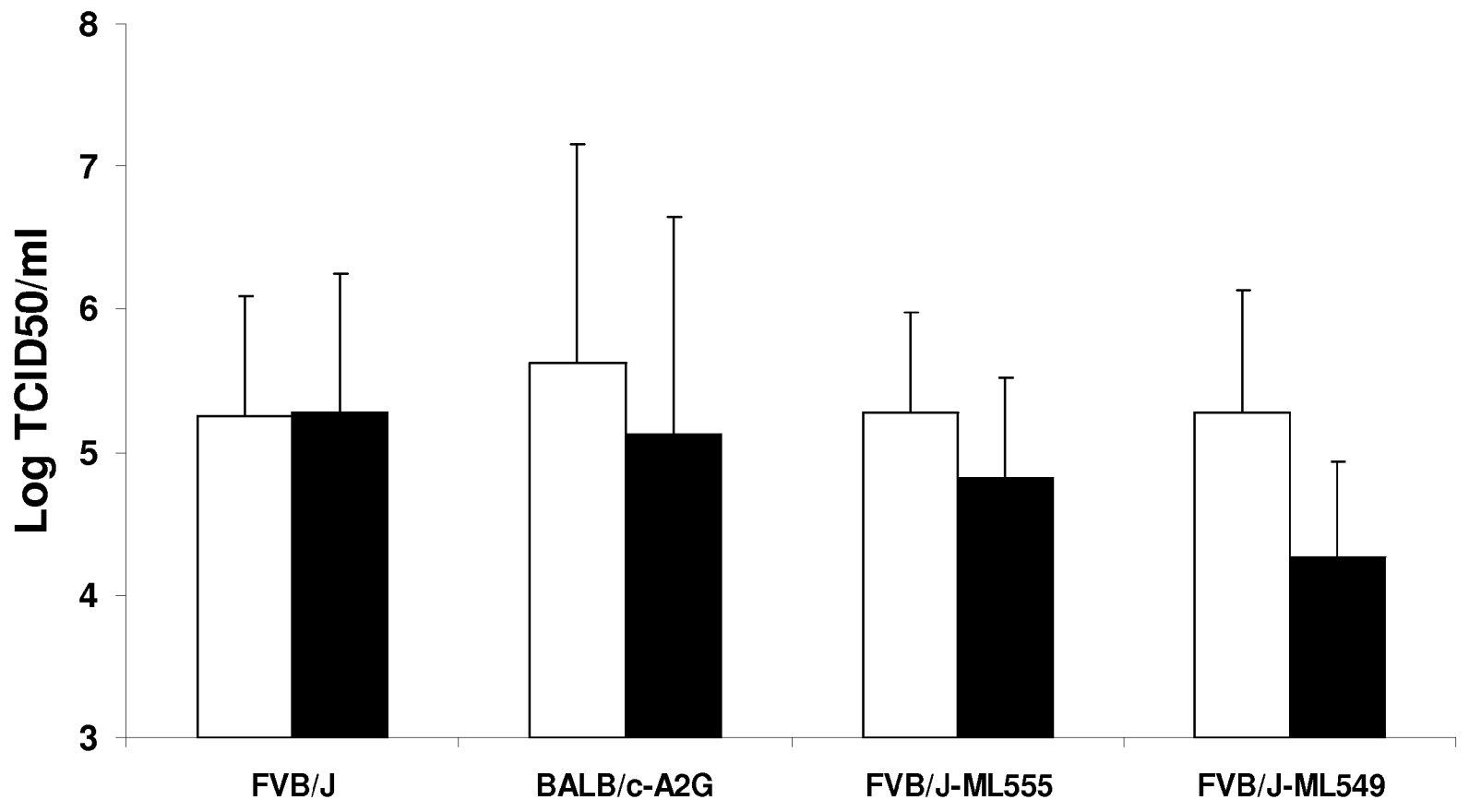

(with FIG. 3)

Bovine Mx1 Dynamin Displays Stronger Anti-Influenza A Virus Activity Compared to that Displayed by moMx1 Dynamin, in Mouse Embryonic Fibroblasts Infected with High Pathogenic H5N1 Influenza A Virus Strain Monolayers from primary embryonic fibroblasts derived from homozygous congenic BALB/c-A2G and transgenic boMx1-expressing ML555, ML549 and ML556 mouse lines were stimulated with poly-I/C 24 hours before inoculation with the A/crested_eagle/Belgium/1/2004 H5N1 strain of influenza A virus at a multiplicity of infection of $10^{-1}$. The 48-hours post-inoculation supernatants were used for virus titration by standard median tissue culture infectious dose assays. Results are gathered in FIG. 3. Compared to mouse-Mx1-expressing MEFs, those expressing physiological levels of boMx1 (derived from transgenic ML549 line) conferred a dramatically better protection, with a ~19% drop. Furthermore, physiological levels of mouse Mx1 appear to confer a degree of resistance to viral replication quantitatively similar to that conferred by MEFs derived from the ML555 line, i.e. a line previously shown to express a tenth of the amount of Mx1 expressed in the species of origin. These results show that the blockade of the virus lifecycle by boMx1 is, by far, stronger than that conferred by mouse Mx1.

According to prior art, the anti-influenza protection factor conferred in vitro by expression of human MxA amounted to $10^1$, $5 \cdot 10^2$, or $5 \cdot 10^3$, that of the mouse Mx1 to $10^3$ and that of chicken Mx to $10^2$. Thus, the protection conferred by the bovine Mx1 is unprecedented.

EXAMPLE 7

Figure 4:
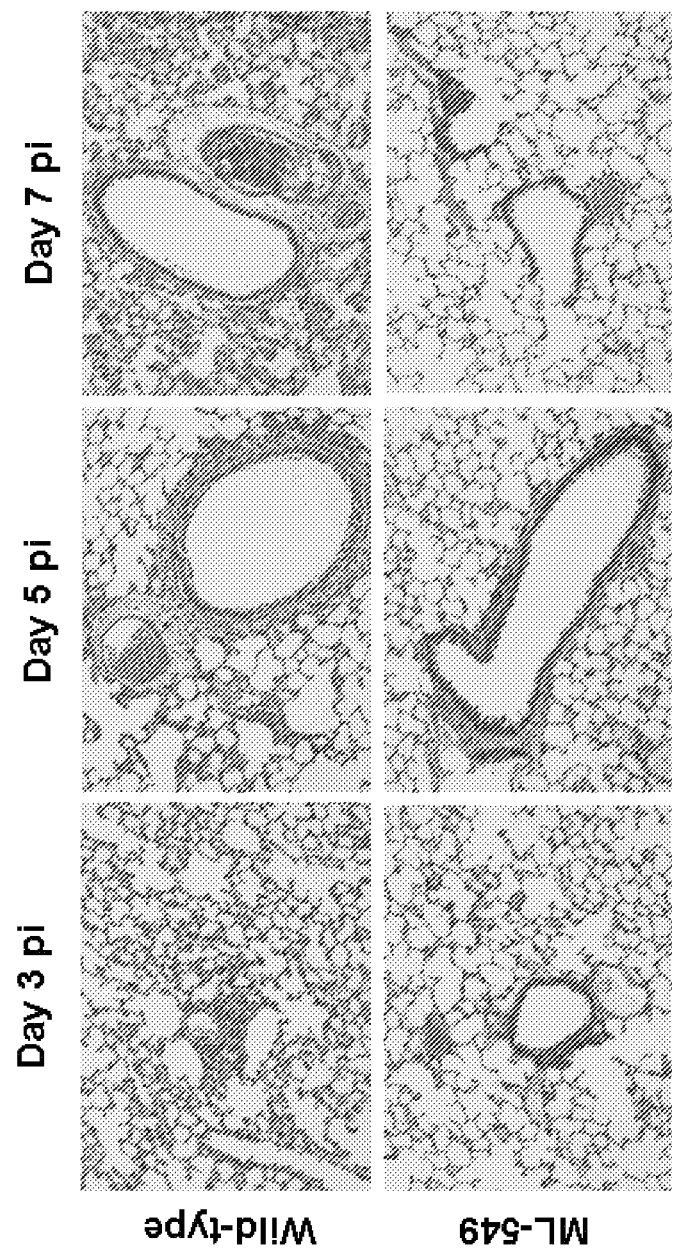
FIG. 4 shows that the expression of bovine Mx1 in vivo suppresses histological alterations caused by influenza A virus H5N1 infection in the laboratory mouse (wild type: FVB/J or transgenic mice of ML-549 line expressing bovine Mx1). The figure shows lungs of the respective mice fixed in paraformaldehyde and embedded in paraffin. Five-micrometer sections were stained with hematoxylin and eosin. Autopsies in wild-type FVB/J mice showed bulky, noncrepitant and diffusely pink-grayish lungs suggesting a diagnosis of congestion with massive pulmonary edema. Conversely, lungs from boMx1-expressing mice did not exhibit any alteration compared from lungs sampled in healthy specific-pathogen-free FVB/J mice. Histologically, the lungs from transgenic mice resembled lungs from healthy mice.

(with FIG. 4)

Expression of Bovine Mx1 In Vivo Suppresses Histological Alterations Caused by Influenza A Virus H5N1 Infection in the Laboratory Mouse A clade 1 avian H5N1 virus (A/crested_eagle/Belgium/1/2004) was propagated in the allantoic cavity of 10-day-old embryonating hen's eggs and then adapted to the mouse by lung-to-lung passaging. At each passage, a set of mice were inoculated intranasally with 50 μl of either allantoic fluid or lung homogenate containing influenza A virus. On day 5 after inoculation, the mice were euthanized, their lungs were combined and homogenized in PBS-penicillin-streptomycin, the homogenates were centrifuged, and the supernatant was used for the next passage. The process was stopped when the mice became obviously sick on and after day 3-4 occurred after 5 passages. Lung homogenates from the last passage were homogenized and aliquoted for use in further pathotyping studies, and their titers determined by standard median cell culture infectious dose assays (CCD50). For assessment of virus-associated lesions, inoculations of a standard dilution of the adapted virus stock were performed in wild-type FVB/J and in transgenic mice of the ML-549 line by slowly instilling 50 μL of each dilution into the nostrils under anesthesia (30/5 mg·kg$^{-1}$ xylazine/ketamine ip). At selected time intervals, 5 mice were overdosed with sodium pentobarbital and exsanguinated by cutting the brachial artery. Lungs were fixed in 4% neutral-buffered ice-cold paraformaldehyde, routinely processed, and embedded in paraffin for evaluation of histopathology. Five-micrometer sections were stained with hematoxylin and eosin.

Autopsies performed on the end-point day of the H5N1 disease in wild-type FVB/J mice consistently showed bulky, noncrepitant and diffusely pink-grayish lungs suggesting a diagnosis of congestion with massive pulmonary edema. Conversely, lungs from boMx1-expressing mice did not exhibit any alteration compared from lungs sampled in healthy specific-pathogen-free FVB/J mice. Histologically, the lungs from transgenic mice resembled lungs from healthy mice (FIG. 4). Conversely, in wild-type FVB/J mice many alterations were seen and a clear topographical extension of the lesions was perceptible between the first and the last day of infection, with centrifugal spreading from the terminal bronchioles or the alveoli adjacent to the airways (FIG. 4). Qualitatively, all of the alterations characterizing the exsudative phase of the histopathological condition termed diffuse alveolar damage were identifiable, with intense congestion of the alveolar capillaries, marginated intra-capillary neutrophils, necrosis of the alveolar epithelium, interstitial and alveolar edema, hyaline membranes, and invasion of the alveoli by (mostly) mononucleate cells. On the other hand, we observed neither cuboidalization of the alveoli (hyperplasia of type II pneumocytes), nor hyperplasia or squamous metaplasia of the airway epithelia. This is indicative of extremely rapid disease progression and/or of nearly complete elimination of type II pneumocytes. The pulmonary arterioles seemed to have been dissected from the surrounding tissues because of the magnitude of the perivascular edema and some blood-vessel walls also showed hemorrhage inside the muscle layer.

According to prior art, the protection conferred against the development of lung lesions upon infection with a highly virulent influenza A virus by an Mx protein is never complete, including in mice expressing their endogeneous antiviral isoform. Thus, the absence of lung alterations observed in boMx1-expressing mice is unprecedented, which a person skilled in the art would not be able to foresee.

EXAMPLE 8

Figure 5:
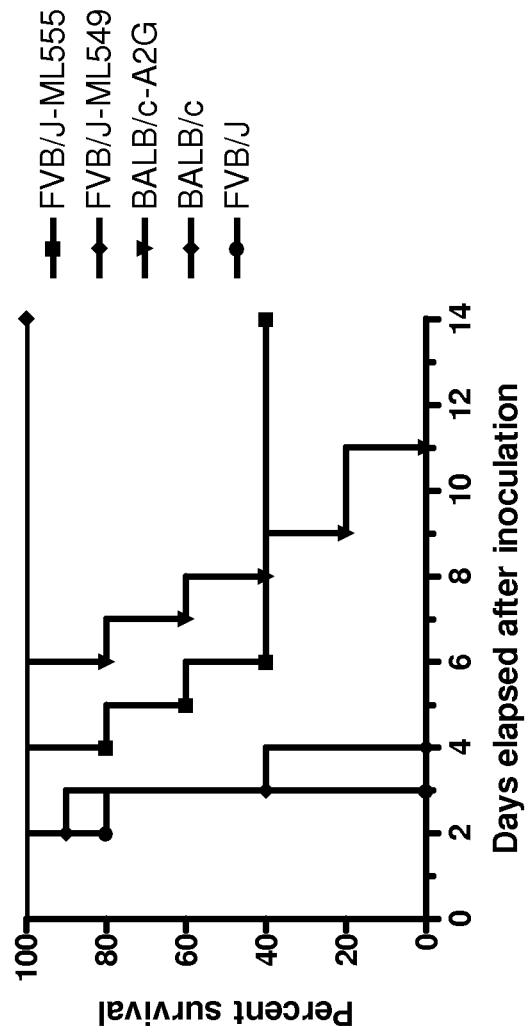
FIG. 5 shows the Kaplan-Meyer survival analysis. Mice were inoculated intranasally with 40 000 $TCID_{50}$ of influenza A virus H5N1 strain on day 0. The genotype of BALB/c-A2G is $Mx1^{+/+}$. Mouse strain FVB/J has genotype $Mx1^{-/-}$. Mice FVB/J-ML555, FVB/J-ML549 express bovine Mx1 at low and high level, respectively.

(with FIG. 5)

Influenza A Virus H5N1 Infection of the Laboratory Mouse Results in Less Mortality Among boMx1-Dynamin-Expressing Mice than Among moMx1-Dynamin-Expressing Mice A clade 1 avian H5N1 virus (A/crested_eagle/Belgium/1/2004) was propagated in the allantoic cavity of 10-day-old embryonating hen's eggs and then adapted to the mouse by lung-to-lung passaging. At each passage, a set of mice were inoculated intranasally with 50 μl of either allantoic fluid or lung homogenate containing influenza A virus. On day 5 after inoculation, the mice were euthanized, their lungs were combined and homogenized in PBS-penicillin-streptomycin, the homogenates were centrifuged, and the supernatant was used for the next passage. The process was stopped when the mice became obviously sick on and after day 3-4 occurred after 5 passages. Lung homogenates from the last passage were homogenized and aliquoted for use in further pathotyping studies, and their titers determined by standard median cell culture infectious dose assays (CCD50). For assessment of virus-associated lethality, inoculations of six ten-fold serial dilutions of the adapted virus stock were performed in wild-type FVB/J and BALB/c mice, in congenic BALB/c-A2G mice and in transgenic mice of the ML-555 and ML-549 lines by slowly instilling 50 μL of each dilution into the nostrils under anesthesia (30/5 mg·kg$^{-1}$ xylazine/ketamine ip). In all sets, survival was monitored for 14 days. The median mouse lethal dose (MLD50) was calculated according to the method of Reed and Muench.

The characteristic LD50 of the five cohorts of mice are the following: 6.4, 20, 12 649, 27 252 and >40 000 CCID50 for FVB/J, BALB/c, BALB/c-A2G, FVB/J-ML555 and FVB/J-ML549 respectively. Inoculation of 4·10$^4$ CCID50 yields clear differences between mouse strains expressing different Mx isoforms/quantities (FIG. 5). FVB/J and BALB/c survival curves are statistically similar (log-rank test, p>0.1) but dramatically differ from those typical of the three Mx-expressing lines (p<0.003). In spite of the fact that congenic BALB/c-A2G and transgenic FVB/J-ML549 mice express physiological levels of mouse and bovine Mx1 respectively, their survival curves are significantly different (p<0.002), showing that bovine Mx1 is endowed with stronger anti-influenza activity. Finally, survival curves typical of low-expressing transgenic FVB/J-ML-555 and congenic BALB/c-A2G were not statistically different (p>0.6), thus showing that a small quantity of bovine Mx1 is sufficient to mimic anti-influenza activity exercised by physiological levels of mouse Mx1.

EXAMPLE 9

Figure 6:
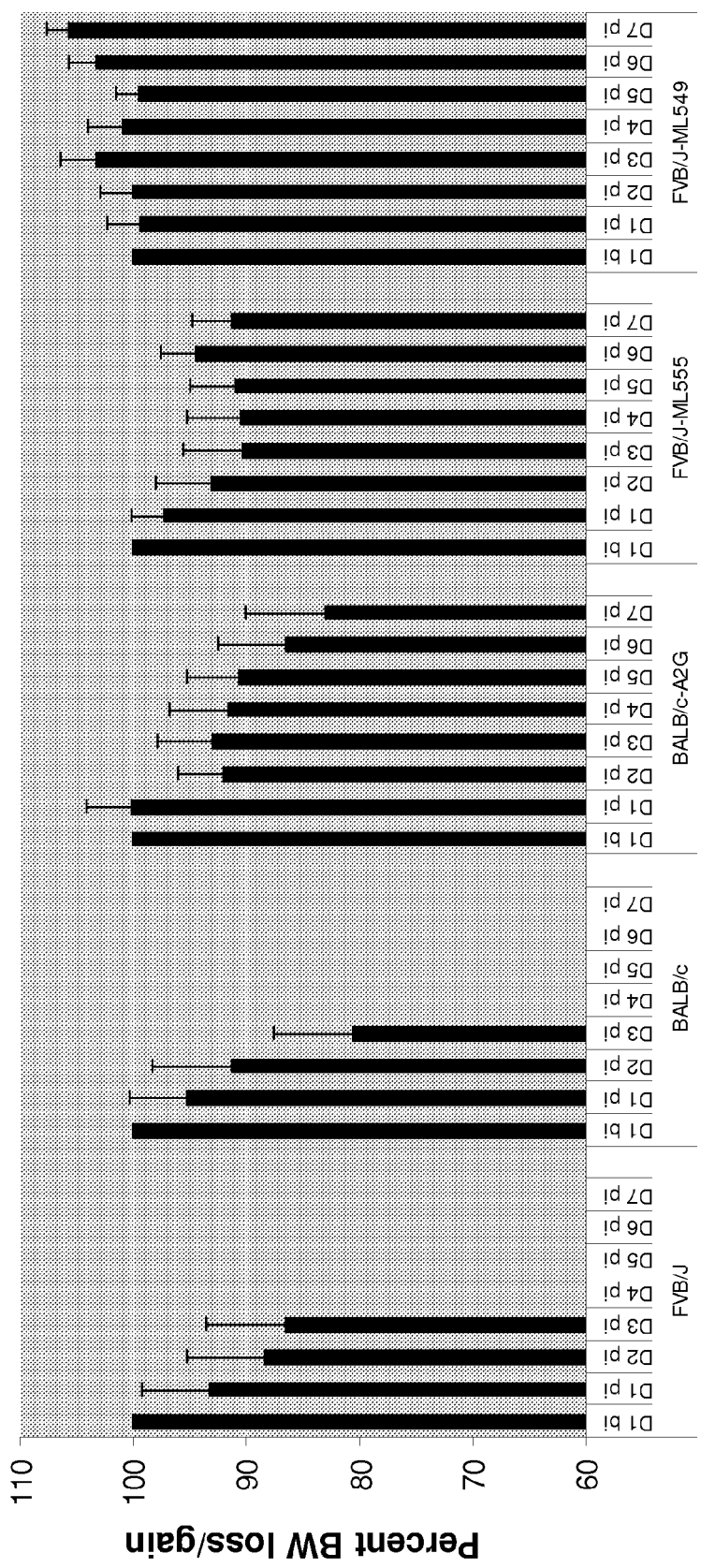
FIG. 6 shows the percentage of body weight loss or body weight gain of different mouse strains after intranasal inoculation with H5N1.

(with FIG. 6)

Influenza A Virus H5N1 Infection of the Laboratory Mouse Results in Less Morbidity Among boMx1-Dynamin-Expressing Mice than Among moMx1-Dynamin-Expressing Mice For assessment of H5N1 influenza A virus-associated morbidity, intranasal inoculations of 4·10$^4$ CCID50 of the adapted virus stock were performed in wild-type FVB/J and BALB/c mice, in congenic BALB/c-A2G mice and in transgenic mice of the ML-555 and ML-549 lines, and their body weight loss or gain were monitored daily for 1 week (FIG. 6).

Body condition deteriorated far more rapidly among Mx-negative strains (FVB/J and BALB/c), culminating with a 13-to-19 percent body weight loss; Mx-negative strains typically showed a median survival duration of 3 days. Conversely, no significant body weight loss occurred among mice of the transgenic line FVB/J-ML-549. Again, the two remaining strains showed an intermediary profile, with a continuous decrease of body weight among congenic BALB/c-A2G mice culminating with a ~15% loss 7 days after inoculation and a bimodal profile for low-expressing transgenic mice, with a continuous decrease for 5 days (minus 10%) and a trend to recovery after. These morbidity profiles are compatible with a complete, partial and absent protection of body condition by respective Mx1 isoforms. Comparison of the two mouse lines expressing physiological levels of mouse and bovine Mx confirm survival data and emphasize the superiority of bovine Mx1 in terms of anti-viral activity.

EXAMPLE 10

Figure 7:
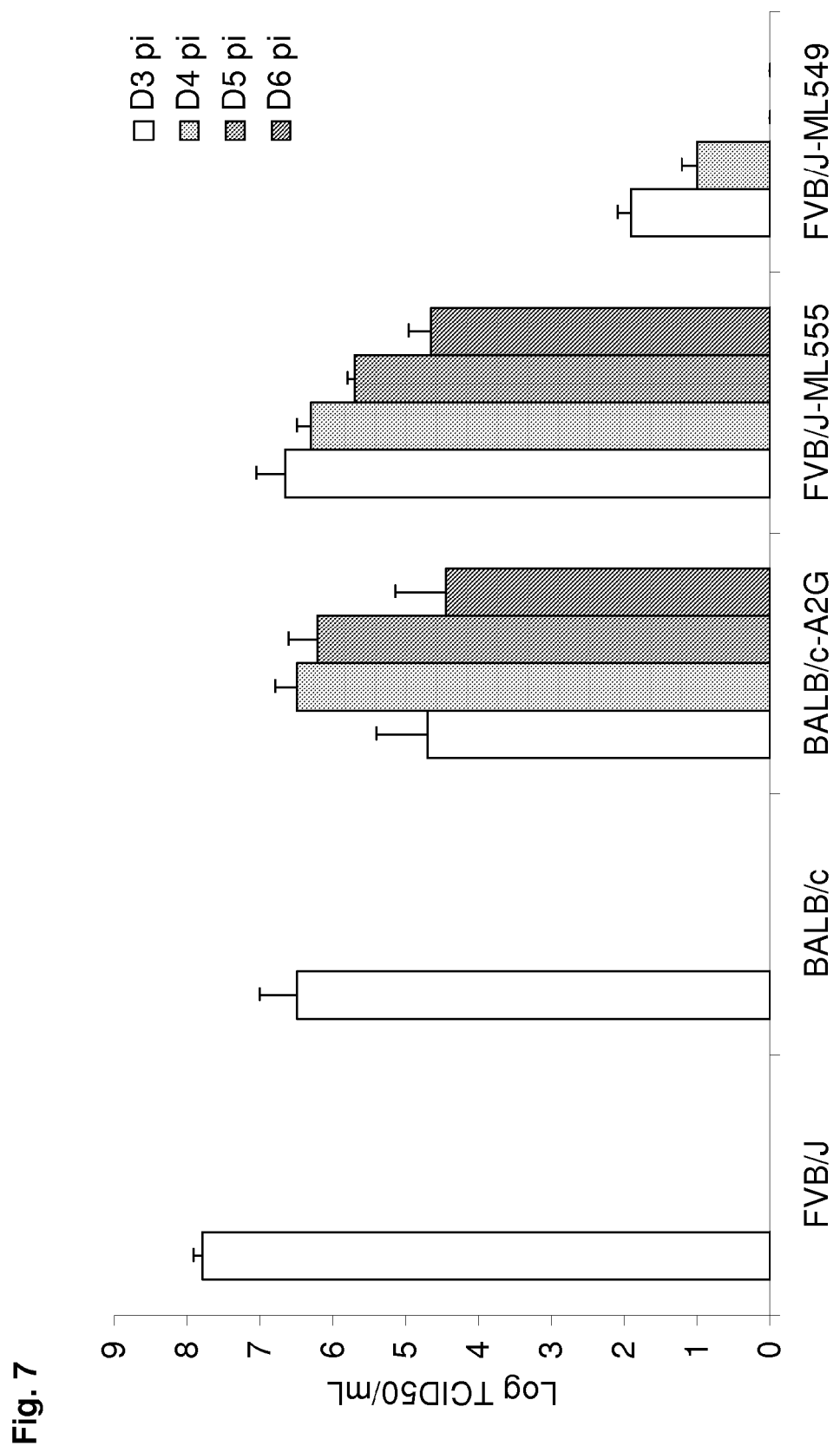
FIG. 7 shows that bovine Mx1-expressing mice (FVB/J-ML555 and FVB/J-ML549) have lower lung virus loads than mice expressing murine Mx1 (BALB/c-A2G) after intranasal inoculations with H5N1 virus strain.

(with FIG. 7)

Influenza A Virus H5N1 Infection of the Laboratory Mouse Results in Lower Lung Virus Loads Among boMx1-Expressing than Among moMx1-Expressing Mice For assessing H5N1 influenza A virus replication rate in mouse lungs, intranasal inoculations of 4·10$^4$ CCID50 of the adapted virus stock were performed in wild-type FVB/J and BALB/c mice, in congenic BALB/c-A2G mice and in transgenic mice of the ML-555 and ML-549 lines, and the lung virus titers were determined daily from three days post-inoculation (pi) until six days pi (FIG. 7). For titrations, lungs from 5 mice were homogenized in 1 ml PBS and clarified. Supernatants were used for virus titration by standard median cell culture infectious dose assays.

To test the hypothesis that Mx-associated patterns of survival and morbidity were correlated with repression of the virus itself, we quantified H5N1 lung viral loads by conventional titration. Three days after inoculation, lung H5N1 infectious particles loads were dramatically lower in FVB/J-ML549 transgenic mice compared to any other strain/line. Furthermore, the virus was cleared by day 5 pi in these mice, a time point at which the lungs of BALB/c-A2G were still heavily loaded. Overall, expression of bovine Mx1 thus strongly inhibit H5N1 influenza A virus replication, allowing abortion of the infection after 4 days, which is not the case with mouse Mx1.

EXAMPLE 11

Figure 8:
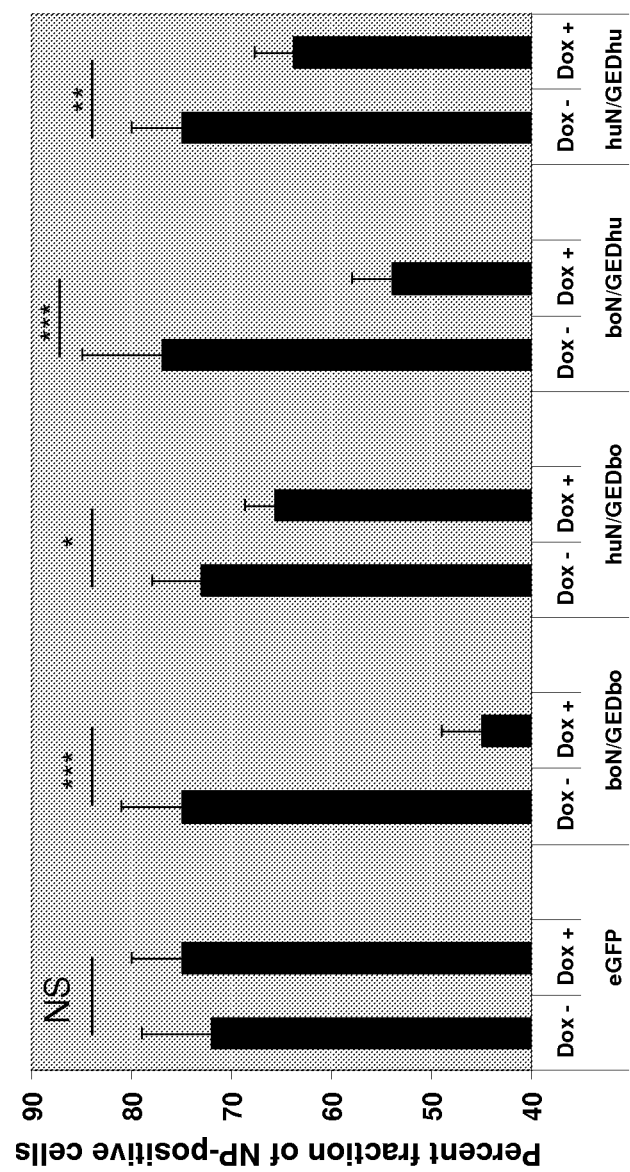
FIG. 8 shows that the N-terminal segment of bovine Mx1 exacerbates the anti-influenza activity of both human and bovine Mx GEDs. Chimeric Mx1 proteins were produced having N-terminus of human Mx1 and bovine C-terminus (GED domain): huN/GEDbo; having N-terminus of bovine Mx1 and human C-terminus (GED domain): boN/GEDhu. boN/GEDbo define wild-type bovine Mx1 and huN/GEDhu define wild-type human Mx1 (MxA). Vero cells were transfected with DNA encoding the respective constructs and the cells were examined for Mx protein and influenza nucleoprotein (NP). The figure shows the percentage of NP (influenza nucleoprotein)-positive cells. Dox− refer to noninduced cells not expressing the respective Mx-construct whereas Dox+ refer to induced cells expressing the respective Mx construct. The results show that the N-terminal segment of bovine Mx1 dramatically enhances the GED-dependent anti-influenza activity.

(with FIG. 8)

The N-Terminal Segment of Bovine Mx1 Enhances Anti-Influenza Activity of Both Human and Bovine Mx GEDs Expression Plasmids Expression plasmids encoding for chimeric bovine/human (huN/GEDbo) and human/bovine (boN/GEDhu) Mx proteins were constructed from aforedescribed pcDNA4-boMx1 and pcDNA4-huMxA by overlap extension PCR according to Wurch et al. (1998) and Nagy et al. (1996) (Wurch et. al.: A modified overlap extension PCR method to create chimeric genes in the absence of restriction enzymes. Biotechnology Techniques, 12:653-657, 1998.; Nagy et al.: Assembling and cloning genes for fusion proteins using reverse transcription one-step overlap extension PCR method. Anal Biochem 2006, 351: 311-313.), using the following primer pairs: (i) 5'-CGCAAATGGGCGGTAGGCGTG-3' (SEQ ID NO: 18) and 5'-ACTGGAAAGCCCCAAAAT-3' (SEQ ID NO: 19) for producing the N-terminal fragment of human MxA, (ii) 5'-CCTCGACTGTGCCTTCTA-3' (SEQ ID NO: 20) and 5'-AGAGAAGGAGCTGGAAGAAG-3' (SEQ ID NO: 21) for producing the GED-encoding fragment of human MxA, (iii) 5'-CGCAAATGGGCGGTAGGCGTG-3' (SEQ ID NO: 22) and 5'-GGATTGGAAGTAATGGTTTG-3' (SEQ ID NO: 23) for producing the N-terminal fragment of bovine Mx1 and (iv) 5'-CCTCGACTGTGCCTTCTA-3' (SEQ ID NO: 24) and 5'-AGAGAAGGAGGCAGAAGAAG-3' (SEQ ID NO: 25) for producing the GED-encoding fragment of bovine Mx1.

Transduction and Infection of Vero Cells

Transfection was performed according to the Transfectin technology, essentially as described by the manufacturer, using a transfection mixture consisting of 50 µl MEM, 1 µl Transfectin and 50 µl MEM to which 0.75 µg of each plasmid DNA had been incorporated (pcDNA4/TO-eGFP as control, pcDNA4-huMXA, pcDNA4-boMX1, pcDNA4-boN/GEDhu, pcDNA4-huN/GEDbo and pcDNA4/eGFP as experimental groups. Briefly, Vero cells were seeded in 24-well plates and grown overnight to 70%-80% confluency. Then, cells were washed three times with phosphate-buffered saline (PBS), medium was replaced with 200 µl MEM per well, and 100 µl of the transfection mixture was slowly incorporated in each well. A swine H1N1 influenza A virus strain was first grown onto Vero cells to produce a stock solution, aliquoted and stored at −80° C. The infectious mixture was prepared extemporaneously by diluting aliquots of the stock solution in DMEM supplemented with 0.2% BSA and 2 µg/ml trypsin-TPCK. Twenty-four hours after transfection, the cells were thoroughly washed three times with PBS and the infectious mixture was incorporated in each well, the target multiplicity of infection being ~1.

Codetection of MX Proteins and Influenza A Virus

Transfected-infected Vero cells were double immunolabelled for simultaneous detection of Mx proteins and influenza A virus nucleoprotein (NP) by flow cytometry. Five hours after infection, Vero cells were harvested by trypsinisation and pelleted at 300 g for 15 min. The cells were fixed with 4% (w/v) paraformaldehyde in PBS for 30 min at 4° C., permeabilized in PBS to which 0.2% (w/v) saponin had been added and blocked for 1 h in PBS, 0.2% saponin and 1% (w/v) BSA at room temperature. Cell were then incubated for 45 min with a cocktail of primary antibodies, i.e. the rabbit anti-huMXA and the rabbit anti-boMx1 antisera and an anti-NP mAb at 37° C. After three washing steps, the cells were incubated with the relevant Alexa 467- (NP) or 488-conjugated (Mx) secondary antibodies at 37° C. The immunolabelled cells were finally resuspended in PBS and analysed with the BD-Canto flow cytometer, gating on the forward and side scatter to exclude debris and collecting fluorescences in FL-1 and FL-5. A minimum of $10^4$ events were acquired and analysed with the BDFACSDiva software v4.1.1.

BoMx1 N-Terminal Segment Enhances Anti-Influenza Activity of Both Human and Bovine GED Given the reproducibility of the infection rate among non-expressing cells (FIG. 8) between transfection experiments, no matter what the plasmid tentatively incorporated was, the transfection procedure itself equally affected the cell populations transfected/infected. Moreover, as the infection rate of eGFP-expressing cells tended to be higher than that of non-expressing cells, it is deduced that the transduction process per se did not alter the viral lifecycle in the cell preparations studied. The systematic depletion ($p<0.05$) of NP-positive cells among Mx-expressing cell populations is, therefore, attributable to the Mx proteins themselves. Among these, boMx1 caused the strongest inhibition as expected. When the bovine GED was grafted on N-terminal segment of human MxA (chimera huN/GEDbo, the anti-influenza activity was dramatically reduced but not suppressed. Inversely, when the N-terminal segment of human MxA was substituted by that of bovine Mx1 (chimera boN/GEDhu), the anti-influenza activity was significantly enhanced. Taken together, the gathered data show that the N-terminal segment of bovine Mx1 dramatically enhances the GED-dependent anti-influenza activity, which a person skilled in the art would definitely not anticipate from prior art.

EXAMPLE 12

(with FIG. 9)

The N-Terminal Segment of a Narrow Subset of Mx1 Dynamins Comprises a Unique TRAF2/TRAF6 Binding Motif Careful in silico examinations of all Mx sequences available led to the discovery of a unique hexapeptide, "PEEESE" (Pro-Glu-Glu-Glu-Ser-Glu; SEQ ID NO: 9), inserted in the N-terminal segment of *Bos taurus, Ovis aries* and *Bubalus bubalis* Mx1 dynamins. This motif is absent from all other Mx dynamins sequenced to date. As this ruminant-specific hexapeptide simultaneously fits with the consensus TRAF2-binding motif pX(Q/E)E (SEQ ID NO: 2) and with the consensus TRAF6-binding motif pXEXX(Ar/Ac) (SEQ ID NO: 12), it could theoretically function as a TRAF2-and-TRAF6-binding-domain. Should this in silico prediction be confirmed in vivo, then this hexapeptide could endow bovine, ovine and buffalo Mx1s with the ability to interfere with transduction cascades linking TNF receptors, interleukin-1 receptor (IL-1R) and Toll-like receptor (TLR) superfamily on the one hand and survival/death pathways and activation of transcription factors nuclear factor-κB (NF-κB) and activator protein-1 (AP-1) on the other.

The TNF receptor (TNFR) superfamily consists of over 20 type-I transmembrane proteins which are specifically activated by the corresponding superfamily of TNF-like ligands. The downstream intracellular mediators of TNFRs are a group of proteins known as TNFR-associated factors (TRAFs). Among the latter, TRAFs 1, 2, 3 and 5 recognize and associate with TNFRs through a conserved sequence motif which does not overlap with that of TRAF6 (FIG. 9*a*). TRAF2-dependent regulation of survival and death pathways activated from TNFRs involve many molecular cascades among which cellular inhibitors of apoptosis (cIAPs), FLICE-inhibitory proteins (FLIPs) and c-Jun N-terminal kinase (JNK).

TRAF6 is the only TRAF family member that participates in the signal transduction of both the TNF receptor superfamily and the IL-1R/TLR superfamily. The TRAF6 signaling pathway for the IL-1R/TLR superfamily involves a group of adapter kinases upstream of TRAF6, namely IRAK1, IRAK2, IRAKM, which all contain several potential TRAF6 binding domains (FIG. 9*b*). TRAF6 also interacts directly with TNFR family members RANK and CD40 and with the kinase RIP2, which can activate NF-kB and induce cell death.

Therefore, the presence of a TRAF2- and of a TRAF6-binding-site in the N-terminal segment of the aforedescribed small subgroup of Mx proteins suggests that these proteins may play a role in mediating an array of cellular processes that would remain unaltered in the presence of any other Mx protein.

EXAMPLE 13

(with FIG. 10)

Bovine Mx1 Dynamin Binds TRAF2 Whereas PEEESE-Deficient Mx Dynamins do not

Cell culture and immunoprecipitation—Wild-type, huMxA-expressing VA8, poMx1-expressing VSK6 and boMx1-expressing V103 cell lines were cultured in DMEM supplemented with fetal bovine serum, penicillin, and streptomycin until semi-confluence and were then exposed either to vehicle or to doxycycline (1 µg/mL) for 24 hours. For immunoprecipatation, cells were then homogenized for 30 min at 4° C. in a modified RIPA buffer, containing 0.5% (vol/vol) NP-40, 0.1% (wt/vol) Na-Deoxycholate, and no SDS. Protease inhibitor cocktail was included in all lysates. For endogenous immunoprecipitation of TRAF2, 5×10$^7$ cells were incubated with anti-TRAF2 mAb for 4 hr, followed by treatment with 10 µl of protein G beads for an additional hour. The immunoprecipitated complexes were separated by SDS-PAGE and blotted with a cocktail of polyclonal rabbit anti-huMxA and anti-boMx1 antisera. Immune complexes were revealed with HRP-conjugated pig anti-rabbit IgG F(ab')2 fragments, and peroxidase detection with a CN/DAB Substrate Kit.

Figure 10:
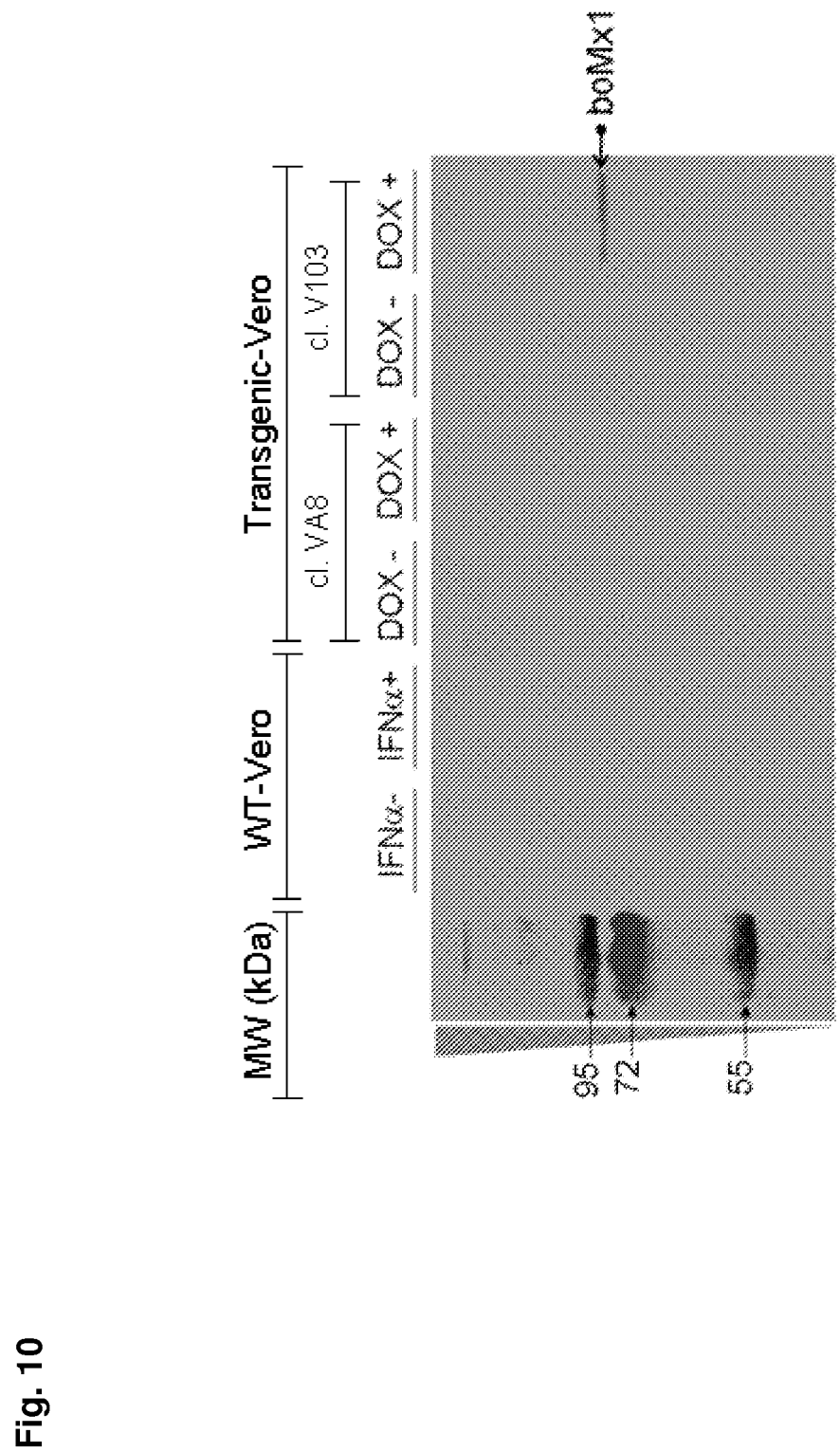
FIG. 10 shows that bovine Mx1 dynamin (boMx1) binds TRAF2 whereas PEEESE-deficient Mx dynamins do not. Wild-type, huMxA-expressing VA8, poMx1-expressing VSK6 and boMx1-expressing V103 cell lines were exposed either to vehicle or to IFN-alpha/doxycycline. Cell lysates were added with anti-TRAF2 mAB for endogenous immunoprecipitation. The immunoprecipitated complexes were separated by SDS-PAGE and blotted with a mixture of polyclonal rabbit anti-huMxA and anti-boMx1 antisera. Immune complexes were revealed with HRP-conjugated pig anti-rabbit IgG F(ab')2 fragments, and peroxidase detection with a CN/DAB Substrate Kit. A band with a 75 kDa apparent molecular weight that corresponds to boMx1 was reproducibly retrieved from induced V103 cells (expressing boMx1), but never from induced human MxA- (VA8), porcine Mx1- (VSK6) or Cercopithecus aethiops Mx-expressing (wild-type Vero cells) Vero cell lines. This shows that TRAF2 effectively binds to boMx1 but not to Mx proteins devoid of the PEEESE hexapeptide.

A band with a 75 kDa apparent molecular weight that is compatible with boMx1 was reproducibly retrieved from induced V103 cells, but never from induced human MxA-(VA8), porcine Mx1-(VSK6) or *Cercopithecus aethiops* Mx-expressing (wild-type Vero cells) Vero cell lines (FIG. 10), showing that TRAF2 effectively binds to boMx1 but not to Mx proteins devoid of the PEEESE hexapeptide. The unique TRAF2-and-TRAF6-binding-motif PEEESE inserted in a small subset of Mx proteins is therefore able to bind TRAF2 in vivo, which raises the possibility that the interactions of such Mx proteins with endogenous TRAF2 molecules could play a role in altering cellular processes subverted by infecting viruses.

EXAMPLE 14

Figure 11:
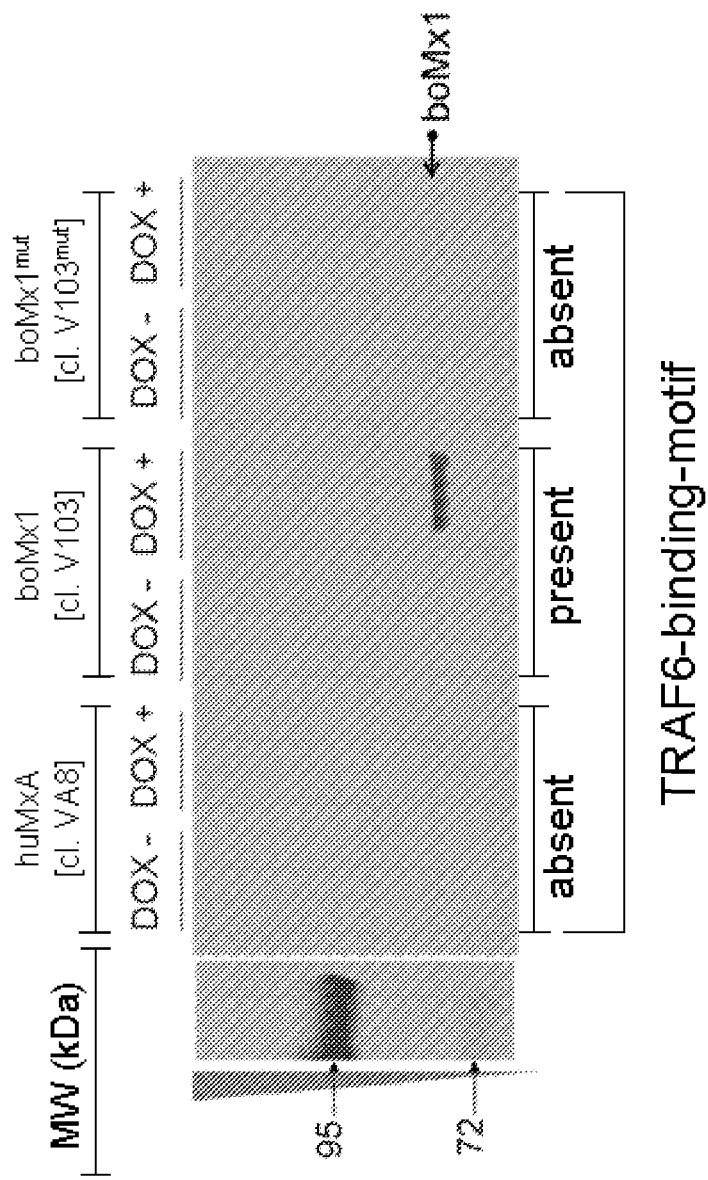
FIG. 11 shows that boMx1 dynamin binds TRAF6 whereas PEEESE-deficient Mx dynamins do not. boMx1 dynamin DNA constructs with two single point mutations (E356D and S358N: positions $P_0$ and $P_2$ of the TRAF2/TRAF6 consensus sequence, respectively) suppressing both the TRAF2- and the TRAF6-binding-motifs were generated. A Vero cell clone stably expressing this construct upon exposition to doxycycline was produced for the generation of Mx-expressing clones carrying the PEEESE deficient motif ($V103^{mut}$). Cercopithecus aethiops Mx-expressing, human MxA-expressing VA8, porcine Mx1-expressing, bovine Mx1-expressing V103, and the new PEEESE-deficient mutated boMx1-expressing $V103^{mut}$ Vero cell lines were cultured and were then exposed either to vehicle or to IFN-alpha or doxycycline. The cells were processed as described in example 13, except that, for immunoprecipitation, the anti-TRAF2 mAb was replaced by an anti-TRAF6 mAb. A band with a 75 kDa apparent molecular weight that is compatible with boMx1 was reproducibly retrieved from induced boMx1-expressing cells (clone V103), but never from induced human MxA- (clone VA8), porcine Mx1-(clone VSK6), *Cercopithecus aethiops* Mx- (wild-type Vero cells) or PEEESE-deficient bovine Mx1-expressing (clone V103$^{mut}$) Vero cell lines, showing that TRAF6 effectively binds to boMx1 but not to Mx proteins devoid of the PEEESE hexapeptide.

(with FIG. 11)

Bovine Mx1 Dynamin Binds TRAF6 Whereas PEEESE-Deficient Mx Dynamins do not boMx1 dynamin DNA constructs with two single point mutations (E356D & S358N) suppressing both the TRAF2- and the TRAF6-binding-motifs were generated. A Vero cell clone stably (V103$^{mut}$) expressing this construct upon exposition to doxycycline was produced as aforedescribed for the generation of Mx-expressing clones VA8, VSK6 and V103.

*Cercopithecus aethiops* Mx-expressing, human MxA-expressing VA8, porcine Mx1-expressing, bovine Mx1-expressing V103, and the new aforedescribed PEEESE-deficient mutated boMx1-expressing V103$^{mut}$ Vero cell lines were cultured in DMEM supplemented with fetal bovine serum, penicillin, and streptomycin until semi-confluence and were then exposed either to vehicle or to IFNα or doxycycline (1 µg/mL) for 24 hours. Afterwards, the cells were processed as described in example 12, except that, for immunoprecipitation, the anti-TRAF2 mAb was replaced by an anti-TRAF6 mAb.

A band with a 75 kDa apparent molecular weight that is compatible with boMx1 was reproducibly retrieved from induced boMx1-expressing cells (clone V103), but never from induced human MxA- (clone VA8), porcine Mx1-(clone VSK6), *Cercopithecus aethiops* Mx- (wild-type Vero cells) or PEEESE-deficient bovine Mx1-expressing (clone V103$^{mut}$) Vero cell lines (FIG. 11), showing that TRAF6 effectively binds to boMx1 but not to Mx proteins devoid of the PEEESE hexapeptide.

The unique TRAF2-and-TRAF6-binding-motif PEEESE inserted in a small subset of Mx proteins is therefore able to bind TRAF6 in vivo, which raises the possibility that the interactions of such Mx proteins with endogenous TRAF6 molecules could play a role in altering cellular processes subverted by infecting viruses.

EXAMPLE 15

Figure 12:
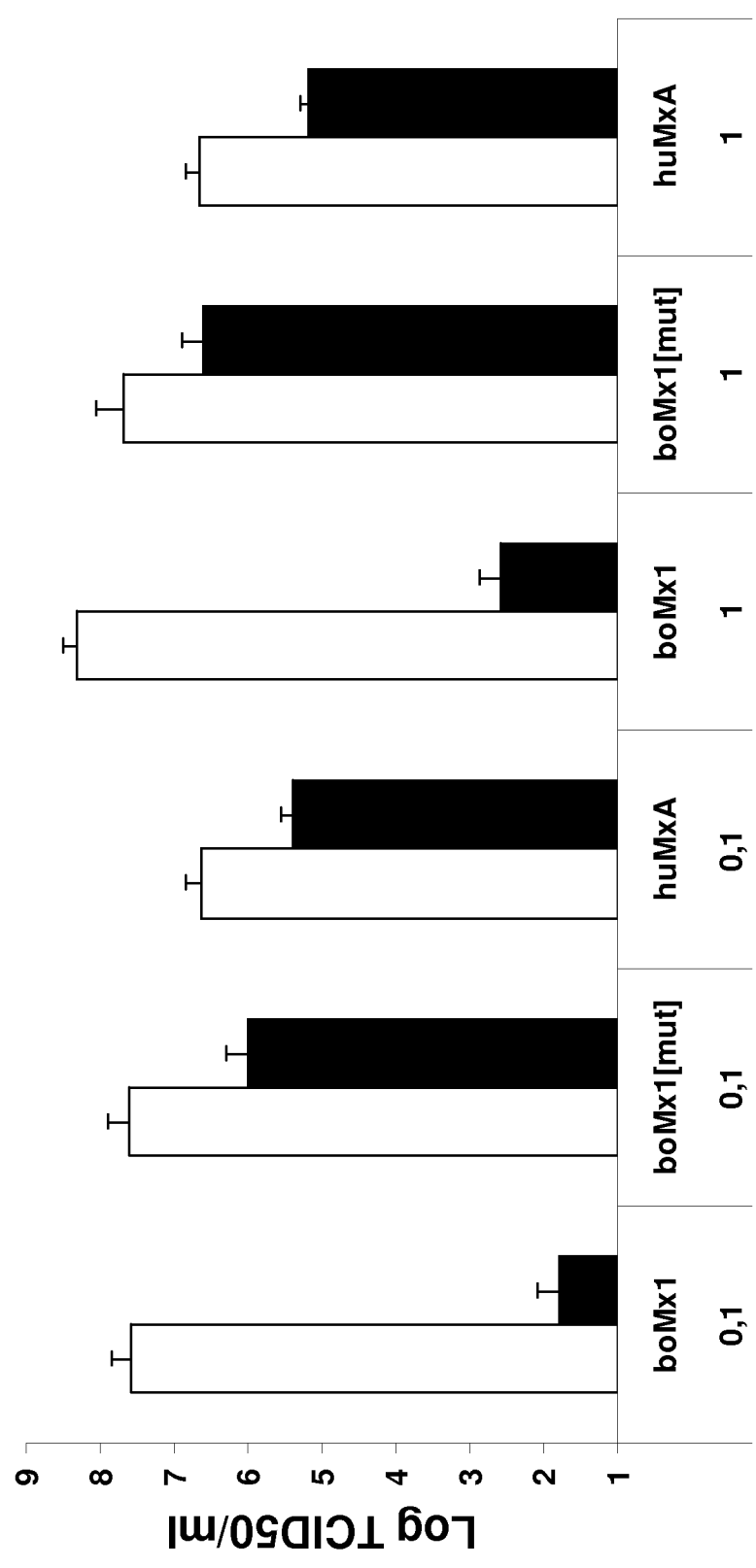
FIG. 12 shows that the Mx expression inhibits replication of a highly pathogenic avian influenza A virus. Anti-influenza activity was dramatically reduced in Vero cells expressing PEEESE-deficient boMx1. Pools of induced (black boxes, doxycycline 1 µg/mL) and noninduced (white boxes, vehicle) V103 (boMx1), V103$^{mut}$ (boMx1$^{mut}$) and VA8 (huMxA) cells were infected with appropriate dilutions of the H5N1 influenza A virus stock for 48 h. The viral titers in the culture supernatants are plotted, as determined in triplicate on chicken fibroblasts by standard median tissue culture infectious dose assays. TCID50: 50% tissue culture infective dose; 0.1 and 1 (below): multiplicities of infection. Plotted values are means±SD of 2-3 independent experiments.

(with FIG. 12)

Mutant Bovine Mx1 Dynamin that Lacks its Natural TRAF2/TRAF6 Binding Domain Displays Dramatically Diminished Anti-Influenza A Virus Activity, in Vero Cells Infected with Influenza A Virus H5N1 Strain In this example, the degree of resistance to influenza A virus replication conferred by expression of wild-type *Homo sapiens* and *Bos taurus* wild-type Mx1 isoforms and by expression of TRAF2-and-TRAF6-binding-site-deficient *Bos taurus* Mx1 was sought by measuring the 48-hours influenza A virus yield produced by Vero cell monolayers either nonexpressing or expressing the said Mx1 isoforms. The Vero cell clones used for this set of experiments were those aforedescribed, i.e. clone VA8 for human Mx1, clone V103 for bovine Mx1 and clone V103mut for mutated (PEEESE-deficient) boMx1.

A highly pathogenic avian H5N1 influenza A virus (A/crested_eagle/Belgium/1/2004) was used in this study. The virus was propagated and stocks were grown into embryonating chicken eggs and their titer was determined by standard median tissue culture infectious dose assays. For infections, stock aliquots were first diluted in DMEM supplemented with 0.2% BSA. Serial dilutions were prepared extemporaneously in order to generate volume-matched inoculums with appropriate multiplicities of infection and were incorporated onto induced (doxycycline) or noninduced (vehicle) V103, V103$^{mut}$ and VA8 cell monolayers, the target multiplicities of infection being 0.1 and 1. Upon infection, the inoculums were left to adsorb for 60 min at 37° C., before being removed by thoroughly washing with PBS. The cultures were then incubated at 37° C. in doxycycline-free DMEM. After 48 hours incubation at 37° C., culture supernatants were sampled, and the viral titers were determined in triplicate on chicken fibroblasts by standard median tissue culture infectious dose assays. All titers were calculated by the Reed-Muench method.

In the present experimental setting, in which the experimental conditions are strictly standardized, the anti-influenza activities brought by the three Mx isoforms were dramatically different (FIG. 12). Influenza A virus replication was ~10 000 times more repressed by expression of the wild-type bovine Mx1 than by expression of the mutated TRAF2-and-TRAF6-binding-site-deficient bovine Mx1 or by expression of wild-type human MxA. The TRAF2-and-TRAF6-binding-site therefore functions as a strong enhancer of GED-dependent anti-influenza activity, which a person skilled in the art would not be able to predict.

The invention claimed is:

1. A method of making a transgenic non-human animal that has a reduced likelihood of an influenza A virus-induced disease, the method comprising:

stably introducing into the genome of a non-human animal a gene encoding a chimeric Mx polypeptide comprising an exogenous TRAF2 and/or TRAF6 binding domain represented by the amino acid sequence P-E-E-E-S-E (SEQ ID NO:9), wherein the chimeric Mx polypeptide is obtained by introducing the exogenous TRAF2 and/or TRAF6 binding domain into a Mx polypeptide lacking an endogenous TRAF2 and/or TRAF6 binding domain, wherein the exogenous TRAF2 and/or TRAF6 binding domain is located in the chimeric Mx polypeptide at a position corresponding to the position of a hexapeptide P-E-E-E-S-E amino acid sequence in the bovine Mx1 protein or a position up to 20 amino acid residues upstream or downstream of said position of the hexapeptide P-E-E-E-S-E amino acid sequence, thereby making a transgenic non-human animal comprising the gene encoding the chimeric Mx polypeptide, wherein said transgenic non-human animal comprising the gene encoding the chimeric Mx polypeptide expresses the chimeric Mx polypeptide, wherein the transgenic non-human animal comprising the gene encoding the chimeric Mx polypeptide has a reduced likelihood of having an influenza A virus-induced disease, and wherein said reduced likelihood of having an influenza A virus-induced disease is reduced to a greater extent than a corresponding likelihood of having an influenza A virus-induced disease in a transgenic non-human animal comprising a stably introduced gene encoding the Mx polypeptide lacking the endogenous TRAF2 and/or TRAF6 binding domain in its genome.

2. The method of claim 1, wherein the chimeric Mx polypeptide and the Mx polypeptide sequence lacking the endogenous TRAF2 and/or TRAF6 binding domain comprise an Mx1 polypeptide.

3. The method of claim 1, wherein the chimeric Mx polypeptide and the Mx polypeptide lacking the endogenous TRAF2 and/or TRAF6 binding domain comprise a human Mx1 polypeptide or a derivative thereof having at least 95% identity thereto.

4. The method of claim 1, wherein the animal is selected from the group consisting of *Gallus* sp., *Maleagris* sp., Anatidae, *Sus* sp., *Equus* sp. and *Salmo* sp.

5. The method of claim 1, wherein influenza A virus replication in said transgenic non-human animal comprising the gene encoding the chimeric Mx polypeptide is 100-20,000 times more repressed as compared to the transgenic non-human animal comprising the Mx polypeptide lacking the endogenous TRAF2 and/or TRAF6 binding domain.

* * * * *

SEQUENCE LISTING

<160> NUMBER OF SEQ ID NOS: 77

<210> SEQ ID NO 1
<211> LENGTH: 6

-continued

```
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: Pro, Ser, Thr, Cys, Ile, Ala
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Gln or Glu
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Glu, Asp, Tyr, Phe or Trp

<400> SEQUENCE: 1

Xaa Xaa Xaa Xaa Xaa Xaa
1               5

<210> SEQ ID NO 2
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Gln or Glu

<400> SEQUENCE: 2

Pro Xaa Xaa Glu
1

<210> SEQ ID NO 3
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Gln or Glu
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Glu or Asp

<400> SEQUENCE: 3

Pro Xaa Xaa Xaa Xaa Xaa
1               5
```

```
<210> SEQ ID NO 4
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Gln or Glu
<220> FEATURE:
<221> NAME/KEY: misc_feature
<222> LOCATION: (4)..(5)
<223> OTHER INFORMATION: Xaa can be any naturally occurring amino acid

<400> SEQUENCE: 4

Pro Xaa Xaa Xaa Xaa Asp
1               5

<210> SEQ ID NO 5
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Asp, Glu, Tyr, Phe or Trp

<400> SEQUENCE: 5

Pro Xaa Glu Xaa Xaa Xaa
1               5

<210> SEQ ID NO 6
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 6

Pro Xaa Glu Xaa Xaa Glu
1               5

<210> SEQ ID NO 7
<211> LENGTH: 6
<212> TYPE: PRT
<213> ORGANISM: Artificial
<220> FEATURE:
<223> OTHER INFORMATION: synthetic peptide
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Pro Xaa Glu Glu Xaa Glu
1               5

<210> SEQ ID NO 8
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 8

Pro Glu Glu Glu Xaa Glu
1               5

<210> SEQ ID NO 9
<211> LENGTH: 6
<212> TYPE: PRT
<213> ORGANISM: Artificial
<220> FEATURE:
<223> OTHER INFORMATION: synthetic peptide

<400> SEQUENCE: 9

Pro Glu Glu Glu Ser Glu
1               5

<210> SEQ ID NO 10
<211> LENGTH: 6
<212> TYPE: PRT
<213> ORGANISM: Artificial
<220> FEATURE:
<223> OTHER INFORMATION: synthetic peptide

<400> SEQUENCE: 10

Pro Glu Asp Glu Asn Glu
1               5

<210> SEQ ID NO 11
<211> LENGTH: 6
<212> TYPE: PRT
<213> ORGANISM: Artificial
<220> FEATURE:
<223> OTHER INFORMATION: synthetic peptide

<400> SEQUENCE: 11

Pro Glu Glu Glu Asn Glu
1               5

<210> SEQ ID NO 12
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: misc_feature
```

-continued

```
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: amino acid having aromatic or acidic side chain

<400> SEQUENCE: 12

Pro Xaa Glu Xaa Xaa Xaa
1               5

<210> SEQ ID NO 13
<211> LENGTH: 6
<212> TYPE: PRT
<213> ORGANISM: Artificial
<220> FEATURE:
<223> OTHER INFORMATION: synthetic peptide

<400> SEQUENCE: 13

Pro Glu Asp Glu Ser Gly
1               5

<210> SEQ ID NO 14
<211> LENGTH: 648
<212> TYPE: PRT
<213> ORGANISM: Bos taurus

<400> SEQUENCE: 14

Met Val His Ser Asp Leu Gly Ile Glu Glu Leu Asp Ser Pro Glu Ser
1               5                   10                  15

Ser Leu Asn Gly Ser Glu Asp Met Glu Ser Lys Ser Asn Leu Tyr Ser
            20                  25                  30

Gln Tyr Glu Glu Lys Val Arg Pro Cys Ile Asp Leu Ile Asp Ser Leu
        35                  40                  45

Arg Ser Leu Gly Val Glu Gln Asp Leu Ala Leu Pro Ala Ile Ala Val
    50                  55                  60

Ile Gly Asp Gln Ser Ser Gly Lys Ser Ser Val Leu Glu Ala Leu Ser
65                  70                  75                  80

Gly Val Ala Leu Pro Arg Gly Ser Gly Ile Val Thr Arg Cys Pro Leu
                85                  90                  95

Val Leu Arg Leu Lys Lys Leu Gly Asn Glu Asp Glu Trp Lys Gly Lys
            100                 105                 110

Val Ser Phe Leu Asp Lys Glu Ile Glu Ile Pro Asp Ala Ser Gln Val
        115                 120                 125

Glu Lys Glu Ile Ser Glu Ala Gln Ile Ala Ile Ala Gly Glu Gly Thr
    130                 135                 140

Gly Ile Ser His Glu Leu Ile Ser Leu Glu Val Ser Ser Pro His Val
145                 150                 155                 160

Pro Asp Leu Thr Leu Ile Asp Leu Pro Gly Ile Thr Arg Val Ala Val
                165                 170                 175

Gly Asn Gln Pro Pro Asp Ile Glu Tyr Gln Ile Lys Ser Leu Ile Arg
            180                 185                 190

Lys Tyr Ile Leu Arg Gln Glu Thr Ile Asn Leu Val Val Val Pro Ala
        195                 200                 205

Asn Val Asp Ile Ala Thr Thr Glu Ala Leu Arg Met Ala Gln Glu Val
    210                 215                 220
```

```
Asp Pro Gln Gly Asp Arg Thr Ile Gly Ile Leu Thr Lys Pro Asp Leu
225                 230                 235                 240

Val Asp Lys Gly Thr Glu Asp Lys Val Val Asp Val Val Arg Asn Leu
                245                 250                 255

Val Phe His Leu Lys Lys Gly Tyr Met Ile Val Lys Cys Arg Gly Gln
            260                 265                 270

Gln Asp Ile Lys His Arg Met Ser Leu Asp Lys Ala Leu Gln Arg Glu
        275                 280                 285

Arg Ile Phe Phe Glu Asp His Ala His Phe Arg Asp Leu Leu Glu Glu
    290                 295                 300

Gly Lys Ala Thr Ile Pro Cys Leu Ala Glu Arg Leu Thr Ser Glu Leu
305                 310                 315                 320

Ile Met His Ile Cys Lys Thr Leu Pro Leu Leu Glu Asn Gln Ile Lys
                325                 330                 335

Glu Thr His Gln Arg Ile Thr Glu Glu Leu Gln Lys Tyr Gly Lys Asp
            340                 345                 350

Ile Pro Glu Glu Ser Glu Lys Met Phe Cys Leu Ile Glu Lys Ile
        355                 360                 365

Asp Thr Phe Asn Lys Glu Ile Ile Ser Thr Ile Glu Gly Glu Phe
    370                 375                 380

Val Glu Gln Tyr Asp Ser Arg Leu Phe Thr Lys Val Arg Ala Glu Phe
385                 390                 395                 400

Ser Lys Trp Ser Ala Val Val Glu Lys Asn Phe Glu Lys Gly Tyr Glu
                405                 410                 415

Ala Ile Arg Lys Glu Ile Lys Gln Phe Glu Asn Arg Tyr Arg Gly Arg
            420                 425                 430

Glu Leu Pro Gly Phe Val Asn Tyr Lys Thr Phe Glu Thr Ile Ile Lys
        435                 440                 445

Lys Gln Val Arg Val Leu Glu Glu Pro Ala Val Asp Met Leu His Thr
    450                 455                 460

Val Thr Asp Ile Ile Arg Asn Thr Phe Thr Asp Val Ser Gly Lys His
465                 470                 475                 480

Phe Asn Glu Phe Phe Asn Leu His Arg Thr Ala Lys Ser Lys Ile Glu
                485                 490                 495

Asp Ile Arg Leu Glu Gln Glu Asn Glu Ala Glu Lys Ser Ile Arg Leu
            500                 505                 510

His Phe Gln Met Glu Gln Leu Val Tyr Cys Gln Asp Gln Val Tyr Arg
        515                 520                 525

Arg Ala Leu Gln Gln Val Arg Glu Lys Glu Ala Glu Glu Lys Asn
    530                 535                 540

Lys Lys Ser Asn His Tyr Phe Gln Ser Gln Val Ser Glu Pro Ser Thr
545                 550                 555                 560

Asp Glu Ile Phe Gln His Leu Thr Ala Tyr Gln Gln Glu Val Ser Thr
                565                 570                 575

Arg Ile Ser Gly His Ile Pro Leu Ile Ile Gln Phe Phe Val Leu Arg
            580                 585                 590

Thr Tyr Gly Glu Gln Leu Lys Lys Ser Met Leu Gln Leu Leu Gln Asp
        595                 600                 605

Lys Asp Gln Tyr Asp Trp Leu Leu Lys Glu Arg Thr Asp Thr Arg Asp
    610                 615                 620

Lys Arg Lys Phe Leu Lys Glu Arg Leu Glu Arg Leu Thr Arg Ala Arg
625                 630                 635                 640

Gln Arg Leu Ala Lys Phe Pro Gly
```

-continued

```
                                   645

<210> SEQ ID NO 15
<211> LENGTH: 662
<212> TYPE: PRT
<213> ORGANISM: Homo sapiens

<400> SEQUENCE: 15

Met Val Ser Glu Val Asp Ile Ala Lys Ala Asp Pro Ala Ala Ala
1               5                   10                  15

Ser His Pro Leu Leu Asn Gly Asp Ala Thr Val Ala Gln Lys Asn
                20                  25                  30

Pro Gly Ser Val Ala Glu Asn Asn Leu Cys Ser Gln Tyr Glu Lys
                35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65              70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
                100                 105                 110

Lys Leu Val Asn Glu Asp Lys Trp Arg Gly Lys Val Ser Tyr Gln Asp
                115                 120                 125

Tyr Glu Ile Glu Ile Ser Asp Ala Ser Glu Val Glu Lys Glu Ile Asn
130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
                180                 185                 190

Asp Ile Gly Tyr Lys Ile Lys Thr Leu Ile Lys Lys Tyr Ile Gln Arg
                195                 200                 205

Gln Glu Thr Ile Ser Leu Val Val Pro Ser Asn Val Asp Ile Ala
                210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
                260                 265                 270

Lys Gly Tyr Met Ile Val Lys Cys Arg Gly Gln Gln Glu Ile Gln Asp
                275                 280                 285

Gln Leu Ser Leu Ser Glu Ala Leu Gln Arg Glu Lys Ile Phe Phe Glu
                290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
                340                 345                 350

Ile Thr Glu Glu Leu Gln Lys Tyr Gly Val Asp Ile Pro Glu Asp Glu
                355                 360                 365
```

```
Asn Glu Lys Met Phe Phe Leu Ile Asp Lys Val Asn Ala Phe Asn Gln
    370                 375                 380

Asp Ile Thr Ala Leu Met Gln Gly Glu Thr Val Gly Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly His Lys Ile Leu Ser Arg Lys
                420                 425                 430

Ile Gln Lys Phe Glu Asn Gln Tyr Arg Gly Arg Glu Leu Pro Gly Phe
            435                 440                 445

Val Asn Tyr Arg Thr Phe Glu Thr Ile Val Lys Gln Gln Ile Lys Ala
        450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
                500                 505                 510

Gln Glu Arg Glu Gly Glu Lys Leu Ile Arg Leu His Phe Gln Met Glu
            515                 520                 525

Gln Ile Val Tyr Cys Gln Asp Gln Val Tyr Arg Gly Ala Leu Gln Lys
        530                 535                 540

Val Arg Glu Lys Glu Leu Glu Glu Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
                580                 585                 590

Ser Ser His Ile Pro Leu Ile Ile Gln Phe Phe Met Leu Gln Thr Tyr
            595                 600                 605

Gly Gln Gln Leu Gln Lys Ala Met Leu Gln Leu Leu Gln Asp Lys Asp
        610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660

<210> SEQ ID NO 16
<211> LENGTH: 686
<212> TYPE: PRT
<213> ORGANISM: Sus scrofa

<400> SEQUENCE: 16

Met Val Tyr Ser Asn Cys Glu Ser Lys Glu Pro Asp Ser Val Ser Ala
1               5                   10                  15

Ser Asn His Leu Leu Leu Asn Gly Asn Asp Glu Leu Val Glu Lys Ser
            20                  25                  30

His Lys Thr Gly Pro Glu Asn Asn Leu Tyr Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80
```

```
Ser Gly Lys Ser Ser Val Leu Glu Ala Leu Ser Gly Val Ala Leu Pro
            85                  90                  95

Arg Gly Ser Gly Ile Val Thr Arg Cys Pro Leu Val Leu Lys Leu Lys
            100                 105                 110

Lys Leu Val Asn Glu Glu Asp Glu Trp Lys Gly Lys Val Ser Tyr Arg
            115                 120                 125

Asp Ser Glu Ile Glu Leu Ser Asp Ala Ser Gln Val Glu Lys Glu Val
            130                 135                 140

Ser Ala Ala Gln Ile Ala Ile Ala Gly Glu Gly Val Gly Ile Ser His
145                 150                 155                 160

Glu Leu Ile Ser Leu Glu Val Ser Ser Pro His Val Pro Asp Leu Thr
            165                 170                 175

Leu Ile Asp Leu Pro Gly Ile Thr Arg Val Ala Val Gly Asn Gln Pro
            180                 185                 190

Tyr Asp Ile Glu Tyr Gln Ile Lys Ser Leu Ile Lys Lys Tyr Ile Cys
            195                 200                 205

Lys Gln Glu Thr Ile Asn Leu Val Val Pro Cys Asn Val Asp Ile
            210                 215                 220

Ala Thr Thr Glu Ala Leu Arg Met Ala Gln Glu Val Asp Pro Glu Gly
225                 230                 235                 240

Asp Arg Thr Ile Gly Ile Leu Thr Lys Pro Asp Leu Val Asp Lys Gly
            245                 250                 255

Thr Glu Asp Lys Ile Val Asp Val Ala Arg Asn Leu Val Phe His Leu
            260                 265                 270

Lys Lys Gly Tyr Met Ile Val Lys Cys Arg Gly Gln Gln Asp Ile Gln
            275                 280                 285

Asp Gln Leu Ser Leu Ala Lys Ala Leu Gln Lys Glu Gln Ala Phe Phe
            290                 295                 300

Glu Asn His Glu His Phe Arg Asp Leu Leu Glu Glu Gly Arg Ala Thr
305                 310                 315                 320

Ile Pro Cys Leu Ala Glu Arg Leu Thr Ser Glu Leu Ile Met His Ile
            325                 330                 335

Cys Lys Thr Leu Pro Leu Leu Glu Asn Gln Ile Lys Glu Ser His Gln
            340                 345                 350

Lys Ile Thr Glu Glu Leu Gln Lys Tyr Gly Ser Asp Ile Pro Glu Asp
            355                 360                 365

Glu Ser Gly Lys Met Phe Phe Leu Ile Asp Lys Ile Asp Ala Phe Asn
370                 375                 380

Ser Asp Ile Thr Ala Leu Ile Gln Gly Glu Glu Leu Val Val Glu Tyr
385                 390                 395                 400

Glu Cys Arg Leu Phe Thr Lys Met Arg Asn Glu Phe Cys Lys Trp Ser
            405                 410                 415

Ala Val Val Glu Lys Asn Phe Lys Asn Gly Tyr Asp Ala Ile Cys Lys
            420                 425                 430

Gln Ile Gln Leu Phe Glu Asn Gln Tyr Arg Gly Arg Glu Leu Pro Gly
            435                 440                 445

Phe Val Asn Tyr Lys Thr Phe Glu Thr Ile Ile Lys Lys Gln Val Ser
            450                 455                 460

Val Leu Glu Glu Pro Ala Val Asp Met Leu His Thr Val Thr Asp Leu
465                 470                 475                 480

Val Arg Leu Ala Phe Thr Asp Val Ser Glu Thr Asn Phe Asn Glu Phe
            485                 490                 495
```

```
Phe Asn Leu His Arg Thr Ala Lys Ser Lys Ile Glu Asp Ile Lys Leu
                500                 505                 510

Glu Gln Glu Lys Glu Ala Glu Thr Ser Ile Arg Leu His Phe Gln Met
            515                 520                 525

Glu Gln Ile Val Tyr Cys Gln Asp Gln Val Tyr Arg Gly Ala Leu Gln
        530                 535                 540

Lys Val Arg Glu Lys Val Glu Glu Glu Lys Asn Arg Lys Ser Asn
545                 550                 555                 560

Gln Tyr Phe Leu Ser Ser Pro Ala Pro Ser Asp Pro Ser Ile Ala
                565                 570                 575

Glu Ile Phe Gln His Leu Ile Ala Tyr His Gln Glu Val Gly Lys Arg
            580                 585                 590

Ile Ser Ser His Ile Pro Leu Ile Ile Gln Phe Phe Ile Leu Arg Thr
        595                 600                 605

Phe Gly Gln Gln Leu Gln Lys Ser Met Leu Gln Leu Leu Gln Asn Lys
610                 615                 620

Asp Gln Tyr Asp Trp Leu Leu Arg Glu Arg Ser Asp Thr Ser Asp Lys
625                 630                 635                 640

Arg Lys Phe Leu Lys Glu Arg Leu Met Arg Leu Thr Gln Ala Arg Gln
                645                 650                 655

Val Pro Arg Leu Asn Arg Ala Leu Gln Ala Ala Arg Gly Leu Gln Gly
            660                 665                 670

Thr Ser Pro Gly Asn Glu Asp Gln Pro Pro Ser Leu Thr Asp
        675                 680                 685

<210> SEQ ID NO 17
<211> LENGTH: 662
<212> TYPE: PRT
<213> ORGANISM: Artificial
<220> FEATURE:
<223> OTHER INFORMATION: synthetic peptide

<400> SEQUENCE: 17

Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
                20                  25                  30

Pro Gly Ser Val Ala Glu Asn Asn Leu Cys Ser Gln Tyr Glu Glu Lys
            35                  40                  45

Val Arg Pro Cys Ile Asp Leu Ile Asp Ser Leu Arg Ala Leu Gly Val
        50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175
```

```
Ile Asp Leu Pro Gly Ile Thr Arg Val Ala Val Gly Asn Gln Pro Ala
            180                 185                 190
Asp Ile Gly Tyr Lys Ile Lys Thr Leu Ile Lys Lys Tyr Ile Gln Arg
            195                 200                 205
Gln Glu Thr Ile Ser Leu Val Val Pro Ser Asn Val Asp Ile Ala
    210                 215                 220
Thr Thr Glu Ala Leu Ser Met Ala Gln Glu Val Asp Pro Glu Gly Asp
225                 230                 235                 240
Arg Thr Ile Gly Ile Leu Thr Lys Pro Asp Leu Val Asp Lys Gly Thr
                245                 250                 255
Glu Asp Lys Val Val Asp Val Val Arg Asn Leu Val Phe His Leu Lys
            260                 265                 270
Lys Gly Tyr Met Ile Val Lys Cys Arg Gly Gln Gln Glu Ile Gln Asp
            275                 280                 285
Gln Leu Ser Leu Ser Glu Ala Leu Gln Arg Glu Lys Ile Phe Phe Glu
    290                 295                 300
Asn His Pro Tyr Phe Arg Asp Leu Leu Glu Glu Gly Lys Ala Thr Val
305                 310                 315                 320
Pro Cys Leu Ala Glu Lys Leu Thr Ser Glu Leu Ile Thr His Ile Cys
                325                 330                 335
Lys Ser Leu Pro Leu Leu Glu Asn Gln Ile Lys Glu Thr His Gln Arg
            340                 345                 350
Ile Thr Glu Glu Leu Gln Lys Tyr Gly Val Asp Ile Pro Glu Glu Glu
            355                 360                 365
Ser Glu Lys Met Phe Phe Leu Ile Asp Lys Val Asn Ala Phe Asn Gln
    370                 375                 380
Asp Ile Thr Ala Leu Met Gln Gly Glu Glu Thr Val Gly Glu Glu Asp
385                 390                 395                 400
Ile Arg Leu Phe Thr Arg Leu Arg His Glu Phe His Lys Trp Ser Thr
                405                 410                 415
Ile Ile Glu Asn Asn Phe Gln Glu Gly His Lys Ile Leu Ser Arg Lys
            420                 425                 430
Ile Gln Lys Phe Glu Asn Gln Tyr Arg Gly Arg Glu Leu Pro Gly Phe
            435                 440                 445
Val Asn Tyr Arg Thr Phe Glu Thr Ile Val Lys Gln Gln Ile Lys Ala
    450                 455                 460
Leu Glu Glu Pro Ala Val Asp Met Leu His Thr Val Thr Asp Met Val
465                 470                 475                 480
Arg Leu Ala Phe Thr Asp Val Ser Ile Lys Asn Phe Glu Glu Phe Phe
                485                 490                 495
Asn Leu His Arg Thr Ala Lys Ser Lys Ile Glu Asp Ile Arg Ala Glu
            500                 505                 510
Gln Glu Arg Glu Gly Glu Lys Leu Ile Arg Leu His Phe Gln Met Glu
            515                 520                 525
Gln Ile Val Tyr Cys Gln Asp Gln Val Tyr Arg Gly Ala Leu Gln Lys
    530                 535                 540
Val Arg Glu Lys Glu Leu Glu Glu Lys Lys Lys Ser Trp Asp
545                 550                 555                 560
Phe Gly Ala Phe Gln Ser Ser Ala Thr Asp Ser Ser Met Glu Glu
                565                 570                 575
Ile Phe Gln His Leu Met Ala Tyr His Gln Glu Ala Ser Lys Arg Ile
            580                 585                 590
Ser Ser His Ile Pro Leu Ile Ile Gln Phe Phe Met Leu Gln Thr Tyr
```

```
                   595                 600                 605
Gly Gln Gln Leu Gln Lys Ala Met Leu Gln Leu Leu Gln Asp Lys Asp
        610                 615                 620
Thr Tyr Ser Trp Leu Leu Lys Glu Arg Ser Asp Thr Ser Asp Lys Arg
625                 630                 635                 640
Lys Phe Leu Lys Glu Arg Leu Ala Arg Leu Thr Gln Ala Arg Arg Arg
                645                 650                 655
Leu Ala Gln Phe Pro Gly
            660

<210> SEQ ID NO 18
<211> LENGTH: 21
<212> TYPE: DNA
<213> ORGANISM: Artificial
<220> FEATURE:
<223> OTHER INFORMATION: synthetic DNA

<400> SEQUENCE: 18
cgcaaatggg cggtaggcgt g                                        21

<210> SEQ ID NO 19
<211> LENGTH: 18
<212> TYPE: DNA
<213> ORGANISM: Artificial
<220> FEATURE:
<223> OTHER INFORMATION: synthetic DNA

<400> SEQUENCE: 19
actggaaagc cccaaaat                                            18

<210> SEQ ID NO 20
<211> LENGTH: 18
<212> TYPE: DNA
<213> ORGANISM: Artificial
<220> FEATURE:
<223> OTHER INFORMATION: synthetic DNA

<400> SEQUENCE: 20
cctcgactgt gccttcta                                            18

<210> SEQ ID NO 21
<211> LENGTH: 20
<212> TYPE: DNA
<213> ORGANISM: Artificial
<220> FEATURE:
<223> OTHER INFORMATION: synthetic DNA

<400> SEQUENCE: 21
agagaaggag ctggaagaag                                          20

<210> SEQ ID NO 22
<211> LENGTH: 21
<212> TYPE: DNA
<213> ORGANISM: Artificial
<220> FEATURE:
<223> OTHER INFORMATION: synthetic DNA

<400> SEQUENCE: 22
cgcaaatggg cggtaggcgt g                                        21

<210> SEQ ID NO 23
<211> LENGTH: 20
<212> TYPE: DNA
<213> ORGANISM: Artificial
```

<220> FEATURE:
<223> OTHER INFORMATION: synthetic DNA

<400> SEQUENCE: 23
ggattggaag taatggtttg                                           20

<210> SEQ ID NO 24
<211> LENGTH: 18
<212> TYPE: DNA
<213> ORGANISM: Artificial
<220> FEATURE:
<223> OTHER INFORMATION: synthetic DNA

<400> SEQUENCE: 24
cctcgactgt gccttcta                                             18

<210> SEQ ID NO 25
<211> LENGTH: 20
<212> TYPE: DNA
<213> ORGANISM: Artificial
<220> FEATURE:
<223> OTHER INFORMATION: synthetic DNA

<400> SEQUENCE: 25
agagaaggag gcagaagaag                                           20

<210> SEQ ID NO 26
<211> LENGTH: 8
<212> TYPE: PRT
<213> ORGANISM: Artificial
<220> FEATURE:
<223> OTHER INFORMATION: synthetic peptide

<400> SEQUENCE: 26

Pro Phe Ser Lys Glu Glu Cys Ala
1               5

<210> SEQ ID NO 27
<211> LENGTH: 8
<212> TYPE: PRT
<213> ORGANISM: Artificial
<220> FEATURE:
<223> OTHER INFORMATION: synthetic peptide

<400> SEQUENCE: 27

Thr Ile Pro Ile Gln Glu Asp Tyr
1               5

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

His Tyr Pro Glu Gln Glu Thr Glu
1               5

<210> SEQ ID NO 29
<211> LENGTH: 8
<212> TYPE: PRT
<213> ORGANISM: Artificial
<220> FEATURE:
<223> OTHER INFORMATION: synthetic peptide

<400> SEQUENCE: 29

```
Met Leu Ser Val Glu Glu Glu Gly
1               5

<210> SEQ ID NO 30
<211> LENGTH: 8
<212> TYPE: PRT
<213> ORGANISM: Artificial
<220> FEATURE:
<223> OTHER INFORMATION: synthetic peptide

<400> SEQUENCE: 30

Ala Ala Pro Val Gln Glu Thr Leu
1               5

<210> SEQ ID NO 31
<211> LENGTH: 8
<212> TYPE: PRT
<213> ORGANISM: Artificial
<220> FEATURE:
<223> OTHER INFORMATION: synthetic peptide

<400> SEQUENCE: 31

Arg Thr Pro Ile Gln Glu Glu Gln
1               5

<210> SEQ ID NO 32
<211> LENGTH: 8
<212> TYPE: PRT
<213> ORGANISM: Artificial
<220> FEATURE:
<223> OTHER INFORMATION: synthetic peptide

<400> SEQUENCE: 32

Tyr Pro Ile Pro Glu Glu Gly Asp
1               5

<210> SEQ ID NO 33
<211> LENGTH: 8
<212> TYPE: PRT
<213> ORGANISM: Artificial
<220> FEATURE:
<223> OTHER INFORMATION: synthetic peptide

<400> SEQUENCE: 33

Ser Thr Pro His Gln Glu Asp Gly
1               5

<210> SEQ ID NO 34
<211> LENGTH: 8
<212> TYPE: PRT
<213> ORGANISM: Artificial
<220> FEATURE:
<223> OTHER INFORMATION: synthetic peptide

<400> SEQUENCE: 34

Thr Val Ala Val Glu Glu Thr Ile
1               5

<210> SEQ ID NO 35
<211> LENGTH: 8
<212> TYPE: PRT
<213> ORGANISM: Artificial
<220> FEATURE:
<223> OTHER INFORMATION: synthetic peptide

<400> SEQUENCE: 35
```

```
Ala Glu Thr Glu Glu Thr Ala
1               5

<210> SEQ ID NO 36
<211> LENGTH: 8
<212> TYPE: PRT
<213> ORGANISM: Artificial
<220> FEATURE:
<223> OTHER INFORMATION: synthetic peptide

<400> SEQUENCE: 36

Val Gln Thr Thr Gln Glu Glu Asp
1               5

<210> SEQ ID NO 37
<211> LENGTH: 8
<212> TYPE: PRT
<213> ORGANISM: Artificial
<220> FEATURE:
<223> OTHER INFORMATION: synthetic peptide

<400> SEQUENCE: 37

Arg Phe Pro Glu Glu Glu Glu Gly
1               5

<210> SEQ ID NO 38
<211> LENGTH: 8
<212> TYPE: PRT
<213> ORGANISM: Artificial
<220> FEATURE:
<223> OTHER INFORMATION: synthetic peptide

<400> SEQUENCE: 38

Thr Gly Ala Ala Gln Glu Glu Asp
1               5

<210> SEQ ID NO 39
<211> LENGTH: 8
<212> TYPE: PRT
<213> ORGANISM: Artificial
<220> FEATURE:
<223> OTHER INFORMATION: synthetic peptide

<400> SEQUENCE: 39

Arg Cys Pro Gln Glu Glu Glu Gly
1               5

<210> SEQ ID NO 40
<211> LENGTH: 8
<212> TYPE: PRT
<213> ORGANISM: Artificial
<220> FEATURE:
<223> OTHER INFORMATION: synthetic peptide

<400> SEQUENCE: 40

Ser Ser Ser Ser Glu Glu Ser Gly
1               5

<210> SEQ ID NO 41
<211> LENGTH: 8
<212> TYPE: PRT
<213> ORGANISM: Artificial
<220> FEATURE:
<223> OTHER INFORMATION: synthetic peptide

<400> SEQUENCE: 41

Gly Thr Thr Asp Glu Glu Asp Asp
```

```
<210> SEQ ID NO 42
<211> LENGTH: 8
<212> TYPE: PRT
<213> ORGANISM: Artificial
<220> FEATURE:
<223> OTHER INFORMATION: synthetic peptide

<400> SEQUENCE: 42

Arg Thr Pro Val Gln Glu Ser Gly
1               5

<210> SEQ ID NO 43
<211> LENGTH: 8
<212> TYPE: PRT
<213> ORGANISM: Artificial
<220> FEATURE:
<223> OTHER INFORMATION: synthetic peptide

<400> SEQUENCE: 43

Arg Pro Pro Val Gln Glu Thr Gly
1               5

<210> SEQ ID NO 44
<211> LENGTH: 8
<212> TYPE: PRT
<213> ORGANISM: Artificial
<220> FEATURE:
<223> OTHER INFORMATION: synthetic peptide

<400> SEQUENCE: 44

His Pro Pro Val Gln Glu Thr Gly
1               5

<210> SEQ ID NO 45
<211> LENGTH: 8
<212> TYPE: PRT
<213> ORGANISM: Artificial
<220> FEATURE:
<223> OTHER INFORMATION: synthetic peptide

<400> SEQUENCE: 45

His Pro Pro Ile Gln Glu Thr Gly
1               5

<210> SEQ ID NO 46
<211> LENGTH: 8
<212> TYPE: PRT
<213> ORGANISM: Artificial
<220> FEATURE:
<223> OTHER INFORMATION: synthetic peptide

<400> SEQUENCE: 46

Ser Val Pro Ile Gln Cys Thr Asp
1               5

<210> SEQ ID NO 47
<211> LENGTH: 8
<212> TYPE: PRT
<213> ORGANISM: Artificial
<220> FEATURE:
<223> OTHER INFORMATION: synthetic peptide

<400> SEQUENCE: 47

Pro His Pro Gln Gln Ala Thr Asp
1               5
```

```
<210> SEQ ID NO 48
<211> LENGTH: 8
<212> TYPE: PRT
<213> ORGANISM: Artificial
<220> FEATURE:
<223> OTHER INFORMATION: synthetic peptide

<400> SEQUENCE: 48

Pro Tyr Pro Ile Gln Ala Thr Asp
1               5

<210> SEQ ID NO 49
<211> LENGTH: 8
<212> TYPE: PRT
<213> ORGANISM: Artificial
<220> FEATURE:
<223> OTHER INFORMATION: synthetic peptide

<400> SEQUENCE: 49

Pro His Pro Ile Gln Ala Thr Asp
1               5

<210> SEQ ID NO 50
<211> LENGTH: 8
<212> TYPE: PRT
<213> ORGANISM: Artificial
<220> FEATURE:
<223> OTHER INFORMATION: synthetic peptide

<400> SEQUENCE: 50

Pro His Pro Val Gln Ala Ser Asp
1               5

<210> SEQ ID NO 51
<211> LENGTH: 9
<212> TYPE: PRT
<213> ORGANISM: Artificial
<220> FEATURE:
<223> OTHER INFORMATION: synthetic peptide

<400> SEQUENCE: 51

Lys Gln Glu Pro Gln Glu Ile Asp Phe
1               5

<210> SEQ ID NO 52
<211> LENGTH: 9
<212> TYPE: PRT
<213> ORGANISM: Artificial
<220> FEATURE:
<223> OTHER INFORMATION: synthetic peptide

<400> SEQUENCE: 52

Arg Gln Asp Pro Gln Glu Met Glu Asp
1               5

<210> SEQ ID NO 53
<211> LENGTH: 9
<212> TYPE: PRT
<213> ORGANISM: Artificial
<220> FEATURE:
<223> OTHER INFORMATION: synthetic peptide

<400> SEQUENCE: 53

Arg Gln Met Pro Thr Glu Asp Glu Tyr
1               5
```

<210> SEQ ID NO 54
<211> LENGTH: 9
<212> TYPE: PRT
<213> ORGANISM: Artificial
<220> FEATURE:
<223> OTHER INFORMATION: synthetic peptide

<400> SEQUENCE: 54

Phe Ser Glu Pro Leu Glu Val Gly Glu
1               5

<210> SEQ ID NO 55
<211> LENGTH: 9
<212> TYPE: PRT
<213> ORGANISM: Artificial
<220> FEATURE:
<223> OTHER INFORMATION: synthetic peptide

<400> SEQUENCE: 55

Arg Asn Pro Pro Gly Glu Asp Cys Glu
1               5

<210> SEQ ID NO 56
<211> LENGTH: 9
<212> TYPE: PRT
<213> ORGANISM: Artificial
<220> FEATURE:
<223> OTHER INFORMATION: synthetic peptide

<400> SEQUENCE: 56

Arg Lys Ile Pro Thr Glu Asp Glu Tyr
1               5

<210> SEQ ID NO 57
<211> LENGTH: 9
<212> TYPE: PRT
<213> ORGANISM: Artificial
<220> FEATURE:
<223> OTHER INFORMATION: synthetic peptide

<400> SEQUENCE: 57

Phe Gln Glu Pro Leu Glu Val Gly Glu
1               5

<210> SEQ ID NO 58
<211> LENGTH: 9
<212> TYPE: PRT
<213> ORGANISM: Artificial
<220> FEATURE:
<223> OTHER INFORMATION: synthetic peptide

<400> SEQUENCE: 58

Gly Asn Thr Pro Gly Glu Asp His Glu
1               5

<210> SEQ ID NO 59
<211> LENGTH: 9
<212> TYPE: PRT
<213> ORGANISM: Artificial
<220> FEATURE:
<223> OTHER INFORMATION: synthetic peptide

<400> SEQUENCE: 59

Pro Pro Ser Pro Gln Glu Asn Ser Tyr
1               5

```
<210> SEQ ID NO 60
<211> LENGTH: 9
<212> TYPE: PRT
<213> ORGANISM: Artificial
<220> FEATURE:
<223> OTHER INFORMATION: synthetic peptide

<400> SEQUENCE: 60

Pro Asn Gln Pro Val Glu Ser Asp Glu
1               5

<210> SEQ ID NO 61
<211> LENGTH: 9
<212> TYPE: PRT
<213> ORGANISM: Artificial
<220> FEATURE:
<223> OTHER INFORMATION: synthetic peptide

<400> SEQUENCE: 61

Arg Gln Gly Pro Glu Glu Ser Asp Glu
1               5

<210> SEQ ID NO 62
<211> LENGTH: 9
<212> TYPE: PRT
<213> ORGANISM: Artificial
<220> FEATURE:
<223> OTHER INFORMATION: synthetic peptide

<400> SEQUENCE: 62

Ser Asn Thr Pro Glu Glu Thr Asp Asp
1               5

<210> SEQ ID NO 63
<211> LENGTH: 9
<212> TYPE: PRT
<213> ORGANISM: Artificial
<220> FEATURE:
<223> OTHER INFORMATION: synthetic peptide

<400> SEQUENCE: 63

Pro Leu Leu Pro Thr Glu Asn Gly Glu
1               5

<210> SEQ ID NO 64
<211> LENGTH: 9
<212> TYPE: PRT
<213> ORGANISM: Artificial
<220> FEATURE:
<223> OTHER INFORMATION: synthetic peptide

<400> SEQUENCE: 64

Pro Ser Ile Pro Val Glu Asp Asp Glu
1               5

<210> SEQ ID NO 65
<211> LENGTH: 9
<212> TYPE: PRT
<213> ORGANISM: Artificial
<220> FEATURE:
<223> OTHER INFORMATION: synthetic peptide

<400> SEQUENCE: 65

Ser Pro Ser Pro Gln Glu Asn Ser Tyr
1               5

<210> SEQ ID NO 66
```

```
<211> LENGTH: 9
<212> TYPE: PRT
<213> ORGANISM: Artificial
<220> FEATURE:
<223> OTHER INFORMATION: synthetic peptide

<400> SEQUENCE: 66

Pro Asn Gln Pro Val Glu Ser Asp Glu
1               5

<210> SEQ ID NO 67
<211> LENGTH: 9
<212> TYPE: PRT
<213> ORGANISM: Artificial
<220> FEATURE:
<223> OTHER INFORMATION: synthetic peptide

<400> SEQUENCE: 67

Ser Gln Gly Pro Glu Glu Ser Asp Glu
1               5

<210> SEQ ID NO 68
<211> LENGTH: 9
<212> TYPE: PRT
<213> ORGANISM: Artificial
<220> FEATURE:
<223> OTHER INFORMATION: synthetic peptide

<400> SEQUENCE: 68

Ile Tyr Met Pro Pro Glu Asn Tyr Glu
1               5

<210> SEQ ID NO 69
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: Val or Lys

<400> SEQUENCE: 69

Xaa Asp Ile Pro Glu Glu Glu Ser Glu
1               5

<210> SEQ ID NO 70
<211> LENGTH: 6
<212> TYPE: PRT
<213> ORGANISM: Artificial
<220> FEATURE:
<223> OTHER INFORMATION: synthetic peptide

<400> SEQUENCE: 70

Pro Pro Glu Leu Arg Phe
1               5

<210> SEQ ID NO 71
<211> LENGTH: 6
<212> TYPE: PRT
<213> ORGANISM: Artificial
<220> FEATURE:
<223> OTHER INFORMATION: synthetic peptide

<400> SEQUENCE: 71

Pro Glu Glu Met Ser Trp
1               5
```

```
<210> SEQ ID NO 72
<211> LENGTH: 7
<212> TYPE: PRT
<213> ORGANISM: Artificial
<220> FEATURE:
<223> OTHER INFORMATION: synthetic peptide

<400> SEQUENCE: 72

Pro Glu Glu Thr Gly Ser Tyr
1               5

<210> SEQ ID NO 73
<211> LENGTH: 6
<212> TYPE: PRT
<213> ORGANISM: Artificial
<220> FEATURE:
<223> OTHER INFORMATION: synthetic peptide

<400> SEQUENCE: 73

Pro Val Glu Thr Thr Asp
1               5

<210> SEQ ID NO 74
<211> LENGTH: 6
<212> TYPE: PRT
<213> ORGANISM: Artificial
<220> FEATURE:
<223> OTHER INFORMATION: synthetic peptide

<400> SEQUENCE: 74

Pro Val Glu Asp Asp Glu
1               5

<210> SEQ ID NO 75
<211> LENGTH: 6
<212> TYPE: PRT
<213> ORGANISM: Artificial
<220> FEATURE:
<223> OTHER INFORMATION: synthetic peptide

<400> SEQUENCE: 75

Pro Glu Glu Asp Asp Asp
1               5

<210> SEQ ID NO 76
<211> LENGTH: 6
<212> TYPE: PRT
<213> ORGANISM: Artificial
<220> FEATURE:
<223> OTHER INFORMATION: synthetic peptide

<400> SEQUENCE: 76

Pro Trp Glu Ser Ala Pro
1               5

<210> SEQ ID NO 77
<211> LENGTH: 6
<212> TYPE: PRT
<213> ORGANISM: Artificial
<220> FEATURE:
<223> OTHER INFORMATION: synthetic peptide

<400> SEQUENCE: 77

Pro Pro Glu Gln Pro Pro
1               5
```